(12) United States Patent
Burkholder et al.

(10) Patent No.: US 6,316,445 B1
(45) Date of Patent: Nov. 13, 2001

(54) CARBOXY SUBSTITUTED ACYLIC CARBOXAMIDE DERIVATIVES

(75) Inventors: Timothy P. Burkholder, Carmel, IN (US); George D. Maynard, Clinton; Elizabeth M. Kudlacz, Groton, both of CT (US)

(73) Assignee: Aventis Pharmaceuticals Inc., Bridgewater, NJ (US)

( * ) Notice: Subject to any disclaimer, the term of this patent is extended or adjusted under 35 U.S.C. 154(b) by 0 days.

(21) Appl. No.: 09/648,005

(22) Filed: May 6, 1999

Related U.S. Application Data

(60) Provisional application No. 60/126,447, filed on May 15, 1998.

(51) Int. Cl.⁷ .................. C07D 401/14; C07D 401/06; C07D 413/06; A61K 31/495

(52) U.S. Cl. .................. 514/235.5; 514/253.04; 514/253.11; 514/253.12; 514/253.13; 514/316; 514/318; 514/326; 544/130; 544/364; 544/365; 546/187; 546/189; 546/194; 546/208; 546/210

(58) Field of Search .................. 514/235.5, 316, 514/318, 326, 253.09, 253.11, 253.12, 253.13; 544/130, 364, 365; 546/187, 189, 194, 208, 210

(56) References Cited

U.S. PATENT DOCUMENTS

| 5,236,921 | 8/1993 | Emonds-Alt et al. | 514/252 |
|---|---|---|---|
| 5,317,020 | 5/1994 | Emonds-Alt et al. | 514/255 |
| 5,340,822 | 8/1994 | Emonds-Alt et al. | 514/316 |
| 5,446,052 | 8/1995 | Emonds-Alt et al. | 514/318 |
| 5,635,510 | 6/1997 | Burkholder et al. | 514/278 |
| 5,830,906 | 11/1998 | Chabert et al. | 514/329 |

FOREIGN PATENT DOCUMENTS

| A-14909/95 | 9/1995 | (AU) | C07D/211/52 |
|---|---|---|---|
| 0 428 434 A2 | 5/1991 | (EP) | C07D/211/14 |
| 0 515 240 A1 | 11/1992 | (EP) | C07D/211/46 |
| 0 625 509 A1 | 11/1994 | (EP) | C07D/211/22 |
| 0 630 887 A1 | 12/1994 | (EP) | C07D/211/20 |
| 0 714 891 A1 | 6/1996 | (EP) | C07D/211/58 |
| 2 304 714 | 3/1997 | (GB) | C07D/211/04 |
| WO 96/10568 | 4/1996 | (WO) | C07D/295/15 |
| WO 96/24582 | 8/1996 | (WO) | C07D/211/52 |

OTHER PUBLICATIONS

"Modulation of Neurogenic Inflammation: Novel Approaches to Inflammatory Disease", Barnes et al., TIPS 11:185–189, 5/90.

"Protection Against Bradykinin–Induced Bronchoconstriction in Asthmatic Patients by Neurokinin Receptor Antagonist", Ichinose et al., The Lancet, vol. 340, p. 1248–1251, Nov. 21, 1992.

"In Vitro and In Vivo Characterization of MDL 105,212A, A Nonpeptide NK–1n/K–2 Tachykinin Receptor Antagonist", Kudlacz et al., J. Pharm Experimental Ther, 277*2) 840–851, 1996.

"Identification and Chemical Synthesis of MDL 105,212, A Non–Peptide Tachykinin Antagonist With High Affinity for NK–1 and NK–2 Receptors", Burkholder et al., Pergamon, 6: 951–956, 1996.

"Tetrazole NK–1 Receptor Antagonists: The Identification of an Exceptionally Potent Orally Active Antimetic Compound", Armour et al., Pergamon, 6: 1015–1020, 1996.

*Primary Examiner*—Mark L. Berch
*Assistant Examiner*—Kahsay Habte
(74) *Attorney, Agent, or Firm*—Michael W. Ferrell

(57) ABSTRACT

The present invention relates to novel carboxy substituted acyclic carboxamide derivatives of formula (1)):

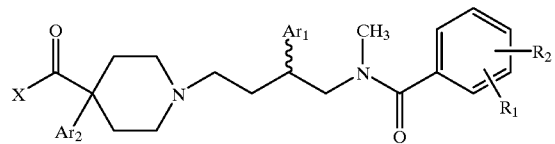

and stereoisomers and pharmaceutically acceptable salts thereof and their use as tachykinin receptor antagonists. Such antagonists are useful in the treatment of tachykinin-mediated diseases and conditions disclosed herein including: asthma, cough, and bronchitis.

21 Claims, No Drawings

CARBOXY SUBSTITUTED ACYLIC CARBOXAMIDE DERIVATIVES

CROSS REFERENCE TO RELATED APPLICATIONS

This patent application is a non-provisional patent application based on provisional patent application U.S. Ser. No. 60/126,447 filed on May 15, 1998 as a regular U.S. patent application Ser. No. 09/079,610 entitled NOVEL CARBOXY SUBSTITUTED ACYCLIC CARBOXAMIDE and converted to a provisional patent application on Feb. 23, 1999.

The present invention relates to novel carboxy substituted acyclic carboxamide derivatives (herein referred to as compounds or compounds of formula (1)), and stereoisomers thereof, and pharmaceutically acceptable salts thereof and their use as tachykinin receptor antagonists. Such antagonists are useful in the treatment of tachykinin-mediated diseases and conditions disclosed herein including: asthma, cough, and bronchitis.

SUMMARY OF THE INVENTION

The present invention relates to novel carboxy substituted acyclic carboxamide derivatives of formula (1):

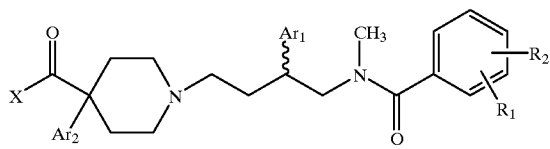

wherein
$R_1$ is from 1 to 3 substituents each independently chosen from the group consisting of hydrogen, halogen, $C_1$–$C_6$ alkyl, and $C_1$–$C_6$ alkoxy;
$R_2$ is hydrogen or a radical chosen from the group consisting of

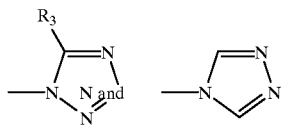

wherein
$R_3$ is selected from the group consisting of hydrogen, $C_1$–$C_4$ alkyl, and —$CF_3$;
$Ar_1$ is a radical chosen from the group consisting of

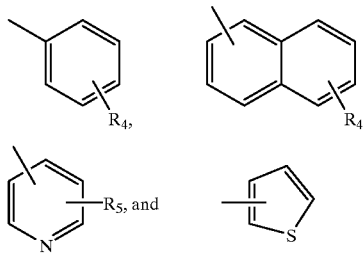

wherein
$R_4$ is from 1 to 3 substituents each independently chosen from the group consisting of hydrogen, halogen, hydroxy, —$CF_3$, $C_1$–$C_6$ alkyl, and $C_1$–$C_6$ alkoxy;

$R_5$ is from 1 to 2 substituents each independently chosen from the group consisting of hydrogen, halogen, $C_1$–$C_6$ alkyl, and $C_1$–$C_6$ alkoxy;
$Ar_2$ is a radical chosen from the group consisting of

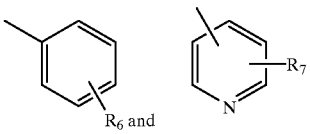

wherein
$R_6$ is from 1 to 3 substituents each independently chosen from the group consisting of hydrogen, halogen, —$CF_3$, $C_1$–$C_6$ alkyl, and $C_1$–$C_6$ alkoxy;
$R_7$ is from 1 to 2 substituents each independently chosen from the group consisting of hydrogen, halogen, $C_1$–$C_6$ alkyl, and $C_1$–$C_6$ alkoxy;
X is a radical selected from the group consisting of

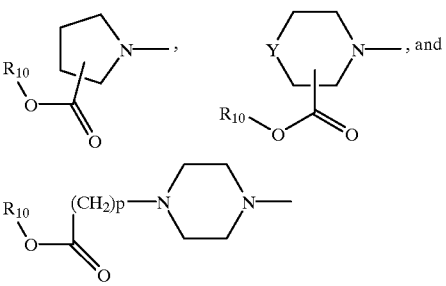

wherein
Y is —O— or —$CH_2$—;
p is an integer from 1 to 4;
$R_{10}$ is selected from the group consisting of hydrogen and $C_1$–$C_6$ alkyl;

and stereoisomers, and pharmaceutically acceptable salts thereof.

As is appreciated by one of ordinary skill in the art the compounds of the formula (1) exist as stereoisomers. Any reference in this application to one of the compounds of the formula (1) is meant to encompass either specific stereoisomers or a mixture of stereoisomers. Where indicated the compounds follow either the (+)- and (−)-designation for optical rotation or the Cahn-Ingold-Prelog designation of (R)- and (S)- for the stereochemistry of compounds represented by formula (1) and intermediates thereof. It is specifically recognized that the novel carboxy substituted acyclic carboxamide derivatives of the present invention are asymmetric at the 2-position of the butyl, that is, at the point of attachment of the $Ar_1$ substituent, and may exist in the (R)- or (S)-configuration or may be a mixture thereof. It is also specifically recognized that the novel substituted acyclic carboxamide derivatives of the present invention may be asymmetric at the point of attachment of the carboxy substituent on the heterocyclic carboxamide, and that, when asymmetric at that point of attachment, may be in either the (R)- or (S)-configuration or may be a mixture thereof.

The specific stereoisomers can be prepared by using enantiomerically pure or enantiomerically enriched starting materials obtained by stereospecific synthesis. The specific stereoisomers of either starting materials or products can be resolved and recovered by techniques known in the art, such as chromatography on chiral stationary phases, enzymatic resolution, or fractional recrystallization of addition salts formed by reagents used for that purpose. Useful methods of resolving and recovering specific stereoisomers are known in the art and described in *Stereochemistry of Organic Compounds*, E. L. Eliel and S. H. Wilen, Wiley (1994) and *Enantiomers, Racemates, and Resolutions*, J. Jacques, A. Collet, and S. H. Wilen, Wiley (1981).

As used in this application:

a) the term "halogen" refers to a fluorine atom, chlorine atom, bromine atom, or iodine atom;

b) the term "$C_1$–$C_6$ alkyl" refers to a branched or straight chained alkyl radical containing from 1 to 6 carbon atoms, such as methyl, ethyl, n-propyl, isopropyl, n-butyl, isobutyl, t-butyl, pentyl, hexyl, cyclopentyl, cyclohexyl, etc.;

c) the term "$C_1$–$C_6$ alkoxy" refers to a straight or branched alkoxy group containing from 1 to 6 carbon atoms, such as methoxy, ethoxy, n-propoxy, isopropoxy, n-butoxy, isobutoxy, t-butoxy, pentoxy, hexoxy, cyclopentoxy, cyclohexoxy, etc.;

d) as used in the examples and preparations, the following terms have the meanings indicated: "kg" refers to kilograms, "g" refers to grams, "mg" refers to milligrams, "μg" refers to micrograms, "mol" refers to moles, "mmol" refers to millimoles, "nmole" refers to nanomoles, "L" refers to liters, "mL" or "ml" refers to milliliters, "μL" refers to microliters, "° C." refers to degrees Celsius, "$R_f$" refers to retention factor, "mp" refers to melting point, "dec" refers to decomposition, "bp" refers to boiling point, "mm of Hg" refers to pressure in millimeters of mercury, "cm" refers to centimeters, "nm" refers to nanometers, "$[\alpha]_D^{20}$" refers to specific rotation of the D line of sodium at 20° C. obtained in a 1 decimeter cell, "c" refers to concentration in g/mL, "THF" refers to tetrahydrofuran, "DMF" refers to dimethylformamide, "brine" refers to a saturated aqueous sodium chloride solution, "M" refers to molar, "mM" refers to millimolar, "μM" refers to micromolar, "nM" refers to nanomolar, "psi" refers to pounds per square inch, "TLC" refers to thin layer chromatography, "HPLC" refers to high performance liquid chromatography, "HRMS" refers to high resolution mass spectrum, "μCi" refers to microcuries, "i.p." refers to intraperitoneally, "i.v." refers to intravenously, and "DPM" refers to disintegrations per minute;

e) the designation

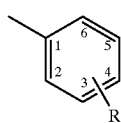

refers to a phenyl or a substituted phenyl and it is understood that the radical is attached at the 1-position and the substituent or substituents represented by R can be attached in any of the 2, 3, 4, 5, or 6 positions;

f) the designation

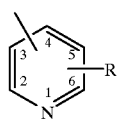

refers to a pyridine, substituted pyridine, pyridyl or substituted pyridyl and it is understood that the radical can be attached at either the 2-position, the 3-position, or the 4-position, it is further understood that when the radical is attached at the 2-position the substituent or substituents represented by R can be attached in any of the 3, 4, 5, or 6 positions, that when the radical is attached at the 3-position the substituent or substituents represented by R can be attached in any of the 2, 4, 5, or 6 positions, and that when the radical is attached at the 4-position the substituent or substituents represented by R can be attached in any of the 2, 3, 5, or 6 positions;

g) the designation

refers to a thiophene or thienyl and it is understood that the radical is attached at the 2 or 3-positions;

h) the designation

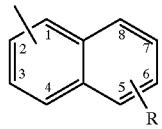

refers to a naphthalene, substituted naphthalene, naphthyl or substituted naphthyl and it is understood that the radical can be attached at either the 1-position or the 2-position, it is further understood that when the radical is attached at the 1-position the substituent or substituents represented by R can be attached in any of the 2, 3, 4, 5, 6, 7, or 8 positions and that when the radical is attached at the 2-position the substituent or substituents represented by R can be attached in any of the 1, 3, 4, 5, 6, 7, or 8 positions;

i) the term "enantiomeric excess" or "ee" refers to the percent by which one enantiomer, E1, is in excess in a mixture of the two enantiomers, E1 plus E2, such that {(E1−E2)÷(E1+E2)}×100%=ee;

j) the term "$C_1$–$C_4$ alkyl" refers to a saturated straight or branched chain alkyl group containing from 1–4 carbon atoms and includes methyl, ethyl, propyl, isopropyl, n-butyl, s-butyl, isobutyl, and t-butyl;

k) the designation ∿ refers to a bond for which the stereochemistry is not designated;

l) the designation ◂▬ refers to a bond that protrudes forward out of the plane of the page;

m) the designation ⋯⫼⫼ refers to a bond that protrudes backward out of the plane of the page n) the term "pharmaceutically acceptable salts thereof" refers to either an acid addition salt or a basic addition salt.

The expression "pharmaceutically acceptable acid addition salts" is intended to apply to any non-toxic organic or inorganic acid addition salt of the base compounds represented by formula (1) or any of its intermediates. Illustrative inorganic acids which form suitable salts include hydrochloric, hydrobromic, sulphuric, and phosphoric acid and acid metal salts such as sodium monohydrogen orthophosphate, and potassium hydrogen sulfate. Illustrative organic acids which form suitable salts include the mono-, di-, and tricarboxylic acids. Illustrative of such acids are for example, acetic, glycolic, lactic, pyruvic, malonic, succinic, glutaric, fumaric, malic, tartaric, citric, ascorbic, maleic, hydroxymaleic, benzoic, hydroxybenzoic, phenylacetic, cinnamic, salicyclic, 2-phenoxybenzoic, p-toluenesulfonic acid, and sulfonic acids such as methane sulfonic acid and 2-hydroxyethane sulfonic acid. Such salts can exist in either a hydrated or substantially anhydrous form. In general, the acid addition salts of these compounds are soluble in water and various hydrophilic organic solvents, and which in comparison to their free base forms, generally demonstrate higher melting points.

The expression "pharmaceutically acceptable basic addition salts" is intended to apply to any non-toxic organic or inorganic basic addition salts of the compounds represented by formula (1) or any of its intermediates. Illustrative bases which form suitable salts include alkali metal or alkaline-earth metal hydroxides such as sodium, potassium, calcium, magnesium, or barium hydroxides; ammonia, and aliphatic, alicyclic, or aromatic organic amines such as methylamine, dimethylamine, trimethylamine, and picoline.

As with any group of structurally related compounds which possess a particular utility, certain groups and configurations of substituents are preferred for the compounds of formula (1). Preferred embodiments are given below:

1) Compounds in which $R_2$ is hydrogen and $R_1$ is 3,4,5-trimethoxy are preferred;
2) Compounds in which $R_2$ is the radical

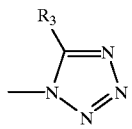

are preferred;
3) Compounds in which $R_2$ is the radical

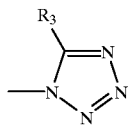

in which $R_3$ is hydrogen are more preferred;
4) Compounds in which $R_1$ is 2-methoxy and $R_2$ is in the 5-position and is the radical

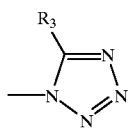

in which $R_3$ is hydrogen are most preferred;

5) Compounds in which $Ar_1$ is a radical chosen from the group consisting of

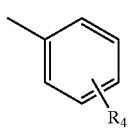 and 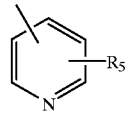

in which $R_4$ and $R_5$ are defined above are preferred;
6) Compounds in which $Ar_1$ is the radical

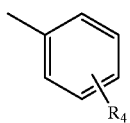

in which $R_4$ is defined above are more preferred;
7) Compounds in which $Ar_1$ is phenyl, 3,4-dichlorophenyl, or 4-fluorophenyl are most preferred;
8) Compounds in which X is the radical

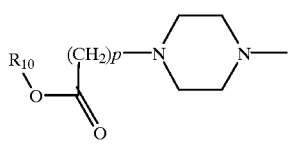

in which $R_{10}$ and p are as defined above are preferred;
9) Compounds in which X is the radical

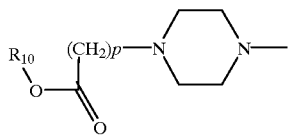

wherein p is 1 or 2 are more preferred;
10) Compounds in which X is the radical

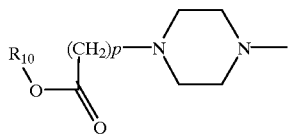

wherein $R_{10}$ is hydrogen or ethyl are more preferred.

It is understood that further preferred embodiments of formula (1) can be selected by requiring one or more of the preferred embodiments 1 through 10 or by reference to examples given herein.

Examples of compounds encompassed by the present invention include the following. It is understood that the examples encompass both the individual isomers of the compounds and mixtures thereof. This list is meant to be representative only and is not intended to limit the scope of the invention in any way:

N-Methyl-N-(4-phenyl-4-((4-carboethoxymethylpiperazin-1-yl)carboxamido)piperidin-1-yl)-2-phenylbutyl) benzamide;

N-Methyl-N-(4-phenyl-4-((4-carboethoxymethylpiperazin-1-yl)carboxamido)piperidin-1-yl)-2-(3,4-dichlorophenyl) butyl)benzamide;

N-Methyl-N-(4-phenyl-4-((4-carboethoxymethylpiperazin-1-yl)carboxamido)piperidin-1-yl)-2-(4-fluorophenylphenyl)butyl)benzamide;

N-Methyl-N-(4-phenyl-4-((4-carboethoxymethylpiperazin-1-yl)carboxamido)piperidin-1-yl)-2-phenylbutyl)-3,4,5-trimethoxybenzamide;

N-Methyl-N-(4-phenyl-4-((4-carboethoxymethylpiperazin-1-yl)carboxamido)piperidin-1-yl)-2-(3,4-dichlorophenyl)butyl)-3,4,5-trimethoxybenzamide;

N-Methyl-N-(4-phenyl-4-((4-carboethoxymethylpiperazin-1-yl)carboxamido)piperidin-1-yl)-2-(4-fluorophenylphenyl)-3,4,5-trimethoxybenzamide;

N-Methyl-N-(4-(4-phenyl-4-((4-carboethoxymethylpiperazin-1-yl)carboxamido)piperidin-1-yl)-2-phenylbutyl)-2-methoxy-5-(1H-tetrazol-1-yl)benzamide;

N-Methyl-N-(4-(4-phenyl-4-((4-carboethoxymethylpiperazin-1-yl)carboxamido)piperidin-1-yl)-2-(3,4-dichlorophenyl)butyl)-2-methoxy-5-(1H-tetrazol-1-yl)benzamide;

N-Methyl-N-(4-(4-phenyl-4-((4-carboethoxymethylpiperazin-1-yl)carboxamido)piperidin-1-yl)-2-(4-fluorophenyl)butyl)-2-methoxy-5-(1H-tetrazol-1-yl)benzamide;

N-Methyl-N-(4-phenyl-4-((4-carboethoxyethylpiperazine-1-yl)carboxamido)piperidin-1-yl)-2-phenylbutyl)benzamide;

N-Methyl-N-(4-phenyl-4-((4-carboethoxyethylpiperazine-1-yl)carboxamido)piperidin-1-yl)-2-(3,4-dichlorophenyl)butyl)benzamide;

N-Methyl-N-(4-phenyl-4-((4-carboethoxyethylpiperazine-1-yl)carboxamido)piperidin-1-yl)-2-(4-fluorophenylphenyl)butyl)benzamide;

N-Methyl-N-(4-phenyl-4-((4-carboethoxyethylpiperazine-1-yl)carboxamido)piperidin-1-yl)-2-phenylbutyl)-3,4,5-trimethoxybenzamide;

N-Methyl-N-(4-phenyl-4-((4-carboethoxyethylpiperazine-1-yl)carboxamido)piperidin-1-yl)-2-(3,4-dichlorophenyl)butyl)-3,4,5-trimethoxybenzamide;

N-Methyl-N-(4-phenyl-4-((4-carboethoxyethylpiperazine-1-yl)carboxamido)piperidin-1-yl)-2-(4-fluorophenylphenyl)-3,4,5-trimethoxybenzamide;

N-Methyl-N-(4-(4-phenyl-4-((4-carboethoxyethylpiperazine-1-yl)carboxamido)piperidin-1-yl)-2-phenylbutyl)-2-methoxy-5-(1H-tetrazol-1-yl)benzamide;

N-Methyl-N-(4-(4-phenyl-4-((4-carboethoxyethylpiperazine-1-yl)carboxamido)piperidin-1-yl)-2-(3,4-dichlorophenyl)butyl)-2-methoxy-5-(1H-tetrazol-1-yl)benzamide;

N-Methyl-N-(4-(4-phenyl-4-((4-carboethoxyethylpiperazine-1-yl)carboxamido)piperidin-1-yl)-2-(4-fluorophenyl)butyl)-2-methoxy-5-(1H-tetrazol-1-yl)benzamide;

N-Methyl-N-(4-phenyl-4-((4-carboxymethylpiperazin-1-yl)carboxamido)piperidin-1-yl)-2-phenylbutyl)benzamide;

N-Methyl-N-(4-phenyl-4-((4-carboxymethylpiperazin-1-yl)carboxamido)piperidin-1-yl)-2-(3,4-dichlorophenyl)butyl)benzamide;

N-Methyl-N-(4-phenyl-4-((4-carboxymethylpiperazin-1-yl)carboxamido)piperidin-1-yl)-2-(4-fluorophenylphenyl)butyl)benzamide;

N-Methyl-N-(4-phenyl-4-((4-carboxymethylpiperazin-1-yl)carboxamido)piperidin-1-yl)-2-phenylbutyl)-3,4,5-trimethoxybenzamide;

N-Methyl-N-(4-phenyl-4-((4-carboxymethylpiperazin-1-yl)carboxamido)piperidin-1-yl)-2-(3,4-dichlorophenyl)butyl)-3,4,5-trimethoxybenzamide;

N-Methyl-N-(4-phenyl-4-((4-carboxymethylpiperazin-1-yl)carboxamido)piperidin-1-yl)-2-(4-fluorophenylphenyl)-3,4,5-trimethoxybenzamide;

N-Methyl-N-(4-(4-phenyl-4-((4-carboxymethylpiperazin-1-yl)carboxamido)piperidin-1-yl)-2-phenylbutyl)-2-methoxy-5-(1H-tetrazol-1-yl)benzamide;

N-Methyl-N-(4-(4-phenyl-4-((4-carboxymethylpiperazin-1-yl)carboxamido)piperidin-1-yl)-2-(3,4-dichlorophenyl)butyl)-2-methoxy-5-(1H-tetrazol-1-yl)benzamide;

N-Methyl-N-(4-(4-phenyl-4-((4-carboxymethylpiperazin-1-yl)carboxamido)piperidin-1-yl)-2-(4-fluorophenyl)butyl)-2-methoxy-5-(1H-tetrazol-1-yl)benzamide;

N-Methyl-N-(4-phenyl-4-((4-carboxyethylpiperazine-1-yl)carboxamido)piperidin-1-yl)-2-phenylbutyl)benzamide;

N-Methyl-N-(4-phenyl-4-((4-carboxyethylpiperazine-1-yl)carboxamido)piperidin-1-yl)-2-(3,4-dichlorophenyl)butyl)benzamide;

N-Methyl-N-(4-phenyl-4-((4-carboxyethylpiperazine-1-yl)carboxamido)piperidin-1-yl)-2-(4-fluorophenylphenyl)butyl)benzamide;

N-Methyl-N-(4-phenyl-4-((4-carboxyethylpiperazine-1-yl)carboxamido)piperidin-1-yl)-2-phenylbutyl)-3,4,5-trimethoxybenzamide;

N-Methyl-N-(4-phenyl-4-((4-carboxyethylpiperazine-1-yl)carboxamido)piperidin-1-yl)-2-(3,4-dichlorophenyl)butyl)-3,4,5-trimethoxybenzamide;

N-Methyl-N-(4-phenyl-4-((4-carboxyethylpiperazine-1-yl)carboxamido)piperidin-1-yl)-2-(4-fluorophenylphenyl)-3,4,5-trimethoxybenzamide;

N-Methyl-N-(4-(4-phenyl-4-((4-carboxyethylpiperazine-1-yl)carboxamido)piperidin-1-yl)-2-phenylbutyl)-2-methoxy-5-(1H-tetrazol-1-yl)benzamide;

N-Methyl-N-(4-(4-phenyl-4-((4-carboxyethylpiperazine-1-yl)carboxamido)piperidin-1-yl)-2-(3,4-dichlorophenyl)butyl)-2-methoxy-5-(1H-tetrazol-1-yl)benzamide;

N-Methyl-N-(4-(4-phenyl-4-((4-carboxyethylpiperazine-1-yl)carboxamido)piperidin-1-yl)-2-(4-fluorophenyl)butyl)-2-methoxy-5-(1H-tetrazol-1-yl)benzamide.

General synthetic procedures for preparing the compounds of formula (1) is set forth in Reaction Schemes A.1 and A.2. The reagents and starting materials in Reaction Schemes A.1 and A.2 are readily available to one of ordinary skill in the art. In Reaction Schemes A.1 and A.2, all substituents, unless otherwise indicated, are as previously defined.

Reaction Scheme A.1

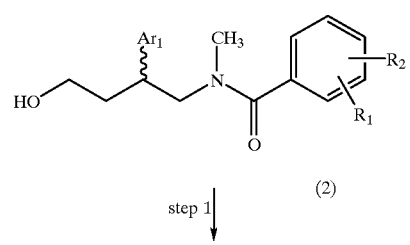

step 1

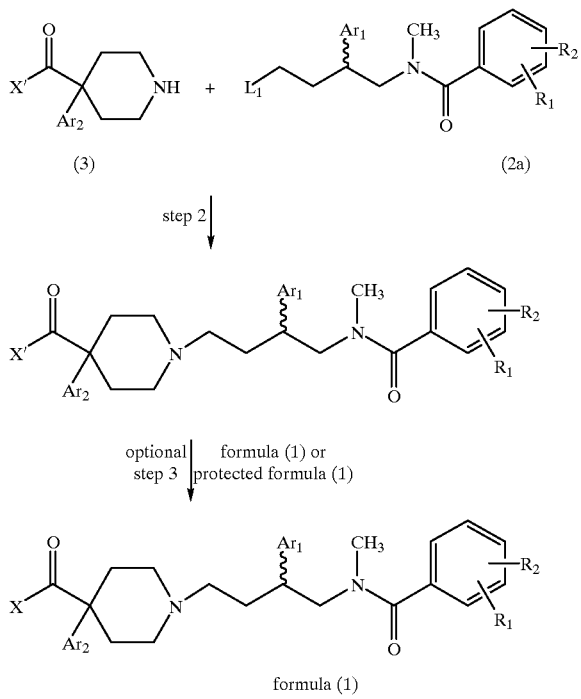

formula (1)

In Reaction Scheme A.1, step 1, the hydroxy group of an appropriate alcohol of structure 2 is converted to an appropriate leaving group to give a compound of structure 2a. An appropriate alcohol of structure 2 is one in which the stereochemistry is as desired in the final product of formula (1) and $R_1$, $R_2$, and $Ar_1$ are as desired in the final product of formula (1). Alternately, an appropriate alcohol of structure 2 can be one in which the stereochemistry gives rise after resolution to stereochemistry as desired in the final product of formula (1) and $R_1$, $R_2$, and $Ar_1$ are as desired in the final product of formula (1). An appropriate alcohol of structure 2 can also be one in which the stereochemistry and $R_1$ and $R_2$ are as desired in the final product of formula (1) and $Ar_1$ gives rise upon deprotection to $Ar_1$ as desired in the final product of formula (1). Alternately, an appropriate alcohol of structure 2 can also be one in which the stereochemistry gives rise after resolution to stereochemistry as desired in the final product of formula (1), $R_1$ and $R_2$ are as desired in the final product of formula (1), and $Ar_1$ gives rise upon deprotection to $Ar_1$ as desired in the final product of formula (1).

An appropriate alcohol of structure 2 can be prepared by methods described herein and by methods which are well known and appreciated in the art, such as U.S. Pat. Nos. 5,317,020 and 5,236,921; European Patent Application Nos. 0 428 434, published May 22, 1991, 0 630 887, published Dec. 28, 1994, and 0 559 538, published Sep. 8, 1993; PCT Application Nos. WO 94/17045, published Aug. 4, 1994, WO 95/415961, published Jun. 15, 1995, and WO 97/30991, published Aug. 28, 1997.

An appropriate leaving group, $L_1$, is one which can be displaced by a piperidine of structure 3 to give rise to a compound of formula (1). Appropriate leaving groups, $L_1$, include but are not limited to chloro, bromo, iodo, mesylate, tosylate, benzenesulfonate, and the like. The conversion of hydroxy groups to leaving groups such as chloro, bromo, iodo, mesylate, tosylate, and benzenesulfonate is well known and appreciated in the art.

For example, compounds in which $L_1$ is bromo are formed by contacting an appropriate alcohol of structure 2 with 1.0 to 1.5 molar equivalents of carbon tetrabromide and 1.0 to 1.75 molar equivalents triphenylphosphine. (P. J. Kocienski et al. *J. Org. Chem.*, 42, 353–355 (1977)). The reaction is carried out by combining the alcohol of structure 2 with carbon tetrabromide in a suitable solvent, such as dichloromethane or chloroform and then adding a solution of triphenylphosphine in a suitable solvent, such as dichloromethane or chloroform. Generally the reaction is carried out at temperatures of from −10° C. to ambient temperature. Generally, the reactions require from 5 minutes to 24 hours. The product can be isolated and purified by techniques well known in the art, such as extraction, evaporation, trituration, chromatography, and recrystallization.

Compounds in which $L_1$ is bromo are also formed by contacting an appropriate alcohol of structure 2 with a slight molar excess of triphenylphosphine dibromide. (R. F Borch et al. *J. Am. Chem. Soc.*, 99, 1612–1619 (1977)). The reaction may be carried out by contacting an appropriate alcohol of structure 2 with preformed triphenylphosphine dibromide. The reaction is carried out in a suitable solvent, such as tetrahydrofuran and diethyl ether. The reaction is carried out in the presence of a suitable base, such as pyridine. Generally the reaction is carried out at temperatures of from 0° C. to 50° C. Generally, the reactions require from 5 minutes to 24 hours. The product can be isolated and purified by techniques well known in the art, such as extraction, evaporation, trituration, chromatography, and recrystallization.

Alternately, for example, compounds in which $L_1$ is mesylate are formed by contacting an appropriate alcohol of structure 2 with a molar excess of methanesulfonyl chloride. The reaction is carried out in a suitable solvent, such as dichloromethane, chloroform, toluene, benzene, or pyridine. The reaction is carried out in the presence of a suitable base, such as triethylamine, N,N-diisopropylethylamine, or pyridine. Generally the reaction is carried out at temperatures of from −20° C. to 50° C. Generally, the reactions require from 1 hour to 24 hours. The product can be isolated and purified by techniques well known in the art, such as extraction, evaporation, trituration, chromatography, and recrystallization.

Compounds of structure 2a in which $L_1$ is iodo can be prepared from compounds of structure 2a in which $L_1$ is mesylate, chloro, or bromo by an exchange reaction, such as the Finkelstein reaction.

For example, a compound of structure 2a is contacted from about 1.0 to 10.0 molar equivalents of an iodide salt, such as sodium iodide or potassium iodide may also be added. The reaction is carried out in a suitable solvent, such as acetone, butanone, tetrahydrofuran, tetrahydrofuran/water mixtures, toluene, and acetonitrile. Generally, the reaction is carried out at temperatures of from ambient temperature to the refluxing temperature of the solvent. Generally, the reactions require from 1 hour to 24 hours. The product can be isolated and purified by techniques well known in the art, such as extraction, evaporation, trituration, chromatography, and recrystallization.

In Reaction Scheme A.1, step 2, the compound of structure 2a reacts with an appropriate piperidine of structure 3 or a salt thereof to give a protected compound of formula (1) or a compound of formula (1). An appropriate piperidine of formula 3 is one in which $Ar_2$ is as desired in the final product of formula (1) and X' is either X as desired in the final product of formula (1), gives rise after deprotection to X as desired in the final product of formula (1), or gives rise after deprotection and functionalization to X as desired in the final product of formula (1). In addition, X' may have the stereochemistry is as desired for X in the final product of formula (1).

For example, an appropriate compound of structure 2a is contacted with an appropriate piperidine of formula 3 or salt thereof to give a compound of formula (1) or a protected compound of formula (1). The reaction is carried out in a suitable substantially anhydrous solvent, such as tetrahydrofuran, pyridine, acetonitrile, toluene, or dimethylformamide using from 1.0 to 6.0 molar equivalents of a suitable base, such as triethylamine, pyridine, or N,N-diisopropylethylamine. When a salt of an appropriate piperidine of formula 3 is used, an additional molar excess of a suitable base is used. The reaction may be facilitated by the addition of a catalytic amount, about 0.1 to 0.5 molar equivalents, of an iodide salt, such as sodium iodide or potassium iodide. The reaction is generally carried out at temperatures of from ambient temperature to the refluxing temperature of the solvent. Generally, the reactions require 1 to 72 hours. The product can be isolated and purified by techniques well known in the art, such as extraction, evaporation, trituration, chromatography, and recrystallization.

Alternately, the reaction is carried out in a suitable mixed solvent, such as toluene/water mixtures, ethyl acetate/water mixtures, or tetrahydrofuran/water mixtures, using from 1.0 to 6.0 molar equivalents of a suitable base, such as sodium hydroxide, potassium hydroxide, sodium carbonate, sodium bicarbonate, potassium carbonate, or potassium bicarbonate. As above, when a salt of an appropriate piperidine of formula 3 is used, an additional molar excess of a suitable base is used. The reaction may be facilitated by the addition of a catalytic amount, about 0.1 to 0.5 molar equivalents, of an iodide salt, such as sodium iodide or potassium iodide. The reaction is generally carried out at temperatures of from ambient temperature to the refluxing temperature of the mixed solvent. Generally, the reactions require 1 to 150 hours. The product can be isolated and purified by techniques well known in the art, such as extraction, evaporation, trituration, chromatography, and recrystallization.

In Reaction Scheme A, optional step 3, a protected compound of formula (1) is deprotected or deprotected and functionalized to give a compound of formula (1). A deprotection reaction, such as deprotection of a carboxy or hydroxy protecting group utilizing suitable protecting groups such as those described in *Protecting Groups in Organic Synthesis* by T. Greene is well known and appreciated in the art. Deprotection and functionalization includes hydrolysis of esters, formation of esters, transesterification, formation of activated intermediates, and the formation of amides using an appropriate carboxy substituted cyclic amines as described in Reaction Scheme C, step 3. As is appreciated in the art, such compounds formula (1) prepared by functionalization after deprotection of X' may require further deprotection to give the final product of formula (1).

In addition, pharmaceutically acceptable salts of a compound of formula (1) are readily prepared from compounds of formula (1) by methods and techniques well known and appreciated in the art.

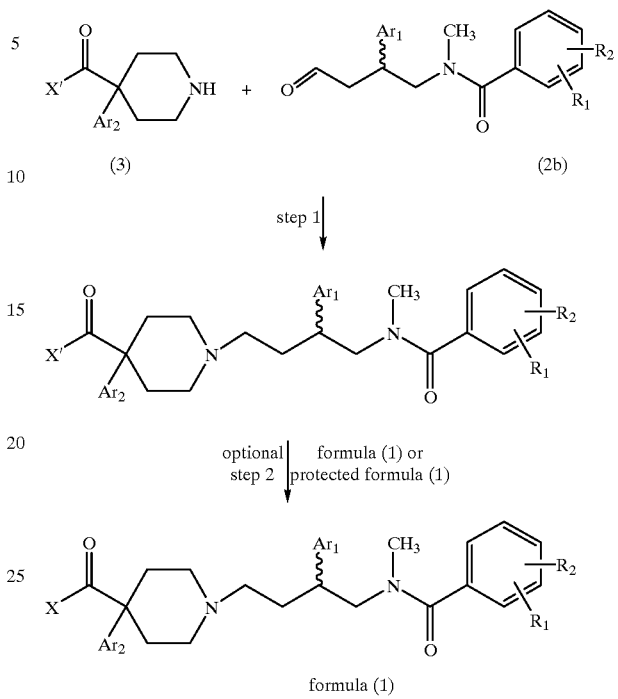

Reaction Scheme A.2

In Reaction Scheme A.2, step 1, an appropriate aldehyde of structure 2b reacts in an reductive amination with an appropriate piperidine of structure 3 or a salt thereof to give a protected compound of formula (1) or a compound of formula (1). Such reductive animation reactions are well known in the art, see *Bioorganic & Medicinal Chemistry Letters*, 3, 319–322 (1993) and *J. Am. Chem. Soc.*, 93 2897–2904 (1971).

An appropriate aldehyde of structure 2b is one in which the stereochemistry is as desired in the final product of formula (1) and $R_1$, $R_2$, and $Ar_1$ are as desired in the final product of formula (1). Alternately, an appropriate aldehyde of structure 2b can be one in which the stereochemistry gives rise after resolution to stereochemistry as desired in the final product of formula (1) and $R_1$, $R_2$, and $Ar_1$ are as desired in the final product of formula (1). An appropriate aldehyde of structure 2b can also be one in which the stereochemistry and $R_1$ and $R_2$ are as desired in the final product of formula (1) and $Ar_1$ gives rise upon deprotection to $Ar_1$ as desired in the final product of formula (1). Alternately, an appropriate aldehyde of structure 2b can also be one in which the stereochemistry gives rise after resolution to stereochemistry as desired in the final product of formula (1), $R_1$ and $R_2$ are as desired in the final product of formula (1), and $Ar_1$ gives rise upon deprotection to $Ar_1$ as desired in the final product of formula (1).

An appropriate aldehyde of structure 2b can be prepared from a homologous alkene by formation of the cis-diol followed by oxidative cleavage, as described in *Bioorganic & Medicinal Chemistry Letters*, 3, 319–322 (1993) or by methods analogous thereto, such as described in *J. Am. Chem. Soc.*, 104, 1737 (1982) and *Tet.*, 44, 5525 (1988) or by the action of ozone on a homologous alkene by methods well known in the art. An appropriate aldehyde of structure 2b can be prepared by oxidation of an alcohol of structure 2, such as by the method of Swern which is well known and appreciated in the art. An appropriate piperidine of structure 3 or salt thereof is one as described in Reaction Scheme A.1, step 2.

For example, an appropriate aldehyde of structure 2b is contacted with an appropriate piperidine compound of structure 3 or salt thereof to give a protected compound of formula (1) or a compound of formula (1). The reaction is carried out in a suitable solvent, such as methanol, ethanol, tetrahydrofuran, or mixtures of methanol or ethanol and tetrahydrofuran. The reaction may be carried out in the presence of a drying agent, such as sodium sulfate or molecular sieves. The reaction is carried out in the presence of from 1.0 to 6.0 molar equivalents of a suitable reducing agent, such as, sodium borohydride or sodium cyanoborohydride with sodium cyanoborohydride being preferred. It may be advantageous to allow Schiff base formation to proceed before addition of the suitable reducing agent. The reaction is generally carried out at temperatures of from 0° C. to the refluxing temperature of the solvent. Generally, the reactions require 1 to 72 hours. The product can be isolated and purified by techniques well known in the art, such as filtration, extraction, evaporation, trituration, chromatography, and recrystallization.

In Reaction Scheme A.2, optional step 2, a protected compound of formula (1) is deprotected or deprotected and functionalized to give a compound of formula (1) as described in Reaction Scheme A.1, optional step 3.

In addition, pharmaceutically acceptable salts of a compound of formula (1) are readily prepared from compounds of formula (1) by methods and techniques well known and appreciated in the art.

A general synthetic procedure for preparing the alcohols of structure 2 is set forth in Reaction Scheme B. The reagents and starting materials in Reaction Scheme B are readily available to one of ordinary skill in the art. In Scheme B, all substituents, unless otherwise indicated, are as previously defined.

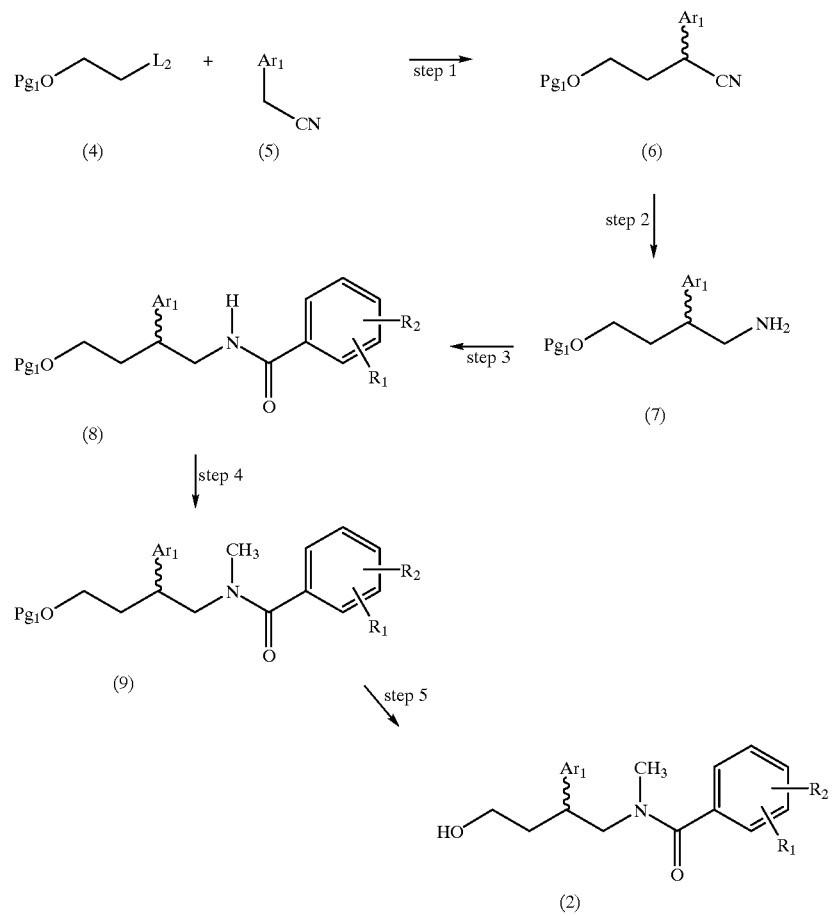

Reaction Scheme B

In Reaction Scheme B. step 1, an appropriate nitrile of structure 5 is alkylated with an appropriate protected alcohol of structure 4 to give an 4-(protected-hydroxy)butyronitrile of structure 6.

An appropriate nitrile of structure 5 is one in which $Ar_1$ is as desired in the final product of formula (1) or $Ar_1$ gives rise after deprotection to $Ar_1$ as desired in the final product of formula (1). An appropriate protected alcohol of structure 4 is one in which the leaving group, $L_2$, can be displaced by an anion derived from an appropriate nitrile of structure 5. Suitable leaving groups include but are not limited to chloro, bromo, iodo, and mesylate with bromo and iodo being preferred. The selection and use of a suitable hydroxy protecting group, Pg₁, such as those described in *Protecting Groups in Organic Synthesis* by T. Greene are well known and appreciated in the art. The use of tetrahydropyran-2-yl and t-butyldimethylsilyl hydroxy protecting groups are generally preferred.

For example, the appropriate nitrile of structure 5 is contacted with 0.8 to 1.2 molar equivalents of the appropriate protected alcohol of structure 4 under phase transfer catalysis conditions. The reaction is carried out in the presence of a 2 to 10 fold molar excess of a suitable base, such as sodium hydroxide or potassium hydroxide. The reaction is carried out in a solvent, such as water, ethyl acetate/water mixtures, dichloromethane/water mixtures, or tetrahydrofuran/water mixtures. The reaction is carried out in the presence of a suitable phase transfer catalyst, such as benzyltriethylammonium chloride, benzyltriethylammonium bromide, benzyltriethylammonium iodide, benzyltrimethylammonium chloride, benzyltributylammonium chloride, tetrabutylammonium chloride, tetrabutylammonium bromide, tetrabutylammonium iodide, tetrabutylammonium hydrogen sulfate, and the like. The reaction is generally carried out at temperatures of from −20° C. to 60° C. Generally, the reactions require 1 to 72 hours. The product can be isolated and purified by techniques well known in the art, such as extraction, evaporation, trituration, chromatography, and recrystallization.

Alternately, for example, the appropriate nitrile of structure 5 is contacted with 1.0 to 1.2 molar equivalents of the appropriate protected alcohol of structure 4. The reaction is carried out in the presence of an equimolar amount of a suitable base, such as sodium hydride, sodium bis(trimethylsilyl)amide, potassium bis(trimethylsilyl)amide, potassium t-butoxide, s-butyl lithium, and lithium diisopropylamide, The reaction is carried out in a solvent, such as dimethylformamide or tetrahydrofuran. The reaction is generally carried out at temperatures of from −78° C. to 0° C. Generally, the reactions require 1 to 72 hours. The product can be isolated and purified by techniques well known in the art, such as extraction, evaporation, distillation, trituration, chromatography, and recrystallization.

In Reaction Scheme B, step 2, the 4-(protected-hydroxy)butyronitrile of structure 6 is reduced to give an amino compound of structure 7.

For example, the 4-(protected-hydroxy)butyronitrile of structure 6 is contacted with an excess of an appropriate reducing agent, such as sodium borohydride in the presence of cobalt (II) chloride hexahydrate or hydrogen in the presence of a suitable catalyst, such as Raney nickel or platinum oxide. For compounds of structure 6 in which Ar₁ is thienyl and pyridyl, sodium borohydride in the presence of cobalt (II) chloride hexahydrate is preferred.

When sodium borohydride in the presence of cobalt chloride is used, the reaction is carried out in a suitable solvent, such as methanol, or ethanol. The reaction is generally carried out at temperatures of from 0° C. to 50° C. Generally, the reactions require 1 to 72 hours. The product can be isolated by techniques well known in the art, such as extraction with aqueous acid, evaporation, trituration, distillation, chromatography, and recrystallization.

When Raney nickel is used, the reaction is carried out in a suitable solvent containing ammonia, such as ethanol/aqueous ammonium hydroxide or methanol/aqueous ammonium hydroxide. The reaction is generally carried out at temperatures of from ambient temperature to 70° C. The reaction is carried out with hydrogen at pressures of from 15 psi to 120 psi in an apparatus designed for carrying out reactions under pressure, such as a Parr hydrogenation apparatus. The product can be isolated by carefully removing the catalyst by filtration and evaporation. The product can be purified by extraction, evaporation, trituration, chromatography, and recrystallization.

When platinum oxide is used, the reaction is carried out in a suitable solvent such as ethanol, methanol, chloroform, ethanol/chloroform mixtures, or methanol/chloroform mixtures. The reaction is generally carried out at temperatures of from ambient temperature to 50° C. The reaction is carried out with hydrogen at pressures of from 15 psi to 120 psi in an apparatus designed for carrying out reactions under pressure, such as a Parr hydrogenation apparatus. Generally, an amine intermediate is obtained under these conditions and is isolated by carefully removing the catalyst by filtration and evaporation. Generally, the reaction requires 8 to 48 hours. The product can be purified by extraction, evaporation, trituration, chromatography, and recrystallization.

In Reaction Scheme B, step 3, the amino compound of structure 7 is benzoylated with an appropriate benzoylating agent to give a benzamide of structure 8. An appropriate benzoylating agent is an agent capable of transferring a benzoyl group or substituted benzoyl group, such as a benzoyl halide, substituted benzoyl halide, benzoyl anhydride, substituted benzoyl anhydride, benzoyl mixed anhydride, or substituted benzoyl mixed anhydride to give a benzamide of structure 8. An appropriate benzoylating agent gives a benzamide of structure 8 in which R₁ and R₂ are as desired in the final product of formula (1).

For example, the amino compound of structure 7 is contacted with 1 to 1.5 molar equivalents of an appropriate benzoylating agent. The reaction is carried out in a suitable solvent, such as dichloromethane, tetrahydrofuran, acetonitrile, dimethylformamide, or pyridine. The reaction is carried out in the presence of a base, such as sodium carbonate, sodium bicarbonate, triethylamine, N-methylmorpholine, N,N-diisopropylethylamine, or pyridine. The reaction is generally carried out at temperatures of from −20° C. to 50° C. Generally, the reactions require 1 to 6 hours. The product can be isolated and purified by techniques well known in the art, such as extraction, evaporation, trituration, chromatography, and recrystallization.

Alternately, for example, the amino compound of structure 7 is contacted with 1 to 1.5 molar equivalents of an appropriate benzoylating agent under Schotten-Baumann conditions. The reaction is carried out in a suitable solvent, such as ethyl acetate/water mixtures, acetone/water mixtures, tetrahydrofuran/water mixtures, or dichloromethane/water mixtures. The reaction is carried out in the presence of a base, such as sodium carbonate, sodium bicarbonate, potassium carbonate, potassium bicarbonate, or sodium hydroxide. The reaction is generally carried out at temperatures of from 0° C. to the refluxing temperature of the solvent. Generally, the reactions require 1 to 6 hours. The product can be isolated and purified by techniques well known in the art, such as extraction, evaporation, trituration, chromatography, and recrystallization.

In Reaction Scheme B, step 4, a benzamide of structure 8 is methylated with an appropriate methylating agent to give a N-methylbenzamide of structure 9. An appropriate methylating agent is one that transfers a methyl to a benzamide of structure 8, including iodomethane, bromomethane, dimethylsulfate, trimethyloxonium tetrafluoroborate, and the like.

For example, a benzamide of structure 8 is contacted with 1 to 4 molar equivalents of the appropriate methylating agent. The reaction is carried out in the presence of from 1 to 4 molar equivalents of a suitable base, such as sodium hydride, sodium bis(trimethylsilyl)amide, potassium t-butoxide, n-butyl lithium, sec-butyl lithium, and lithium diisopropylamide with sodium hydride and sodium bis(trimethylsilyl)amide being preferred. The reaction is carried out in a solvent, such as dimethylformamide or tetrahydrofuran. The reaction is generally carried out at temperatures of from −20° C to 60° C. Generally, the reactions require 1 to 72 hours. The product can be isolated and purified by techniques well known in the art, such as extraction, evaporation, trituration, chromatography, and recrystallization.

In Reaction Scheme B, step 5, the N-methylbenzamide of structure 9 is deprotected to give an alcohol of structure 2. A deprotection reaction, such as the removal of hydroxy protecting groups utilizing suitable protecting groups such as those described in *Protecting Groups in Organic Synthesis* by T. Greene is well known and appreciated in the art.

Reaction Scheme C sets forth a general synthetic procedure for preparing piperidine compounds of structure 3 used as starting materials in Reaction Schemes A.1 and A.2. The reagents and starting materials in Reaction Scheme C are readily available to one of ordinary skill in the art. In Scheme C, all substituents, unless otherwise indicated, are as previously defined.

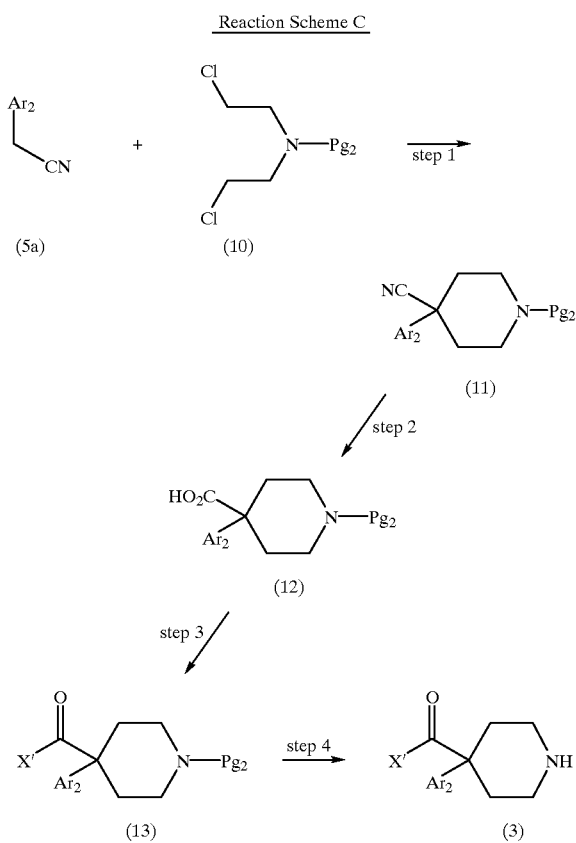

Reaction Scheme C

In Reaction Scheme C, step 1, an appropriate protected bis-(2-chloroethyl)-amine of formula 10 is alkylated with an appropriate aryl-acetonitrile of formula 5a to give a protected 4-aryl-4-cyanopiperidine of formula 11. An appropriate protected bis-(2-chloroethyl)-amine of formula 10 is one in which the protecting group, $Pg_2$, may be $C_1$–$C_4$ alkyl, benzyl, substituted benzyl, p-toluenesulfonyl, benzenesulfonyl, or a carbamate, such as t-butoxycarbonyl or ethoxycarbonyl. An appropriate aryl-acetonitrile of formula 5a is one in which $Ar_2$ is as desired in the final product of formula (1). Alkylation of this type are well known and appreciated in the art, see T. Cammack and P. C. Reeves, *J. Heterocyclic Chem.* 12, 73–75 (1986) and C. V. Bercz and R. D. Ice, *J. Pharmaceutical Sci.*, 10, 1316–1317 (1972).

For example, an appropriate protected bis-(2-chloroethyl)-amine of formula 10 is contacted with an appropriate aryl-acetonitrile of formula 5a. The reaction is carried out in the presence of a base, such as sodium amide, sodium hydride, sodium bis(trimethylsilyl)amide, potassium t-butoxide, and lithium diisopropylamide. The reaction is carried out in a solvent, such as dimethyl sulfoxide or tetrahydrofuran. The reaction can be carried out in the presence of 0.01 to 0.5 molar equivalents of a suitable catalyst, such as sodium iodide or potassium iodide. The reaction is generally carried out at temperatures of from 0° C to 80° C. Generally, the reactions require 1 to 72 hours. The product can be isolated and purified by techniques well known in the art, such as extraction, evaporation, trituration, chromatography, and recrystallization.

Alternately, for example, an appropriate protected bis-(2-chloroethyl)-amine of formula 10 is contacted with an appropriate aryl-acetonitrile of formula 5a under phase transfer conditions. The reaction may be carried out in water or in a solvent system consisting of an organic phase and an aqueous phase. The reaction is carried out in the presence of a hydroxide base, such as sodium hydroxide or potassium hydroxide. The reaction is carried out in the presence of a suitable catalyst including quaternary ammonium and phosphonium salts, such as tetrabutylammonium bromide, tetrabutylammonium hydrogen sulfate, hexadecyltributyl phosphonium bromide, benzyltrimethylammonium chloride, and the like. The reaction is vigorously stirred and is generally carried out at temperatures of between 0° C. and 100° C. Generally, the reactions require 1 to 24 hours. The product can be isolated and purified by techniques well known in the art, such as extraction, evaporation, trituration, chromatography, and recrystallization.

In Reaction Scheme C, step 2, a 4-aryl-4-cyanopiperidine of formula 11 is hydrolyzed to give a 4-aryl-piperidine-4-carboxylic acid of formula 12. The hydrolysis of nitriles to acids may be carried out under acidic or basic conditions as is well known and appreciated in the art. The selection and use of hydrolysis conditions which are compatible with the protecting group, $Pg_2$, is well known and appreciated in the art. As appreciated by those skilled in the art, the removal of the amine protecting group $Pg_2$ in either before or after step 2 may be required.

For example, when $Pg_2$ is benzyl the protecting group may be removed to facilitate the hydrolysis of the nitrile and then reintroduced after hydrolysis. If removed, reintroduction of the protecting group $Pg_2$, either as benzyl or another protecting group, after hydrolysis gives a 4-aryl-piperidine-4-carboxylic acid of formula 12.

Alternately, the protecting group used in Reaction Scheme C, steps 1 and 2, may be removed and replaced by another protecting group to facilitate deprotection of compound 13, in Reaction Scheme C, step 4. The introduction of amine protecting groups is well known and appreciated in the art and taught in *Protecting Groups in Organic Synthesis* by T. Greene, Wiley-Interscience (1981).

In addition, as is readily understood by those skilled in the art, 4-aryl-piperidine-4-carboxylic acid of formula 12 can be prepared from 4-aryl-4-cyanopiperidine of formula 11 by further hydrolysis of a 4-aryl-piperidine-4-carboxylic acid amide prepared by partial hydrolysis of a 4-aryl-4-cyanopiperidine of formula 11 to give such primary amides.

For example, an appropriate a 4-aryl-4-cyanopiperidine of formula 11 is contacted with basic hydrogen peroxide to give a 4-aryl-4-carboxylic acid amide-piperidine or 4-aryl-4-carboxylic acid amide-piperidine N-oxide. The use of basic hydrogen peroxide for the hydrolysis of nitriles to carboxamides is well know and appreciated in the art. *Reagents for Organic Synthesis*, Fieser and Fieser, John Wiley and Sons, Inc. (1967). Alkali metal hydroxides, such as sodium hydroxide or potassium hydroxide are suitable bases for this reaction. The reaction is carried out in a suitable solvent, such as water, ethanol, methanol, water/ethanol mixtures, or water/methanol mixtures. The reaction is carried out at temperatures of from 0° C. to the refluxing temperature of the suitable solvent. Generally, the reaction requires from about 4 hours to 4 days. The product can be isolated and purified by techniques well known in the art, such as extraction, evaporation, trituration, chromatography, and recrystallization.

When such an amide is obtained it may deprotected to give a 4-aryl-piperidine-4-carboxylic acid amide. When a 4-aryl-4-carboxylic acid amide-piperidine N-oxide is obtained it is reduced and may be deprotected to give a 4-aryl-piperidine-4-carboxylic acid amide. As is well appreciated in the art a 4-aryl-piperidine-4-carboxylic acid amide can be further hydrolyzed under acidic or basic conditions to give a 4-aryl-piperidine-4-carboxylic acid. As described above, if removed, reintroduction of the protecting group $Pg_2$, either as benzyl or another protecting group, after hydrolysis gives a 4-aryl-piperidine-4-carboxylic acid of formula 12.

In Reaction Scheme C, step 3, the 4-aryl-piperidine-4-carboxylic acid of formula 12 undergoes an anidation reaction with an appropriate carboxy substituted cyclic amine to give a protected 4-aryl-4-carboxamido-piperidine of formula 13. An appropriate carboxy substituted cyclic amine is one that gives the group X' which is the X as desired in the final product of formula (1) or gives rise after deprotection or deprotection and functionalization to a group X as desired in the final product of formula (1). Illustrative examples of such appropriate carboxy substituted cyclic amines include, 4-carboethoxypiperidine, 3-carboethoxypiperidine, 2-carboethoxy piperidine, 4-carbomethoxypiperidine, 3-carbomethoxypiperidine, 2-carbomethoxypiperidine, 4-carbo-n-propyloxypiperidine, 4-carbo-t-butyloxypiperidine, 3-carboethoxypyrrolidine, 2-carboethoxypyrrolidine, 3-carbomethoxypyrrolidine, 2-carbomethoxypyrrolidine, 2-carboethoxymorpholine, 3-carboethoxymorpholine, 4-carbomethoxymethylpiperazine, 4-carboethoxymethylpiperazine, 4-carboethoxyethylpiperazine, 4-carboethoxypropylpiperazine, 4-carboethoxybutylpiperazine, 4-carbo-n-propyloxymethyl piperazine, 4-carboisopropyloxymethylpiperazine, 4-carbo-n-butyloxymethylpiperazine, 4-carbo-t-butyloxymethylpiperazine, and the like. As is appreciated by those skilled in the art, the carboxy function of an appropriate carboxy substituted cyclic amine can be further deprotected or functionalized after deprotection as desired to give X as desired in the final compound of formula (1). Such deprotection or functionalization includes hydrolysis of esters, formation of esters, and transesterification.

For example, an amidation reaction may proceed through the acid of formula 12 or the acid function of a compound of formula 12 may be first converted to an activated intermediate; such as an anhydride; a mixed anhydride of substituted phosphoric acid, such as dialkylphosphoric acid, diphenylphosphoric acid, halophosphoric acid; of aliphatic carboxylic acid, such as formic acid, acetic acid, propionic acid, butyric acid, isobutyric acid, pivalic acid, 2-ethylbutyric acid, trichloroacetic acid, trifluoroacetic acid, and the like; an activated ester, such as phenol ester, p-nitrophenol ester, 2,4-dinitrophenol ester, pentafluorophenol ester, N-hydroxysuccinimide ester, N-hydroxyphthalimide ester, 1-hydroxybenztriazole ester, and the like; activated amide, such as imidazole, dimethylpyrazole, triazole, or tetrazole; or the intermediate formed in the presence of coupling agents, such as dicyclohexylcarbodiimide or 1-(3-dimethylaminopropyl)-3-ethylcarbodiimide. Activated intermediates may be prepared and used directly, or are prepared and isolated before the addition of an appropriate carboxy substituted cyclic amine. Alternately, activated intermediates may be prepared isolated and purified before the addition of an appropriate carboxy substituted cyclic amine. The use and formation of activated intermediates is well known and appreciated in the art.

For example, an acid compound of formula 12 is contacted with a slight molar excess of an appropriate carboxy substituted cyclic amine or a salt of an appropriate carboxy substituted cyclic amine and 1-hydroxybenzotriazole hydrate in the presence of a slight molar excess of a coupling agent, such as dicyclohexylcarbodiimide or 1-(3-dimethyaminopropyl)-3-ethylcarbodiimide. The reaction is carried out in the presence of a suitable base, such as N,N-diisopropylethylamine, N-methylmorpholine, or triethylamine, and if the salt of an appropriate carboxy substituted cyclic amine is used an about an additional molar amount of a suitable base is added. The reaction is carried out in a suitable solvent, such as dichloromethane, chloroform, or dimethylformamide. The product can be isolated and purified by techniques well known in the art, such as extraction, evaporation, chromatography, and recrystallization.

Alternatively, for example, an acid of formula 12 is contacted with 1.2 to 1.7 equivalents of a suitable base, such as N-methylmorpholine, in a suitable solvent, such as tetrahydrofuran. As above, if the salt of an appropriate carboxy substituted cyclic amine is used an about an additional molar amount of a suitable base is added. The reaction mixture is cooled to a temperature of between −50° C. and 0° C. with −25° C. to -20° C. being preferred, before the addition of 1.2 to 1.7 equivalents of isobutyl chloroformate. The reaction is allowed to stir for 30 minutes to 3 hours to allow for the formation of the mixed anhydride, an activated intermediate. While maintaining the temperature at between −50° C. and 0° C. an appropriate carboxy substituted cyclic amine is added. The reaction may, after the addition of amine is complete, be warmed to room temperature. Generally, the reaction requires from 2 to 48 hours. The product can be isolated and purified by techniques well known in the art, such as extraction, evaporation, chromatography, and recrystallization.

In Reaction Scheme C, step 4, a protected 4-aryl-4-carboxamido-piperidine of formula 13 is deprotected to give a piperidine of formula 3. The removal of amine protecting groups is well known and appreciated in the art and is described in *Protecting Groups in Organic Synthesis* by T. Greene, Wiley-Interscience (1981).

The following examples and preparations present typical syntheses of the compounds of formula (1). These examples are understood to be illustrative only and are not intended to limit the scope of the invention in any way.

PREPARATION 1

2-Methoxy-5-(1H-tetrazol-1-yl)benzoyl chloride

Combine 2-hydroxy-5-nitrobenzoic acid (21.5 g, 117 mmol), potassium carbonate (162.3 g, 1.174 mol), and methyl iodide (136.8 g, 96.4 mmol) in acetone (500 mL). Heat to reflux. After 18 hours, cool the reaction mixture to ambient temperature and add methyl iodide (136.8 g, 96.4 mmol). Again, heat to reflux. After 56 hours, cool the reaction mixture to ambient temperature and filter, rinse with acetone, and evaporate the filtrate in vacuo to give a residue. Recrystallize the residue from ethanol to give a second residue. Combine the second residue and chloroform (about 100 mL), filter, and evaporate the filtrate in vacuo to give methyl 2-methoxy-5-nitrobenzoate. $R_f$=0.38 (silica gel, ethyl acetate/hexane 1/1).

Combine methyl 2-methoxy-5-nitrobenzoate (13.3 g, 63 mmol) and methanol. Add 5% palladium-on-carbon (0.66 g). Hydrogenate on a pressure apparatus at 50 psi. After 17 hours, filter through celite to remove the catalyst and evaporate the filtrate in vacuo to give a residue. Combine the residue and dichloromethane and extract with water. Dry the organic layer over $Na_2SO_4$, filter, and evaporate in vacuo to give methyl 2-methoxy-5-aminobenzoate. $R_f$=0.18 (silica gel, ethyl acetate/methanol 1/1). Elemental Analysis calculated for $C_9H_{11}NO_3$: C, 59.66; H, 6.12; N, 7.73. Found: C, 59.44; H, 6.04; N, 7.62.

Combine methyl 2-methoxy-5-aminobenzoate (3.94 g, 21.7 mmol) and triethyl orthoformate (12.8 g, 86.7 mmol) in glacial acetic acid (20 mL). After 20 hours, concentrate the reaction mixture in vacuo to remove ethanol. Add glacial acetic acid (20 mL) and sodium azide (5.64 g, 86.7 mmol). Heat to 70° C. After 1 hour, add glacial acetic acid (10 mL) and continue to heat to 70° C. After an additional hour, cool the reaction mixture to ambient temperature, dilute with water (500 mL). Collect the solid by filtration, rinse with water, and dry to give methyl 2-methoxy-5-(1H-tetrazol-1-yl)benzoate.

Combine methyl 2-methoxy-5-(1H-tetrazol-1-yl)benzoate (2.86 g, 12.2 mmol) and a 1 M aqueous solution of sodium hydroxide (13.43 mL, 13.43 mmol) in methanol/water (100 mL, 5:1 vol./vol.). Heat to reflux. After 4 hours, concentrate in vacuo to remove most of the methanol, add water (50 mL), and adjust the pH to about 4 using a 1 M aqueous hydrochloric acid solution. Evaporate in vacuo to give a solid, slurry the solid with water, filter, and dry to give 2-methoxy-5-(1H-tetrazol-1-yl)benzoic acid.

Alternately, combine methyl 2-methoxy-5-(1H-tetrazol-1-yl)benzoate (13.3 g, 56.8 mmol) and methanol (150 mL). Add 1 M aqueous solution of sodium hydroxide (62.5 mL, 62.5 mmol). Heat to reflux. After 30 minutes, add methanol (50 mL) and water (50 mL) and continue the heat at reflux. After 1 hour, concentrate in vacuo to remove most of the solvent. Adjust the pH to about 1 to 2 using a 1 M aqueous hydrochloric acid solution to give a solid. Collect the solid by filtration, rinse with water, and dry to give 2-methoxy-5-(1H-tetrazol-1-yl)benzoic acid.

Combine 2-methoxy-5-(1H-tetrazol-1-yl)benzoic acid (1.2 g, 5.5 mmol) and dichloromethane (40 mL). Add dropwise oxalyl chloride (0.72 mL, 8.25 mmol) followed by dimethylformamide (3 drops). After 4 hours, evaporate in vacuo and dry to give the title compound.

PREPARATION 2

3,4-Dichlorophenylacetyl chloride

Combine 3,4-dichlorophenyl acetic acid (9 g, 44 mmol) and dichloromethane (100 ml). Add dropwise a solution of oxalyl chloride (30 ml, 2 M, 60 mmol) in dichloromethane. Add dimethylformamide (6 drops). After 2.5 hours, evaporate in vacuo to give a residue, twice had dichloromethane and evaporate in vacuo to give the title compound which is used without further purification.

PREPARATION 3

3,4-Dichlorophenylacetic acid trimethylacetyl ester

Combine 3,4-dichlorophenyl acetic acid (31.5 g, 154 mmol) and triethylamine (25.7 ml, 184 mmol) and tetrahydrofuran (300 ml). Cool in a dry-ice/acetone bath. Add trimethylacetyl chloride (18.5 grams, 154 mmol) and tetrahydrofuran (200 ml). Warm to ambient temperature to give the title compound in solution.

PREPARATION 4

(S)-N-Methyl-N-(2-(3,4-dichlorophenyl)-4-oxobutyl)-2-methoxy-5-(1H-tetrazol-1-yl)benzamide Combine (S)-4-benzyl-2-oxazolidinone (2.6 g, 34 mmol) and tetrahydrofuran (80 mL). Cool in a dry-ice/acetone bath. Add dropwise a solution of n-butyl lithium (13.5 mL, 2.5 M, 27 mmol). After 15 minutes, slowly add a solution of 3,4-dichlorophenylacetyl chloride (9.4 g, 44 mmol) in tetrahydrofuran (20 mL). After 20 minutes, warm to ambient temperature. After 2 hours, dilute the reaction mixture with diethyl ether and add a saturated aqueous sodium bicarbonate solution. Separate the layers and extract the organic layer with a saturated ammonium chloride solution and then water. Dry over $MgSO_4$, filter, and evaporate in vacuo to give a residue. Chromatograph the residue on silica gel eluting sequentially with 5% ethyl acetate/hexane, 10% ethyl acetate/hexane, and 15% ethyl acetate/hexane. Combine the product containing fraction to give a residue. Rechromatograph the residue on silica gel eluting sequentially with 5% ethyl is acetate/hexane, 10% ethyl acetate/hexane, 15% ethyl acetate/hexane, and 20% ethyl acetate/hexane to give a residue. Recrytallize from diethyl ether/hexane to give (S)-4-benzyl-3-(3,4-dichlorophenyl)acetyl-2-oxazolidinone: mp; 70.5–71.5° C. $R_f$=0.75 (silica gel, 50% ethyl acetate/hexane).

Alternately, combine (S)-benzyl-2-oxazolidinone (25 g, 140 mmol) and tetrahydrofuran (250 ml). Add triphenylmethane (30 mg) as an indicator. Cool to about −40° C. Add n-butyl lithium (about 56 ml, 1 M in hexane, 140 mmol) until an orange color persists. After 30 minutes, cool in a dry-ice/acetone bath the a solution of 3,4-dichlorophenylacetic acid trimethylacetyl ester as obtained in Preparation 3 and add by cannula the solution of lithio (S)-benzyl-2-oxazolidinone obtained above. When the addition is complete warm to ambient temperature. After 18 hours, partition the reaction mixture between diethyl ether and a saturated aqueous sodium bicarbonate solution. Separate the layers and dry the organic layer over $MgSO_4$, filter, and evaporate in vacuo to give a residue. Chromatograph the residue on silica gel eluting sequentially is with 5% ethyl acetate/hexane and 10% ethyl acetate/hexane to give (S)-4-benzyl-3-(3,4-dichlorophenyl)acetyl-2-oxazolidinone.

Combine (S)-4-benzyl-3-(3,4-dichlorophenyl)acetyl-2-oxazolidinone (13.9 g, 38.2 mmol) and tetrahydrofuran (140 mL). Cool in a dry-ice/acetone bath. Add dropwise a solution of sodium bis(trimethylsilyl)amide (42 mL, 1.0 M in tetrahydrofuran, 42 mmol). After 30 minutes, add allyl iodide (19 g, 114.5 mmol) and then replace the bath with a dry-ice/carbon tetrachloride bath. After 1 hour, partition the reaction the reaction mixture between a saturated aqueous ammonium chloride solution and diethyl ether. Separate the layer, dry the organic layer over MgSO$_4$, filter, and evaporate in vacuo to give a residue. Chromatograph the residue on silica gel eluting with 5% ethyl acetate/hexane to give (S)-4-benzyl-3-(2-(3,4-dichlorophenyl)pent-4-enoyl)-2-oxazolidinone: R$_f$=0.50 (silica gel, 20% ethyl acetate/hexane).

Combine (S)-4-benzyl-3-(2-(3,4-dichlorophenyl)pent-4-enoyl)-2-oxazolidinone (13.7 g, 34.0 mol), tetrahydrofuran (300 mL), and water (60 mL). Cool in an ice bath. Add lithium hydroxide hydrate (1.7 g, 71.0 mmol) and an aqueous solution of hydrogen peroxide (12 mL, 30% 140 mmol). After 2 hours, quench by the addition of an aqueous 10% sodium thiosulfate solution (100 mL). Add an aqueous 1 M sodium hydroxide solution and extract twice with diethyl ether. Cool the aqueous layer in an ice bath, acidify with an aqueous concentrated hydrochloric acid solution (about 20 mL), and extract twice with dichloromethane. Combine the organic layers, dry over MgSO$_4$, filter, and evaporate in vacuo to give (S)-2-(3,4-dichlorophenyl)pent-4-enoic acid.

Combine (S)-2-(3,4-dichlorophenyl)pent-4-enoic acid (6.55 g, 26.7 mmol), dichloromethane (10 mL), and dimethylformamide (2 drops). Add a solution of oxalyl chloride (16 mL, 2 M, 32 mmol) in dichloromethane. After 2 hours, evaporate in vacuo to give (S)-2-(3,4-dichlorophenyl)pent-4-enoyl chloride. Combine with toluene (20 mL) and slowly add, with vigorous stirring, to a cooled (ice bath) aqueous solution of methylamine (4 mL, 40%) while maintaining the temperature of the reaction mixture at less than 10° C. When the addition is complete add toluene (40 mL). After 1 hour, partition the reaction mixture between water and dichloromethane. Separate the layers, extract the organic layer with a saturated aqueous sodium bicarbonate solution, dry over MgSO4, filter, and evaporate in vacuo to give a residue. Chromatograph the residue on silica gel eluting sequentially with 10% ethyl acetate/hexane, 20% ethyl acetate/hexane, and 30% ethyl acetate/hexane to give (S)-2-(3,4-dichlorophenyl)pent-4-enoic acid, N-methyl amide: R$_f$=0.50 (silica gel, 50% ethyl acetate/hexane).

Cool a solution of lithium aluminum hydride (42.6 mL, 1.0 M in tetrahydrofuran, 42.6 mmol) to about −10° C. Add dropwise a solution of sulfuric acid (2.1 g) in tetrahydrofuran (5 mL) while maintaining the temperature of the reaction mixture at less than 0° C. After 20 minutes, warm to ambient temperature. Add a solution of (S)-2-(3,4-dichlorophenyl)pent-4-enoic acid, N-methyl amide (4.8 g, 18.8 mmol) and tetrahydrofuran (25 mL). After the addition is complete, heat the reaction mixture abbot t 35° C. After 15 hours, cool in an ice bath and carefully quench by the addition of water (5 mL) and tetrahydrofuran (5 mL). Add tetrahydrofuran (60 mL) and filter, and evaporate the filtrate in vacuo to give a residue. Combine the residue and dichloromethane, extract with water, dry over MgSO$_4$, filter, and evaporate in vacuo to give a residue. Chromatograph the residue on silica gel eluting sequentially with 1% methanol/dichloromethane, 2% methanol/dichloromethane, 3% methanol/dichloromethane, and 4% methanol/dichloromethane to give (S)-N-methyl-(2-(3,4-dichlorophenyl)pent-4-enyl)amine: R$_f$=0.54 (silica gel, 9/1/0.1 dichloromethane/methanol/concentrated aqueous ammonia).

Combine 2-methoxy-5-(1H-tetrazol-1-yl)benzoyl chloride (3.97 g, 16.5 mmol) and sodium bicarbonate (5.33 g, 63.5 mmol) in acetone (100 mL). Add a solution of (S)-N-methyl-2-(3,4-dichlorophenyl)pent-4-enyl)amine (3.1 g, 12.7 mmol) in acetone (40) mL)/water (40 mL). Cool in an ice bath with vigorous stirring. After 18 hours, filter, rinse with ethyl acetate (250 mL). Separate the filtrate into layers and extract the organic layer with a saturated aqueous sodium bicarbonate solution. Dry the organic layer over MgSO4, filter, and evaporate in vacuo to give a residue. Chromatograph the residue on silica gel eluting with ethyl acetate to give (S)-N-methyl-N-(2-(3,4-dichlorophenyl)pent-4-enyl)-2-methoxy-5-(1H-tetrazol-1-yl)benzamide: R$_f$=0.43 (silica gel, 6% methanol/dichloromethane).

Combine (S)-N-methyl-N-(2-(3,4-dichlorophenyl)pent-4-enyl)-2-methoxy-5-(1H-tetrazol-1-yl)benzamide (5.12 g, 11.5 mmol), acetone/t-butanol/water (2/1/1, 120 mL), and a solution of N-methylmorpholine N-oxide (3.3 g 50% in water). Add a solution of osmium tetraoxide (4.4 g, 4% in water, 13.8 mmol). After 2 hours, evaporate in vacuo to remove most of the acetone and partition the evaporated reaction mixture between dichloromethane and an aqueous 10% solution of sodium thiosulfate. Separate the layers, extract the organic layer with brine, dry over MgSO$_4$, filter, and evaporate in vacuo to give a residue. Combine the residue and tetrahydrofuran/water (4/1 150 mL). Add sodium meta-periodate (2.95 g, 13.8 mmol). After 1.5 hours, filter the reaction mixture, rinse the solids with tetrahydrofuran, and evaporate the filtrate to remove most of the tetrahydrofuran. Dilute the evaporated reaction mixture with dichloromethane. Extract with water, dry over MgSO$_4$, filter, and evaporate in vacuo to give a residue. Chromatograph the residue on silica gel eluting sequentially with 1% methanol/dichloromethane, 2% methanol/dichloromethane, and 3% methanol/dichloromethane to give the title compound: R$_f$=0.20 (silica gel, 6% methanol/dichloromethane).

PREPARATION 5

4-Phenyl-4-((4-carboethoxymethylpiperazin-1-yl)carboxamido)piperidine hydriodic acid salt Combine 4-phenylpiperidine-4-carboxylic acid p-toluenesulfonic acid (97.5 g, 0.258 mol), N,N-diisopropylethylamine (55 mL, 0.316 mol), and dimethylformamide (900 mL). Add dropwise, a solution of di-t-butyl dicarbonate (65.0 g, 0.30 mol) in dimethylformamide (300 mL). After 20 hours, dilute the reaction mixture with diethyl ether and extract with three times with water and then with brine. Dry the organic layer over MgSO$_4$, filter, rinse the MgSO$_4$ with 5 dichloromethane. Evaporate in vacuo to give 1-t-butoxycarbonyl-4-phenyl-piperidine-4-carboxylic acid.

Combine 1-t-butoxycarbonyl-4-phenyl-piperidine-4-carboxylic acid (27.0 g, 88.5 mmol), N,N-diisopropylethylamine (34 mL, 0.195 mol), 4-carboethoxymethylpiperazine (5.8 g), and 1-hydroxybenzotriazole hydrate (13.2 g, 98 mmol) in dichloromethane (400 mL). Add 1-(3-dimethylaminopropyl)-3-ethylcarbodiimide hydrochloride (18.7 g, 87.5 mmol). After 20 hours, dilute the reaction mixture with dichloromethane and extract twice with water. Dry the organic layer over MgSO$_4$, filter, and evaporate in vacuo to give a residue. Chromatograph the residue on silica gel eluting sequentially with 20% ethyl acetate/hexane, ethyl acetate, 94/6 dichloromethane/methanol, and then 90/10 dichloromethane/methanol to give 1-t-butoxycarbonyl-4-phenyl-4-((4-carboethoxymethylpiperazin-1-yl))carboxamido) piperidine.

Combine 1-t-butoxycarbonyl-4-phenyl-4-((4-carboethoxymethylpiperazin-1-yl))carboxamido)piperidine (26.0 g, 56.7 mmol) and dichloromethane (40 mL). Add hydriodic acid (gas, 2.8 g). After 3 hours, evaporate in vacuo to give, after drying, the title compound.

Alternately, combine 1-t-butoxycarbonyl-4-phenyl-4-((4-carboethoxymethylpiperazin-1-yl))carboxamido)piperidine (10.0 g, 21.8 mmol) and ethanol (700 mL). Add an aqueous solution of hydriodic acid (57%, 6.1 mL, 45.75 mmol). After 2 hours, heat to reflux. After 19 hours, cool to ambient temperature and dilute the reaction mixture with diethyl ether (300 mL) to give a solid. Cool in an ice bath. After 1 hour, collect the solid by filtration, rinse with diethyl ether, and dry to give the title compound. Elemental Analysis calculated for $C_{20}H_{29}N_3O_3 \cdot 2HI$: C, 39.04; H, 5.08; N, 6.83; Found: C, 39.14; H, 5.38; N, 6.88.

EXAMPLE 1

(S)-N-Methyl-N-(4-(4-phenyl-4-((4-carboethoxymethylpiperazin-1-yl)carboxamido) piperidin-1-yl)-2-(3,4-dichlorophenyl)butyl)-2-methoxy-5-(1H-tetrazol-1-yl)benzamide

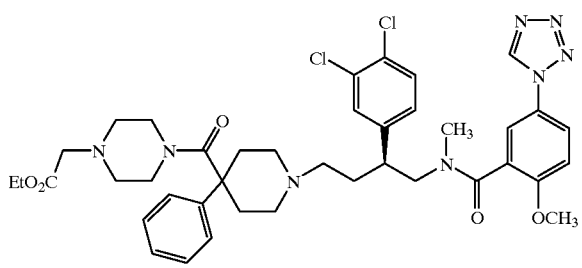

1.1 Synthesis of (S)-N-methyl-N-(4-(4-phenyl-4-((4-carboethoxymethylpiperazin-1-yl)carboxamido)piperidin-1-yl)-2-(3,4-dichlorophenyl)butyl)-2-methoxy-5-(1H-tetrazol-1-yl)benzamide Combine (S)-N-methyl-N-(2-(3,4-dichlorophenyl)-4-oxobutyl)-2-methoxy-5-(1H-tetrazol-1-yl)benzamide (0.40 g, 0.89 mmol) and 4-phenyl-4-((4-carboethoxymethylpiperazin-1-yl) carboxamido)piperidine hydriodic acid salt (0.60 g, 0.98 mmol) and 3 Å molecular sieves (about 5 g) in methanol (30 mL). After 25 hours, add a solution of sodium cyanoborohydride (0.90 ml, 1 M in tetrahydrofuran, 0.9 mmol). After 18 hours, filter the reaction mixture and evaporate the filtrate in vacuo to give a residue. Chromatograph the residue on silica gel eluting sequentially with 1.0% methanol/dichloromethane, 2% methanol/dichloromethane and 3% methanol/dichloromethane to give the title compound: $R_f$=0.30 (silica gel, 6% methanol/dichloromethane).

1.2 Synthesis of (S)-N-methyl-N-(4-(4-phenyl-4-((4-carboethoxymethylpiperazin-1-yl)carboxamido)piperidin-1-yl)- 2-(3,4-dichlorophenyl)butyl)-2-methoxy-5-(1H-tetrazol-1-yl)benzamide hydrochloric acid salt Combine (S)-N-methyl-N-(4-(4-phenyl-4-((4-carboethoxymethylpiperazin-1-yl)carboxamido)piperidin-1-yl)-2-(3,4-dichlorophenyl)butyl)-2-methoxy-5-(1H-tetrazol-1-yl)benzamide (0.33 g, 0.42 mmol) in dichloromethane (10 mL). Purge with hydrochloric acid (gas). After 5 minutes, evaporate the reaction mixture in vacuo to give a residue. Triturate the residue with diethyl ether to give, after stirring, a solid. Collect the solid by filtration to give, after drying, the title compound.

PREPARATION 6

Synthesis of (S)-N-methyl-N-(2-(4-fluorophenyl)-4-oxobutyl)-2-methoxy-5-(1H-tetrazol-1-yl)benzamide Combine (S)-4-benzyl-2-oxazolidinone (22.9 g, 129 mmol) and tetrahydrofuran (120 mL). Cool in a dry-ice/acetone bath. Add dropwise a solution of n-butyl lithium (52 mL, 2.5 M, 130 mmol). After 15 minutes, slowly add a solution of 4-fluorophenylacetyl chloride (22.3 g, 129 mmol) in tetrahydrofuran (50 mL). Warm to ambient temperature. After 2 hours, quench the reaction mixture by the addition of a saturated aqueous sodium bicarbonate solution. Separate the layers and extract the aqueous layer with diethyl ether. Combine the organic layers, dry over $Na_2SO_4$, filter, and evaporate in vacuo to give a residue. Chromatograph the residue on silica gel eluting wit 15% ethyl acetate/hexane. Combine the product containing fractions, evaporate, and recrytallize from diethyl ether/hexane to give (S)-4-benzyl-3-(4-fluorophenyl)acetyl-2-oxazolidinone.

Alternately, combined (S)-benzyl-2-oxazolidinone(55.4 g, 313 mmol) and tetrahydrofuran (550 ml). Cool in a dry-ice/acetone bath. Add n-butyl lithium (125 ml, 1 M in hexane, 312 mmol). After 30 minutes, add dropwise 4-fluorophenylacetyl chloride (56.7 g, 328 mmol). After 30 minutes, warm to ambient temperature, add a saturated aqueous sodium bicarbonate solution, and stir. After 45 minutes, separate the layers and extract the aqueous layer three times with ethyl acetate, combine the organic layers, extract with brine, dry over $MgSO_4$, filter, and evaporate in vacuo to give a viscous oil. Stir the viscous oil under vacuum to remove residual solvent and triturate with isopropanol to give a solid. Collect the solid by the filtration and rinse with isopropanol to give, after drying, (S)-4-benzyl-3-(4-fluorophenyl)acetyl-2-oxazolidinone.

Combine (S)-4-benzyl-3-(4-fluorophenyl)acetyl-2-oxazolidinone (14.28 g, 45.6 mmol) and tetrahydrofuran (150 mL). Cool in a dry-ice/acetone bath. Add dropwise a solution of sodium bis(trimethylsilyl)amide (50 mL, 1.0 M in tetrahydrofuran, 50 mmol). After 25 minutes, add allyl iodide (13 mL, 142.2 mmol) and then replace the bath with a dry-ice/carbon tetrachloride bath. After 1 hour, quench the reaction by the addition of a saturated aqueous ammonium chloride solution, extract with diethyl ether, and separate the layers. Dry the organic layer over $Na_2SO_4$, filter, and evaporate in vacuo to give a residue. Chromatograph the residue on silica gel eluting with 1/6 ethyl acetate/hexane. Combine the product containing fractions, evaporate, and recrytallize from chloroform/hexane to give (S)-4-benzyl-3-(2-(4-fluorophenyl)pent-4-enoyl)-2-oxazolidinone: mp; 103–104° C. $R_f$=0.57 (silica gel, 20% ethyl acetate/hexane).

Alternately, combine (S)-4-benzyl-3-(4-fluorophenyl) acetyl-2-oxazolidinone (43.08 g, 426 mmol) and tetrahydrofuran (450 ml). Cool in a dry-ice/acetone bath. Add dropwise a solution of sodium bis(trimethylsilyl)amide (153.0 ml, 1 M in tetrahydrofuran, 137.5 mmol). After 40 minutes, add a solution of allyl iodide (39.0 ml, 426 mmol) and replace the bath with a dry-ice/carbon tetrachloride bath. After 1.5 hours, quench the reaction by the addition of a saturated aqueous solution of ammonium chloride, add diethyl ether (200 ml), and stir. After about 30 minutes, separate the layers and extract the aqueous layer twice with diethyl ether. Dry the combined organic layers over $MgSO_4$, filter, and evaporate in vacuo to give a residue. Dry the residue in a vacuum, dissolve in ethyl acetate (about 400 ml), and extract with a saturated aqueous sodium thiosulfate solution. Dry the organic layer over $MgSO_4$, filter, and evaporate in vacuo to give a residue. Chromatograph the residue on silica gel eluting with 13% ethyl acetate/hexane to give (S)-4-benzyl-3-(2-(4-fluorophenyl)pent-4-enoyl)-2-oxazolidinone.

Combine (S)-4-benzyl-3-(2-(4-fluorophenyl)pent-4-enoyl)-2-oxazolidinone (9.66 g, 27.34 mol), tetrahydrofuran (160 mL), and water (40 mL). Cool in an ice bath. Add lithium hydroxide hydrate (2.52 g, 60 mmol) and an aqueous solution of hydrogen peroxide (10 mL, 30% 116 mmol). After 3 hours, dilute the reaction mixture with an aqueous 1 M sodium hydroxide solution and extract twice with diethyl ether. Cool the aqueous layer in an ice bath, acidify with an aqueous concentrated hydrochloric acid solution (about 15 mL), and extract twice with dichloromethane. Extract the combined organic layers with a saturated aqueous sodium thiosulfate solution, dry over $MgSO_4$, filter, and evaporate in vacuo to give (S)-2-(4-fluorophenyl)pent-4-enoic acid.

Combine (S)-2-(4-fluorophenyl)pent-4-enoic acid (3.61 g, 18.6 mmol), dichloromethane (20 mL), and dimethylformamide (2 drops). Add oxalyl chloride (1.94 mL, 22.3 mmol). After 2 hours, evaporate in vacuo to give (S)-2-(4-fluorophenyl)pent-4-enoyl chloride. Combine with toluene (10 mL) and slowly add, with vigorous stirring, to a cooled (ice bath) aqueous solution of methylamine (4 mL, 40%). After 1 hour, partition the reaction mixture between water and dichloromethane. Separate the layers, extract the organic layer with a saturated aqueous sodium bicarbonate solution. Dry the organic over $MgSO_4$, filter, and evaporate in vacuo to give a residue. Triturate the residue with hexane to give a solid. Collect the solid by filtration and dry to give (S)-2-(4-fluorophenyl)pent-4-enoic acid, N-methyl amide: mp; 104–105° C. $R_f$=0.42 (silica gel, 50% ethyl acetate/hexane).

Combine (S)-2-(4-fluorophenyl)pent-4-enoic acid, N-methyl amide (3.1 g, 14.96 mmol) and tetrahydrofuran (35 mL). Cool in an ice bath, add a solution of lithium aluminum hydride (35 mL, 1.0 M in tetrahydrofuran, 35 mmol). After the addition is complete, heat the reaction mixture to reflux. After 2.5 hours, cool in an ice bath and carefully quench with water (1.3 mL), an aqueous 15% sodium hydroxide solution (1.3 mL), and then water (4 mL). Dilute the quenched reaction mixture with diethyl ether (75 mL), add $MgSO_4$, and stir. After 1 hour, filter through celite and rinse the solids with dichloromethane. Evaporate the filtrate in vacuo to give (S)-N-methyl-(2-(4-fluorophenyl) pent-4-enyl)amine: $R_f$=0.47 (silica gel, 18.5/1.5/0.2 dichloromethane/methanol/concentrated aqueous ammonia).

Combine (S)-N-methyl-2-(4-fluorophenyl)pent-4-enyl) amine (2.13 g, 11.0 mmol), acetone (100 mL, water (25 mL), and sodium bicarbonate (2.98 g, 35.5 mmol). Cool in an ice bath with vigorous stirring. Add portionwise, 2-methoxy-5-(1H-tetrazol-1-yl)benzoyl chloride (2.82 g, 11.7 mmol). After the addition is complete, warm to ambient temperature. After 1.5 hours, evaporate in vacuo to remove most of the acetone. Extract the evaporate reaction mixture with ethyl acetate. Extract the organic layer with a saturated aqueous sodium bicarbonate solution and then brine. Dry the organic layer over $MgSO_4$, filter, and evaporate in vacuo to give a residue. Chromatograph the residue on silica gel eluting with ethyl acetate to give (S)-N-methyl-N-(2-(4-fluorophenyl)pent-4-enyl)-2-methoxy-5-(1H-tetrazol-1-yl) benzamide: $R_f$=0.50 (silica gel, ethyl acetate).

Alternately, combine (S)-N-methyl-2-(4-fluorophenyl) pent-4-enyl)amine (2.25 g, 11 mmol), tetrahydrofuran (20 mL), water (5 mL), and sodium bicarbonate (1.23 g, 11.6 mmol). Add portionwise, 2-methoxy-5-(1H-tetrazol-1-yl) benzoyl chloride (2.78 g, 11.6 mmol). After 4 hours, evaporate in vacuo to remove most of the tetrahydrofuran. Separate the layers, extract the aqueous layer four times with dichloromethane. Combine the organic layers and extract with a saturated aqueous sodium bicarbonate solution. Dry the organic layer over $Na_2SO_4$, filter, and evaporate in vacuo to give a residue. Chromatograph the residue on silica gel eluting with ethyl acetate to give (S)-N-methyl-N-(2-(4-fluorophenyl)pent-4-enyl)-2-methoxy-5-(1H-tetrazol-1-yl) benzamide.

Combine (S)-N-methyl-N-(2-(4-fluorophenyl)pent-4-enyl)-2-methoxy-5-(1H-tetrazol-1-yl)benzamide (4.46 g, 11.3 mmol), acetone/t-butanol/water (2/1/1, 64 mL), and a solution of N-methylmorpholine N-oxide (3.0 mL, 50% in water, 14.5 mmol). Add a solution of osmium tetraoxide (3.0 mL, 4% in water, 0.5 mmol). After 3 hours, evaporate in vacuo to remove most of the acetone and partition the evaporated reaction mixture between dichloromethane and an aqueous 10% solution of sodium thiosulfate. Separate the layer, dry the organic layer over $MgSO_4$, filter, and evaporate in vacuo to give a residue. Combine the residue, tetrahydrofuran (80 mL), and water (20 mL). Add sodium meta-periodate (3.63 g). After 1.5 hours, filter the reaction mixture, rinse the solids with dichloromethane, and evaporate the filtrate to obtain a residue. Chromatograph the residue on silica gel eluting with ethyl acetate to give the title compound: $R_f$=0.22 (silica gel, ethyl acetate).

EXAMPLE 2

(S)-N-Methyl-N-(4-(4-phenyl-4-((4-carboethoxymethylpiperazin-1-yl)carboxamido) piperidin-1-yl)-2-(4-fluorophenyl)butyl)-2-methoxy-5-(1H-tetrazol-1-yl)benzamide

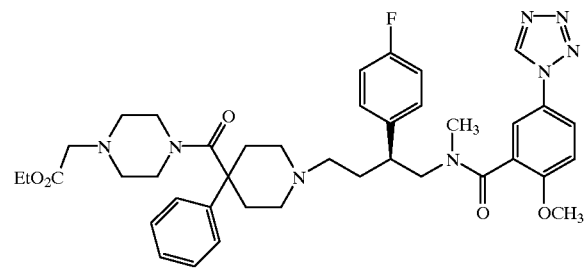

2.1 Synthesis of (S)-N-Methyl-N-(4-(4-phenyl-4-((4-carboethoxymethylpiperazin-1-yl)carboxamido)piperidin-1-yl)-2-(4-fluorophenyl)butyl)-2-methoxy-5-(1H-tetrazol-1-yl)benzamide Prepare by the method of Example 1.1 using (S)-N-methyl-N-(2-(3,4-dichlorophenyl)-4-oxobutyl)-2-methoxy-5-(1H-tetrazol-1-yl)benzamide and 4-phenyl-4-((4-carboethoxymethylpiperazin-1-yl)carboxamido)piperidine hydriodic acid salt to give the title compound.

PREPARATION 7

Synthesis of (S)-N-methyl-N-(2-phenyl-4-oxobutyl)-2-methoxy-5-(1H-tetrazol-1-yl)benzamide Combine (S)-4-benzyl-2-oxazolidinone (22.9 g, 129 mmol) and tetrahydrofuran (120 mL). Cool in a dry-ice/acetone bath. Add dropwise a solution of n-butyl lithium (52 mL, 2.5 M, 130 mmol). After 15 minutes, slowly add a solution of phenylacetyl chloride (20 g, 129.4 mmol) in tetrahydrofuran (50 mL). After 20 minutes, warm to ambient temperature. After 2 hours, quench the reaction mixture by the addition of a saturated aqueous sodium bicarbonate solution. Separate the layers and extract the aqueous layer with diethyl ether. Combine the organic layers, dry over $Na_2SO_4$, filter, and evaporate in vacuo to give a residue. Chromatograph the residue on silica gel eluting with 15% ethyl acetate/hexane. Combine the product containing fractions, evaporate, and recrytallize from diethyl ether/hexane to give (S)-4-benzyl-3-phenylacetyl-2-oxazolidinone.

Combine (S)-4-benzyl-3-phenylacetyl-2-oxazolidinone (14.13 g, 47.9 mmol) and tetrahydrofuran (150 mL). Cool in a dry-ice/acetone bath. Add dropwise a solution of sodium bis(trimethylsilyl)amide (52.6 mL, 1.0 M in tetrahydrofuran, 52.6 mmol). After 25 minutes, add allyl iodide (13.12 mL, 143.5 mmol) and then replace the bath with a dry-ice/carbon tetrachloride bath. After 1 hour, quench the reaction by the addition of a saturated aqueous ammonium chloride solution, extract with diethyl ether, and separate the layers. Dry the organic layer over $Na_2SO_4$, filter, and evaporate in vacuo to give a residue. Chromatograph the residue on silica gel eluting with 15% ethyl acetate/hexane. Combine the product containing fractions, evaporate, and recrytallize from chloroform/hexane to give (S)-4-benzyl-3-(2-phenylpent-4-enoyl)-2-oxazolidinone: $R_f$=0.40 (silica gel, 15% ethyl acetate/hexane).

Alternately, combine (S)-4-benzyl-3-phenylacetyl-2-oxazolidinone (8.0 g, 27 mmol) and tetrahydrofuran (50 mL). cool in a dry-ice/acetone bath. Add dropwise a solution of sodium bis(trimethylsilyl)amide (30 mL, 1.0 M in tetrahydrofuran, 30 mmol). After 30 minutes, add allyl iodide (9.1 g, 54 mmol) and then replace the bath with a dry-ice/carbon tetrachloride bath. After 1.5 hours, quench the reaction by the addition of a saturated aqueous sodium chloride solution, extract with diethyl ether, and separate the layers. Extract the aqueous layer three times with diethyl ether. Combine the organic layers, extract with an aqueous 1 M hydrochloric acid solution, a saturated aqueous sodium bicarbonate solution, dry the organic layer over $Na_2SO_4$, filter, and evaporate in vacuo to give a residue. Dissolve in ethyl acetate, extract with a saturated aqueous sodium thiosulfate solution, dry the over $Na_2SO_4$, filter, and evaporate in vacuo to give a residue. Chromatograph the residue on silica gel eluting with 10% ethyl acetate/hexane. Combine the product containing fractions, evaporate, and recrytallize from chloroform/hexane to give (S)-4-benzyl-3-(2-phenylpent-4-enoyl)-2-oxazolidinone.

Combine (S)-4-benzyl-3-(2-phenylpent-4-enoyl)-2-oxazolidinone (3.35 g, 10 mol), tetrahydrofuran (80 mL), and water (20 mL). Cool in an ice bath. Add lithium hydroxide hydrate (0.84 g, 20 mmol) and an aqueous solution of hydrogen peroxide (4 mL, 30%, 46.4 mmol). After 3 hours, concentrate the reaction mixture to about half volume, dilute the concentrated reaction mixture with an aqueous 1 M sodium hydroxide solution and extract twice with diethyl ether. Cool the aqueous layer in an ice bath, acidify with an aqueous 3 M hydrochloric acid solution, and extract twice with dichloromethane. Extract the combined organic layers with a saturated aqueous sodium thiosulfate solution, dry over $MgSO_4$, filter, and evaporate in vacuo to give(S)-2-phenylpent-4-enoic acid: $R_f$=0.48 (silica gel, 5% methanol/dichloromethane).

Combine (S)-2-phenylpent-4-enoic acid (1.53 g, 8.7 mmol), dichloromethane (10 mL), and dimethylformamide (1 drop). Add oxalyl chloride (1 mL, 11.46 mmol). After 2 hours, evaporate in vacuo to give (S)-2-phenylpent-4-enoyl chloride. Combine with toluene (10 mL) and add, with vigorous stirring, to a cooled (ice bath) aqueous solution of methylamine (2 mL, 40%). After 1 hour, partition the reaction mixture between water and dichloromethane. Separate the layers, dry the organic over $MgSO_4$, filter, and evaporate in vacuo to give a residue. Triturate the residue with hexane to give a solid. Collect the solid by filtration and dry to give (S)-2-phenylpent-4-enoic acid, N-methyl amide: mp; 97–99° C. $R_f$=0.53 (silica gel, 50% ethyl acetate/hexane).

Combine (S)-2-phenylpent-4-enoic acid, N-methyl amide (1.35 g, 7.13 mmol) and tetrahydrofuran (20 mL). Cool in an ice bath, add a solution of lithium aluminum hydride (17 mL, 1.0 M in tetrahydrofuran, 17 mmol). After the addition is complete, heat the reaction mixture to reflux. After 24 hours, cool in an ice bath and carefully quench with water (0.6 mL), an aqueous 15% sodium hydroxide solution (0.6 mL) and then water (2 mL). Dilute the quenched reaction mixture with diethyl ether (50 mL), add $MgSO_4$, and stir. After 2 hours, filter through celite and rinse the solids with dichloromethane. Dry the filtrate with $MgSO_4$, and evaporate in vacuo to give (S)-N-methyl-(2-phenylpent-4-enyl) amine: $R_f$=0.51 (silica gel, 18/2/0.2 dichloromethane/methanol/concentrated aqueous ammonia).

Combine (S)-N-methyl-(2-phenylpent-4-enyl)amine (1.93 g, 11.0 mmol), acetone/water (4/1, 125 mL), and sodium bicarbonate (3.0 g, 35.5 mmol). Cool in an ice bath with vigorous stirring. Add portionwise, 2-methoxy-5-(1H-tetrazol-1-yl)benzoyl chloride (2.86 g, 11.8 mmol). After the addition is complete, warm to ambient temperature. After 1.5 hours, evaporate in vacuo to remove most of the acetone. Extract the evaporated reaction mixture with ethyl acetate. Extract the organic layer with a saturated aqueous sodium bicarbonate solution and then brine. Dry the organic layer over $MgSO_4$, filter, and evaporate in vacuo to give a residue. Chromatograph the residue on silica gel eluting with ethyl acetate to give (S)-N-methyl-N-(2-phenylpent-4-enyl)-2-methoxy-5-(1H-tetrazol-1-yl)benzamide: $R_f$=0.35 (silica gel, ethyl acetate).

Combine (S)-N-methyl-N-(2-phenylpent-4-enyl)-2-methoxy-5-(1H-tetrazol-1-yl)benzamide (3.13 g, 8.3 mmol), acetone/t-butanol/water (2/1/1, 90 mL), and a solution of N-methylmorpholine N-oxide (2.06 mL, 50% in water, 9.95 mmol). Add a solution of osmium tetraoxide (2.56 mL, 4% in water, 0.5 mmol). After 18 hours, evaporate in vacuo to remove most of the acetone and extract the evaporated reaction mixture with dichloromethane. Extract the organic layer with an aqueous 10% solution of sodium thiosulfate. Dry the organic layer over $MgSO_4$, filter, and evaporate in vacuo to give a residue: $R_f$=0.22 (silica gel, 7% methanol/dichloromethane/0.1% concentrated ammonium hydroxide). Combine the residue (3.6 g, 8.3 mmol) and tetrahydrofuran/water (90 mL, 4/1). Add sodium meta-periodate (2.13 g, 9.95 mmol). After 1 hour, filter the reaction mixture, rinse the solids with tetrahydrofuran, and evaporate the filtrate to obtain a residue. Dilute the residue with ethyl acetate (150 mL), extract with brine, dry over $MgSO_4$, filter, and evaporate in vacuo to give a residue. Chromatograph the residue on silica gel eluting with 5% methanol/dichloromethane/0.1% concentrated ammonium hydroxide to give the title compound: $R_f$=0.33 (silica gel, 7% methanol/dichloromethane/0.1% concentrated ammonium hydroxide). $[\alpha]_D^{20}$=13.70° (c=0.59, chloroform)

EXAMPLE 3

(S) N-Methyl-N-(4-(4-phenyl-4-((4-carboethoxymethylpiperazin-1-yl)carboxamido)piperidin-1-yl)-2-phenylbutyl)-2-methoxy-5-(1H-tetrazol-yl)benzamide

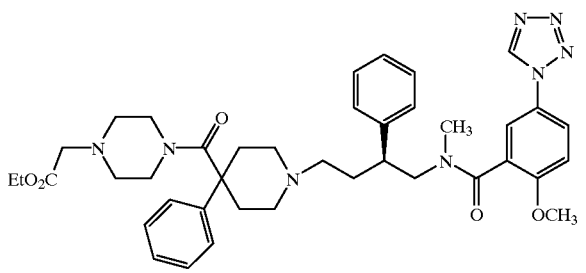

3.1 Synthesis of (S)-N-Methyl-N-(4-(4-phenyl-4-((4-carboethoxymethylpiperazin-1-yl)carboxamido)piperidin-1-yl)-2-phenylbutyl)-2-methoxy-5-(1H-tetrazol-1-yl)benzamide Prepare by the method of Example 1.1 using (S)-N-methyl-N-(2-phenyl-4-oxobutyl)-2-methoxy-5-(1H-tetrazol-1-yl)benzamide and 4-phenyl-4-((4-carboethoxymethylpiperazin-1-yl)carboxamido)piperidine hydriodic acid salt to give the title compound.

EXAMPLE 4

(S)-N-Methyl-N-(4-(4-phenyl-4-((4-carboxymethylpiperazin-1-yl)carboxamido)piperidin-1-yl)-2-(3,4-dichlorophenyl)butyl)-2-methoxy-5-(1H-tetrazol-1-yl)benzamide hydrochloric acid salt

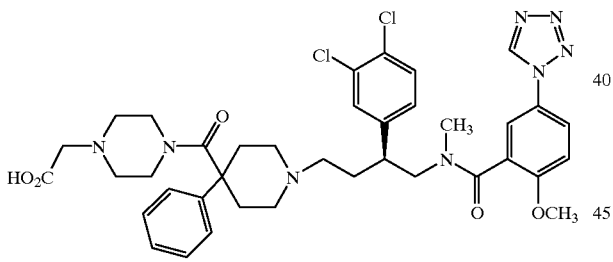

4.1 Synthesis of (S)-N-methyl-N-(4-(4-phenyl-4-((4-carboxymethylpiperazin-1-yl)carboxamido)piperidin-1-yl)-2-(3,4-dichlorophenyl)butyl)-2-methoxy-5-(1H-tetrazol-1-yl)benzamide hydrochloric acid salt Combine (S)-N-methyl-N-(4-(4-phenyl-4-((4-carboethoxymethylpiperazin-1-yl)carboxamido)piperidin-1-yl)-2-(3,4-dichlorophenyl)butyl)-2-methoxy-5-(1H-tetrazol-1-yl)benzamide (0.29 g, 0.34 mmol) and lithium hydroxide (50 mg, 2.1 mmol) in tetrahydrofuran/water (10 mL/10 mL). After 2 hours, evaporate in vacuo to remove most of the tetrahydrofuran. Adjust the pH to 6 using a 1 M aqueous solution of hydrochloric acid. Evaporate the aqueous reaction mixture in vacuo to give a residue. Combine the residue and ethanol and again evaporate in vacuo to give a residue, add a small amount of water, stir, and decant to give a residue. Combine the residue and a 1 M solution of hydrochloric acid and evaporate in vacuo and then add ethanol and evaporate in vacuo to give, after drying, the title compound.

PREPARATION 8

4-Phenyl-4-((4-carboethoxypiperidin-1-yl)carboxamido)piperidine hydrochloric acid salt Combine 4-phenylpiperidine-4-carboxylic acid p-toluenesulfonic acid (97.5 g, 0.258 mol), N,N-diisopropylethylamine (55 mL, 0.316 mol), and dimethylformamide (900 mL). Add dropwise, a solution of di-t-butyl dicarbonate (65.0 g, 0.30 mol) in dimethylformamide (300 mL). After 20 hours, dilute the reaction mixture with diethyl ether and extract with three times with water and then with brine. Dry the organic layer over $MgSO_4$, filter, rinse the $MgSO_4$ with dichloromethane. Evaporate in vacuo to give 1-t-butoxycarbonyl-4-phenyl-piperidine-4-carboxylic acid.

Combine 1-t-butoxycarbonyl-4-phenyl-piperidine-4-carboxylic acid (18.7 g, 97.5 mmol), N,N-diisopropylethylamine (34.0 mL, 0.195 mol) in dichloromethane (400 mL). Add 1-hydroxybenzotriazole hydrate (13.2 g, 97.7 mmol) and ethyl isonipecotate(4-carboethoxypiperidine) (14.0 g, 88.8 mmol). Add 1-ethyl-3-(3-dimethylaminopropyl)carbodiimide hydrochloride. After 18 hours, dilute the reaction mixture with dichloromethane and extract twice with water. Dry the organic layer over $MgSO_4$, filter, and evaporate in vacuo to give 1-t-butoxycarbonyl-4-phenyl-4-((4-carboethoxypiperidin-1-yl)carboxamido) piperidine.

Combine 1-t-butoxycarbonyl-4-phenyl-4-((4-carboethoxypiperidin-1-yl)carboxamido)piperidine (25.0 g, 56.6 mmol) and dichloromethane (200 mL). Add a solution of hydrochloric acid in dioxane (50 mL, 4 M, 200 mmol). After 3 hours, add diethyl ether (400 mL) and filter to give, after drying, the title compound.

Also prepared by the method of Preparation 8 are:
a) 4-phenyl-4-((3-carboethoxypiperidin-1-yl)carboxamido)piperidine hydrochloric acid salt using ethyl nipecotate (3-carboethoxypiperidine);
b) 4-phenyl-4-((2-carboethoxypiperidin-1-yl)carboxamido)piperidine hydrochloric acid salt using ethyl pipecolinate (2-carboethoxypiperidine);
c) 4-phenyl-4-((2-carbomethoxypyrrolidin-1-yl)carboxamido)piperidine hydrochloric acid salt using DL-proline methyl ester hydrochloride (2-carbomethoxypyrrolidine hydrochloride);
d) 4-phenyl-4-((2-carboethoxymorpholin-4-yl)carboxamido)piperidine hydrochloric acid salt using 2-carboethoxymorpholine.

PREPAPATION 9

Synthesis of 1-(t-butyldimethylsilyloxy)-2-bromoethane

Combine imidazole (59.9 g, 880 mmol), t-butyldimethylsilyl chloride (60.3 g, 400 mmol), and dimethylformamide (300 mL). Cool to 0° C. in a salt-ice bath. Add dropwise 2-bromoethanol (50.0 g, 400 mmol) at such a rate that the temperature of the reaction mixture does not rise above 0° C. After 2 hours, warm to ambient temperature. After 18 hours, extract the reaction mixture three times with hexane. Combine the hexane layers and extract three times with a saturated aqueous solution of ammonium chloride, three times with a saturated aqueous solution of sodium bicarbonate, and then brine. Dry the organic layer over $Na_2SO_4$, filter, and evaporate in vacuo to give the title compound.

PREPARATION 10

Synthesis of 1-(t-butyldimethylsilyloxy)-2-iodoethane

Prepare by the method of Preparation 9 using 2-iodoethanol to give the title compound.

EXAMPLE 5

N-Methyl-N-(4-(4-phenyl-4-((4-carboethoxypiperidin-1-yl)carboxamido)piperidin-1-yl)-2-(4-fluorophenyl)butyl)-3,4,5-trimethoxybenzamide

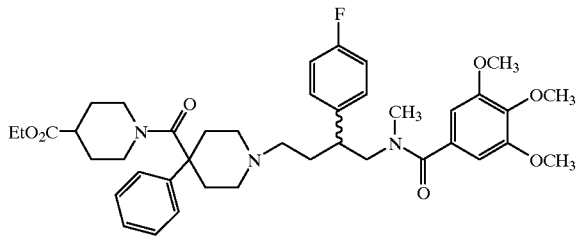

5.1.1 Synthesis of 2-(4-fluorophenyl)-4-(t-butyldimethylsilyloxy)butyronitrile As adapted from the procedure of *Org. Syn. Collective Volume VI*, 897–900 (1988), combine 4-fluorophenylacetonitrile (56.5 g, 418 mmol), an aqueous 50% sodium hydroxide solution (106.3 g, 1330 mmol), and benzyltriethylammonium chloride (0.95 g) in water (100 mL). Warm to about 30° C. and stir vigorously. Add dropwise over about 30 minutes 1-(t-butyldimethylsilyloxy)-2-bromoethane (50 g, 209 mmol). When the addition is complete, warm to about 40° C. and continue to stir vigorously. After 18 hours, dilute the reaction mixture with ethyl acetate and stir. After 30 minutes, separate the organic layer and extract three times with aqueous saturated ammonium chloride solution, two times with an aqueous saturated sodium bicarbonate solution, and then brine. Dry the organic layer over $Na_2SO_4$, filter, and concentrate in vacuo to give a residue. Distill the residue to give the title compound: bp; 100–115° C. at 0.2 mm Hg. $R_f$=0.35 (silica gel, 1/1 dichloromethane/hexane).

5.1.2 Synthesis of 2-(4-fluorophenyl)-4-(t-butyldimethylsilyloxy)butyronitrile Combine 4-fluorophenylacetonitrile (5.0 g, 37.0 mmol), and tetrahydrofuran (45 mL). Cool to about −65° C. using a dry-ice/acetone bath. Add a solution of potassium bis(trimethylsilyl)amide (89 mL, 0.5 M in toluene, 44.5 mmol). After 1 hour, add a solution of 1-(t-butyldimethylsilyloxy)-2-iodoethane (12.7 g, 44.4 mmol) in tetrahydrofuran (10 mL). After the addition of 1-(t-butyldimethylsilyloxy)-2-iodoethane is complete, warm to ambient temperature. After 18 hours, dilute the reaction mixture with tetrahydrofuran and extract three times with aqueous saturated ammonium chloride solution and then twice with brine. Dry the organic layer over $Na_2SO_4$, filter, and concentrate in vacuo to give a residue. Chromatograph the residue on silica gel eluting with 1/1 dichloromethane/hexane to give the title compound.

5.1.3 Synthesis of 2-(4-fluorophenyl)-4-(t-butyldimethylsilyloxy)butyronitrile Combine 4-fluorophenylacetonitrile (1.0 g, 7.4 mmol), and tetrahydrofuran (9 mL). Cool to about −70° C. using a dry-ice/acetone bath. Add a solution of potassium bis(trimethylsilyl)amide (14.8 mL, 0.5 M in toluene, 7.4 mmol). After 2 hours, add, via cannula, the solution prepared above to a cooled (−25° C.) solution of 1-(t-butyldimethylsilyloxy)-2-iodoethane (2.1 g, 7.4 mmol) in tetrahydrofuran (4 mL). After the addition to 1-(t-butyldimethylsilyloxy)-2-iodoethane is complete, warm to ambient temperature. After 18 hours, dilute the reaction mixture with tetrahydrofuran and extract three times with aqueous saturated ammonium chloride solution and then twice with brine. Dry the organic layer over $Na_2SO_4$, filter, and concentrate in vacuoto give a residue. Chromatograph the residue on silica gel eluting with 1/1 dichloromethane/hexane to give the title compound.

5.1.4 Synthesis of 2-(4-fluorophenyl)-4-(t-butyldimethylsilyloxy)butyronitrile Combine 4-fluorophenylacetonitrile (1.0 g, 7.4 mmol), and tetrahydrofuran (20 mL). Cool to about −70° C. using a dry-ice/acetone bath. Add a solution of s-butyl lithium (6.3 mL, 1.3 M in cyclohexane, 8.1 mmol). After 1 hour, add a solution of 1-(t-butyldimethylsilyloxy)-2-iodoethane (2.1 g, 7.4 mmol) in tetrahydrofuran (4 mL). After 2 hours, warm to ambient temperature. After 18 hours, dilute the reaction mixture with ethyl acetate and extract twice with aqueous saturated ammonium chloride solution and then twice with brine. Dry the organic layer over $Na_2SO_4$, filter, and concentrate in vacuoto give a residue. Chromatograph the residue on silica gel eluting with 1/1 dichloromethane/hexane to give the title compound.

5.2 Synthesis of 2-(4-fluorophenyl)-4-(t-butyldimethylsilyloxy)butylamine

Combine 2-(4-fluorophenyl)-4-(t-butyldimethylsilyloxy)butyronitrile (43.0 g, 146.5 mmol) and ethanol (200 mL) in a Parr bottle. Add Raney nickel (129 g) to the reaction mixture. Add a solution of concentrated ammonium hydroxide (40 mL). Hydrogenate on a Parr shaker at 50 psi. After 24 hours, filter through a celite pad and rinse the solids with ethanol. Concentrate the filtrate in vacuoto give the title compound.

5.3 Synthesis of N-(2-(4-fluorophenyl)-4-(t-butyldimethylsilyloxy)butyl)-3,4,5-trimethoxybenzamide Combine 2-(4-fluorophenyl)-4-(t-butyldimethylsilyloxy)butylamine (7.33 g, 24.6 mmol) and sodium carbonate (2.61 g, 24.6 mmol) in 4/1 ethyl acetate/water (400 mL). Cool the reaction mixture to 0° C. with a salt-ice bath. Slowly, add a solution of 3,4,5-trimethoxybenzoyl chloride (5.96, 25.9 mmol) in ethyl acetate (50 mL) at such a rate that the temperature of the reaction mixture does not rise above 5° C. After 2 hours, warm to ambient temperature. After 18 hours, separate the layers and extract the organic layer twice with a saturated aqueous solution of ammonium chloride, twice with a saturated aqueous solution of sodium bicarbonate and then with brine. Dry the organic layer over $Na_2SO_4$, filter, and concentrate in vacuo to obtain a residue. Chromatograph the residue on silica gel eluting with 50% ethyl acetate/hexane to give, after drying, the title compound: mp; 113–114° C. Elemental Analysis calculated for $C_{26}H_{38}FNO_3Si$: C, 63.51; H, 7.79; N, 2.85; Found: C, 63.43; H, 7.51; N, 2.66. $R_f$=0.30 (silica gel, 50% ethyl acetate/hexane).

5.4 Synthesis of N-methyl-N-(2-(4-fluorophenyl)-4-(t-butyldimethylsilyloxy)but yl)-3,4,5-trimethoxybenzamide Combine hexane washed sodium hydride (0.48 g, 50% in oil, 10.0 mmol) and dimethylformamide (5 mL). Cool the reaction mixture to 0° C. with a salt-ice bath. Slowly, add a solution of N-(2-(4-fluorophenyl)-4-(t-butyldimethylsilyloxy)butyl)-3,4,5-trimethoxybenzamide (4.0 g, 8.1 mmol) in dimethylformamide (10 mL). Stir until gas evolution ceases. Add iodomethane (0.62 mL, 10.0 mmol). After 16 hours, dilute the reaction mixture with ethyl acetate and extract three times with water and then brine. Dry the organic layer over $Na_2SO_4$, filter, and concentrate in vacuoto give a residue. Chromatograph the residue on silica gel eluting with 1/1 ethyl acetate/hexane to give, after drying, the title compound: $R_f$=0.15 (silica gel, 1/1 ethyl acetate/hexane). Elemental Analysis calculated for $C_{27}H_{40}FNO_3Si$: C, 64.13; H, 7.97; N, 2.77; Found: C, 63.73; H, 7.90; N, 2.88.

5.5 Synthesis of N-methyl-N-(2-(4-fluorophenyl)-4-hydroxybutyl)-3,4,5-trimethoxybenzamide Combine N-methyl-N-(2-(4-fluorophenyl)-4-(t-butyldimethylsilyloxy)butyl)-3,4,5-trimethoxybenzamide (3.9 g, 7.65 mmol) and methanol (40 mL). Add ammonium fluoride (1.71 g, 46.0 mmol). Heat to reflux. After 20 hours, concentrate in vacuoto give a residue. Combine the residue with water and dichloromethane. Separate the layers and extract the aqueous layer twice with dichloromethane. Combine the organic layers and dry over $Na_2SO_4$, filter, and concentrate in vacuoto give the title compound: mp; 30–35° C. $R_f$=0.30 (silica gel, 10/1 ethyl acetate/methanol).

5.6 Synthesis of N-methyl-N-(2-(4-fluorophenyl)-4-methanesulfonylbutyl)-3,4,5-trimethoxybenzamide Combine N-methyl-N-(2-(4-fluorophenyl)-4-hydroxybutyl)-3,4,5-trimethoxybenzamide (2.5 g, 6.36 mmol), N,N-diisopropylethylamine (2.4 mL, 14.0 mmol), and anhydrous dichloromethane (25 mL). Cool the reaction mixture to 0° C. with an ice bath. Slowly, add methanesulfonyl chloride (0.69 mL, 8.9 mmol). After 1 hour, dilute the reaction mixture with dichloromethane and extract 3 times with aqueous 1M hydrochloric acid solution, 2 times with a saturated solution of sodium bicarbonate, and then brine. Dry the organic layer over $Na_2SO_4$, filter, and concentrate in vacuoto obtain the title compound: $R_f$=0.43 (silica gel, 10/1 ethyl acetate/methanol).

5.7 Synthesis of N-Methyl-N-(4-(4-phenyl-4-((4-carboethoxypiperidin-1-yl)carboxamido)piperidin-1-yl)-2-(4-fluorophenyl)butyl)-3,4,5-trimethoxybenzamide Combine N-methyl-N-(2-(4-fluorophenyl)-4-methanesulfonylbutyl)-3,4,5-trimethoxybenzamide (0.74 g, 1.64 mmol), (0.86 g, 1.64 mmol), 4-phenyl-4-((4-carboethoxypiperidin-1- yl)carboxamido)piperidine hydrochloric acid salt (0.57 g, 1.97 mmol), sodium iodide (0.25 9, 1.64 mmol), and N,N-diisopropylethylamine (0.84 g, 6.6 mmol) in acetonitrile (12 mL). Heat to reflux. After 10 hours, cool and dilute the reaction mixture ethyl acetate. Extract three times with a saturated aqueous ammonium chloride solution, twice with a saturated aqueous sodium bicarbonate solution, and then brine. Dry the organic layer over $Na_2SO_4$, filter, and evaporate in vacuo to give the title compound.

PREPARATION 11

Synthesis of 1-(tetrahydropyran-2-yloxy)-2-bromoethane

Combine 2-bromoethanol (14.2 mL, 200 mmol) and dihydropyrane (18.25 mL, 200 mmol) in dichloromethane (20 mL). Add pyridinium p-toluenesulfonic acid (5 g, 20 mmol). After 2.5 hours, dilute the reaction mixture with diethyl ether and extract with water, 1/1 water/brine, water, and then brine. Dry the organic layer over $MgSO_4$, filter, and evaporate in vacuoto give a residue. Distill the residue to give the title compound: bp; 80–90° C. at 15–20 mm Hg.

EXAMPLE 6

N-Methyl-N-(4-(4-phenyl-4-((3-carboethoxypiperidin-1-yl)carboxamido)piperidin-1-yl)-2-(3,4-dichlorophenyl)butyl)benzamide

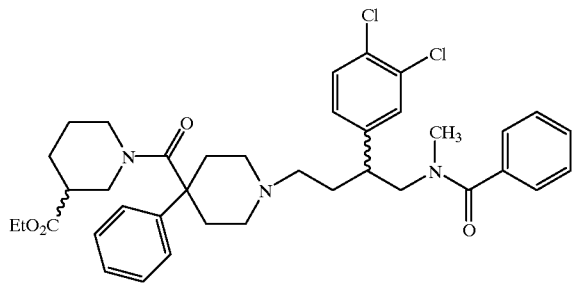

6.1 Synthesis of 2-(3,4-dichlorophenyl)-4-(tetrahydropyran-2-yloxy)butyronitrile Combine sodium hydride (1.2 g, 50 mmol) and tetrahydrofuran (20 mL). Add dropwise a solution of 3,4-dichlorophenylacetonitrile (8.9 g, 47.8 mmol) in tetrahydrofuran (50 mL) at about 0° C. When the addition is complete, allow to warm to ambient temperature and stir. After 2.5 hours, cool to 0° C and add 1-(tetrahydropyran-2-yloxy)-2-bromoethane (10.0 g, 47.9 mmol). Warm to ambient temperature. After 16 hours, pour the reaction mixture into saturated ammonium chloride and extract with diethyl ether. Separate the organic layer and extract with water and brine. Dry the organic layer over $MgSO_4$, filter and concentrate in vacuo to give a residue. Chromatograph the residue on silica gel eluting sequentially with 5% ethyl acetate/hexane, 10% ethyl acetate/hexane, and 20% ethyl acetate in hexane to give the title compound.

6.2 Synthesis of 2-(3,4-dichlorophenyl)-4-(tetrahydropyran-2-yloxy)butylamine

Combine 2-(3,4-dichlorophenyl)-4-(tetrahydropyran-2-yloxy)butyronitrile (7 g) and ethanol (20 mL) in a Parr bottle. Add Raney nickel (1 g) to the reaction mixture. Add a solution of concentrated ammonium hydroxide (3.5 mL). Hydrogenate on a Parr shaker at 50 psi. After 24 hours, filter through a celite pad and rinse the solids with ethanol. Concentrate the filtrate in vacuo to obtain a residue. Chromatograph the residue in vacuoon silica gel eluting sequentially with 50% ethyl acetate/hexane and 10% methanol/dichloromethane to give the title compound.

6.3 Synthesis of N-(2-(3,4-dichlorophenyl)-4-(tetrahydropyran-2-yloxy)butyl)benzamide Combine 2-(3,4-dichlorophenyl)-4-(tetrahydropyran-2-yloxy)butylamine (3.05 g, 9.6 mmol) and N-methylmorpholine (2.2 mL, 20 mmol) in anhydrous dichloromethane (25 mL). Cool the reaction mixture to 0° C. with a salt-ice bath. Slowly, add benzoyl chloride (1.2 mL, 10.3 mmol). After 1 hour, extract the reaction mixture with a saturated solution of sodium bicarbonate and then water. Dry the organic layer over $MgSO_4$, filter, and concentrate in vacuoto obtain a residue. Chromatograph the residue on silica gel eluting sequentially with 35% ethyl acetate/hexane and then with 50% ethyl acetate/hexane to give the title compound.

6.4 Synthesis of N-methyl-N-(2-(3,4-dichlorophenyl)-4-(tetrahydropyran-2-yloxy )butyl)benzamide Combine N-(2-(3,4-dichlorophenyl)-4-(tetrahydropyran-2-yloxy)butyl)benzamide (3.84 g) and tetrahydrofuran (20 mL). Add sodium hydride (0.28 g, 11.5 mmol) and stir until gas evolution ceases. Add iodomethane (1.5 mL, 24.1 mmol). After 6 hours, dilute the reaction mixture with diethyl ether and extract with a saturated solution of ammonium chloride. Separate the organic layer and extract with sodium bisulfite solution, water, and brine. Dry the organic layer over $MgSO_4$, filter, and concentrate in vacuoto give the title compound.

6.5 Synthesis of N-methyl-N-(2-(3,4-dichlorophenyl)-4-hydroxybutyl)benzamide

Combine N-methyl-N-(2-(3,4-dichlorophenyl)-4-(tetrahydropyran-2-yloxy )butyl)benzamide (3.7 g) and methanol (30 mL). Add p-toluenesulfonic acid hydrate (0.73 g) and stir. After 18 hours, concentrate in vacuoto give a residue. Combine the residue and dichloromethane and extract with a saturated solution of sodium bicarbonate and then water. Dry the organic layer over $MgSO_4$, filter, and concentrate in vacuoto obtain a residue. Chromatograph the residue on silica gel eluting sequentially with 50% ethyl acetate/hexane and then ethyl acetate to give the title compound.

6.6 Synthesis of N-methyl-N-(2-(3,4-dichlorophenyl)-4-methanesulfonylbutyl)benzamide Combine N-methyl-N-(2-(3,4-dichlorophenyl)-4-hydroxybutyl)benzamide (0.5 g), N,N-diisopropylethylamine (0.3 mL, 1.7 mmol), and anhydrous dichloromethane (8 mL). Cool the reaction mixture to 0° C. with an ice bath. Slowly, add methanesulfonyl chloride (0.13 mL, 1.7 mmol). Warm to ambient temperature. After 18 hours, quench the reaction by the addition of ice. Separate the organic layer and extract 3 times with 1M hydrochloric acid solution and 2 times with a saturated solution of sodium bicarbonate. Dry the organic layer over $Na_2SO_4$, filter, and concentrate in vacuoto obtain the title compound.

6.7 Synthesis of N-methyl-N-(4-(4-phenyl-4-((3-carboethoxypiperidin-1-yl)carboxamido)piperidin-1-yl)-2-(3,4-dichlorophenyl)butyl)-benzamide Prepare by the method of Example 5.7 using N-methyl-N-(2-(3,4-dichlorophenyl)-4-methanesulfonylbutyl) benzamide and 4-phenyl-4-((3-carboethoxypiperidin-1-yl) carboxamido) piperidine hydrochloric acid to give the title compound.

EXAMPLE 7

N-Methyl-N-(4-(4-(4-phenyl-4-((2-carboethoxypiperidin-1-yl)carboxamido)piperidin-1-yl)-2-(4-methoxyphenyl)butyl)benzamide

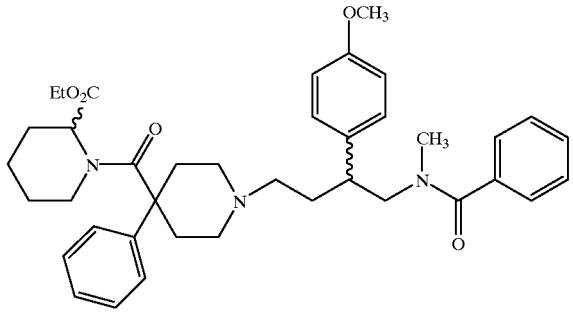

7.1 Synthesis of 2-(4-methoxyphenyl)-4-(t-butyldimethylsilyloxy)butyronitrile

Prepare by the method of Example 5.1.1 using 4-methoxyphenylacetonitrile and 1-(t-butyldimethylsilyloxy)-2-bromoethane to give the title compound.

7.2 Synthesis of 2-(4-methoxyphenyl)-4-(t-butyldimethylsilyloxy)butylamine

Prepare by the method of Example 5.2 using 2-(4-methoxyphenyl)-4-(t-butyldimethylsilyloxy)butyronitrile to give the title compound.

7.3 Synthesis of N-(2-(4-methoxyphenyl)-4-(t-butyldimethylsilyloxy)butyl)benzamide Prepare by the method of Example 5.3 using 2-(4-methoxyphenyl)-4-(t-butyldimethylsilyloxy)butylamine and benzoyl chloride to give the title compound.

7.4 Synthesis of N-methyl-N-(2-(4-methoxyphenyl)-4-(t-butyldimethylsilyloxy)butyl 1)benzamide Prepare by the method of Example 5.4 using N-(2-(4-methoxyphenyl)-4-(t-butyldimethylsilyloxy)butyl) benzamide to give the title compound.

7.5 Synthesis of N-methyl-N-(2-(4-methoxyphenyl)-4-hydroxybutyl)benzamide

Prepare by the method of Example 5.5 using N-methyl-N-(2-(4-methoxyphenyl)-4-(t-butyldimethylsilyloxy)butyl) benzamide to give the title compound.

7.6 Synthesis of N-methyl-N-(2-(4-methoxyphenyl)-4-methanesulfonylbutyl)benzamide Prepare by the method of Example 5.6 using N-methyl-N-(2-(4-methoxyphenyl)-4-hydroxybutyl)benzamide and methanesulfonyl chloride to give the title compound.

7.7 Synthesis of N-methyl-N-(4-(4-(4-phenyl-4-((2-carboethoxypiperidin-1-yl)carboxamido)piperidin-1-yl)-2-(4-methoxyphenyl)butyl)benzamide Prepare by the method of Example 5.7 using N-methyl-N-(2-(4-methoxyphenyl)-4-methanesulfonylbutyl) benzamide and 4-phenyl-4-((2-carboethoxypiperidin-1-yl) carboxamido)piperidine hydrochloric acid salt to give the title compound.

EXAMPLE 8

N-Methyl-N-(4-phenyl-4-((4-phenyl-4-((2-carbomethoxypyrrolidin-1-yl)carboxamido) piperidin-1-yl)2-phenylbutyl)benzamide

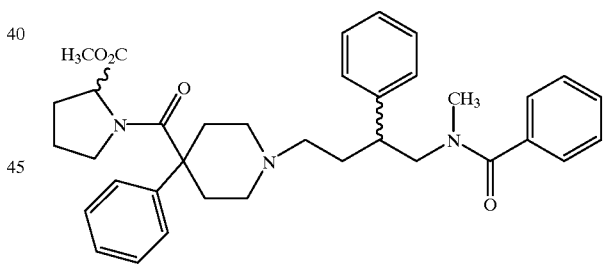

8.1 Synthesis of 2-phenyl-4-(t-butyldimethylsilyloxy) butyronitrile

Prepare by the method of Example 5.1.1 using phenylacetonitrile and 1-(t-butyldimethylsilyloxy)-2-bromoethane to give of the title compound.

8.2 Synthesis of 2-phenyl-4-(t-butyldimethylsilyloxy) butylamine

Prepare by the method of Example 5.2 using 2-phenyl-4-(t-butyldimethylsilyloxy)butyronitrile to give the title compound.

8.3 Synthesis of N-(2-phenyl-4-(t-butyldimethylsilyloxy) butyl)benzamide

Prepare by the method of Example 5.3 using 2-phenyl-4-(t-butyldimethylsilyloxy)butylamine and benzoyl chloride to give the title compound.

8.4 Synthesis of N-methyl-N-(2-phenyl-4-(t-butyldimethylsilyloxy)butyl)benzamide Prepare by the method of Example 5.4 using N-(2-phenyl-4-(t-butyldimethylsilyloxy)butyl)benzamide to give the title compound.

8.5 Synthesis of N-methyl-N-(2-phenyl-4-hydroxybutyl)benzamide

Prepare by the method of Example 5.5 using N-methyl-N-(2-phenyl-4-(t-butyldimethylsilyloxy)butyl)benzamide to give the title compound.

8.6 Synthesis of N-methyl-N-(2-phenyl-4-methanesulfonylbutyl)benzamide

Prepare by the method of Example 5.6 using N-methyl-N-(2-phenyl-4-hydroxybutyl)benzamide and methanesulfonyl chloride to give the title compound.

8.7 Synthesis of N-methyl-N-(4-phenyl-4-((4-phenyl-4-((2-carbomethoxypyrrolidin-1-yl)carboxamido)piperidin-1-yl)2-phenylbutyl)benzamide Prepare by the method of Example 5.7 using N-methyl-N-(2-phenyl-4-methanesulfonylbutyl)benzamide and 4-phenyl-4-((2-carbomethoxypyrrolidin-1-yl)carboxamido) piperidine hydrochloric acid salt to g1ve the title compound.

EXAMPLE 9

N-Methyl-N-(4-(4-phenyl-4-((2-carboethoxymorpholin-4-yl)carboxamido)piperidin-1-yl)-2-(3,4-dimethoxyphenyl)butyl)benzamide

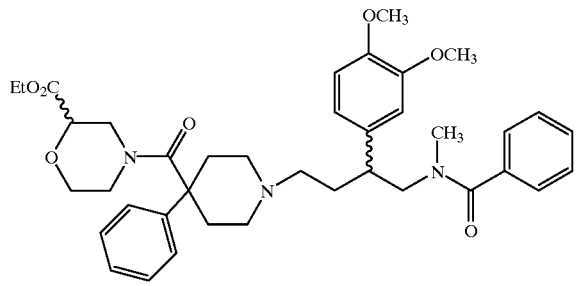

9.1 Synthesis of 2-(3,4-dimethoxyphenyl)-4-(t-butyldimethylsilyloxy)butyronitrile Prepare by the method of Example 5.1.1 using 3,4-dimethoxyphenylacetonitrile and 1-(t-butyldimethylsilyloxy)-2-bromoethane to give of the title compound.

9.2 Synthesis of 2-(3,4-dimethoxyphenyl)-4-(t-butyldimethylsilyloxy)butylamine

Prepare by the method of Example 5.2 using 2-(3,4-dimethoxyphenyl)-4-(t-butyldimethylsilyloxy)butyronitrile to give the title compound.

9.3 Synthesis of N-(2-(3,4-dimethoxyphenyl)-4-(t-butyldimethylsilyloxy)butyl)benzamide Prepare by the method of Example 5.3 using 2-(3,4-dimethoxyphenyl)-4-(t-butyldimethylsilyloxy)butylamine and benzoyl chloride to give the title compound.

9.4 Synthesis of N-methyl-N-(2-(3,4-dimethoxyphenyl)-4-(t-butyldimethylsilyloxy)butyl)benzamide Prepare by the method of Example 5.4 using N-(2-(3,4-dimethoxyphenyl)-4-(t-butyldimethylsilyloxy)butyl)benzamide to give the title compound.

9.5 Synthesis of N-methyl-N-(2-(3,4-dimethoxyphenyl)-4-hydroxybutyl)benzamide

Prepare by the method of Example 5.5 using N-methyl-N-(2-(3,4-dimethoxyphenyl)-4-(t-butyldimethylsilyloxy)butyl) benzamide to give the title compound.

9.6 Synthesis of N-methyl-N-(2-(3,4-dimethoxyphenyl)-4-methanesulfonylbutyl)benzamide Prepare by the method of Example 5.6 using N-methyl-N-(2-(3,4-dimethoxyphenyl)-4-hydroxybutyl)benzamide and methanesulfonyl chloride to give the title compound.

9.7 Synthesis of N-methyl-N-(4-(4-phenyl-4-((2-carboethoxymorpholin-4-yl)carboxamido)piperidin-1-yl)-2-(3,4-dimethoxyphenyl)-butyl)benzamide Prepare by the method of Example 5.7 using N-methyl-N-(2-(3,4-dimethoxyphenyl)-4-methanesulfonylbutyl) benzamide and 4-phenyl-4-((2-carboethoxymorpholin-4-yl) carboxamido) piperidine hydrochloric acid salt to give the title compound.

PREPARATION 12

(S)-N-Methyl-N-(2-(3,4-dichlorophenyl)-4-oxobutyl)-3,4,5-trimethoxybenzamide

Combine (S)-N-methyl-2-(3,4-dichlorophenyl)pent-4-enyl)amine (0.83 g, 3.4 mmol) and sodium bicarbonate (1.4 g, 16.9 mmol) in acetone (15 mL)/water (15 mL). Cool in an ice bath. Add a solution of 3,4,5-trimethoxybenzyl chloride (1.09 g, 4.72 mmol) in tetrahydrofuran (5 mL). After 18 hours, filter, rinse with ethyl acetate (250 mL). Separate the filtrate into layers and extract the organic layer with a saturated aqueous sodium bicarbonate solution. Dry the organic layer over MgSO$_4$, filter, and evaporate in vacuo to give a residue. Chromatograph the residue on silica gel eluting sequentially with 10% ethyl acetate/hexane, 20% ethyl acetate/hexane, 30% ethyl acetate/hexane, 40% ethyl acetate/hexane, and 50% ethyl acetate/hexane to give (S)-N-methyl-N-(2-(3,4-dichlorophenyl)pent-4-enyl)-3,4,5-trimethoxybenzamide: R$_f$=0.22 (silica gel, 50% ethyl acetate/hexane).

Combine (S)-N-methyl-N-(2-(3,4-dichlorophenyl)pent-4-enyl)-3,4,5-trimethoxybenzamide (1.39 g, 3.17 mmol), acetone/t-butanol/water (2/1/1, 32 mL), and a solution of N-methylmorpholine N-oxide (0.89 g 50% in water, 1.2). Add a solution of osmium tetraoxide (1.2 g, 4% in water, 0.06 mmol). After 2 hours, evaporate in vacuo to remove most of the acetone and partition the evaporated reaction mixture between dichloromethane and an aqueous 10% solution of sodium thiosulfate. Separate the layers, extract the organic layer with brine, dry over MgSO$_4$, filter, and evaporate in vacuo to give a residue: R$_f$=0.26 (sliica gel, 6% methanol/dichloromethane). Combine the residue and tetrahydrofuran/water (4/1 40 mL). Add sodium meta-periodate (0.81 g, 3.8 mmol). After 1.5 hours, filter the reaction mixture, rinse the solids with tetrahydrofuran, and evaporate the filtrate to remove most of the tetrahydrofuran. Dilute the evaporated reaction mixture with dichlromethane. Extract with water, dry over MgSO$_4$, filter, and evaporate in vacuo to give a residue. Chromatograph the residue on silica gel eluting with 1% methanol/dichloromethane to give the title compound.

PREPARATION 13

4-Phenyl-4-((4-carboethoxymethylpiperazin-1-yl)carboxamido)piperidine hydrochloric acid salt Combine 1-t-butoxycarbonyl-4-phenyl-4-((4-carboethoxymethylpiperazin-1-yl))carboxamido) piperidine (37.5 g, 78 mmol) and dichloromethane (300 mL). Add a solution of hydrochloric acid in dioxane (70 mL, 4 M, 280 mmol). After 5 hours, add diethyl ether and continue stirring to give a solid. Collect the solid, rinse with diethyl ether, and dry to give the title compound.

EXAMPLE 10

(S)-N-Methyl-N-(4-(4-phenyl-4-((4-carboethoxymethylpiperazin-1-yl)carboxamido)piperidin-yl)-2-(3,4-dichlorophenyl)butyl)-3,4,5-trimethoxybenzamide

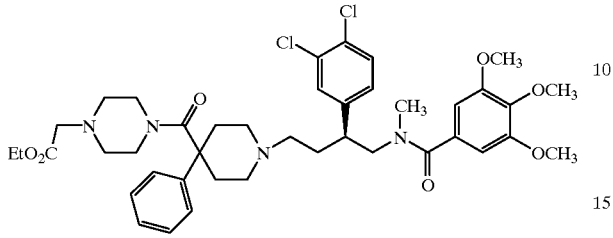

10.1 Synthesis of (S)-N-methyl-N-(4-(4-phenyl-4-((4-carboethoxymethylpiperazin-1-yl)carboxamido)piperidi-1-yl)-2-(3,4-dichlorophenyl)butyl) 3,4,5-trimethoxybenzamide Prepare by the method of Example 1.1 using (S)-N-methyl-N-(2-(3,4-dichlorophenyl)-4-oxobutyl)-3,4,5-trimethoxybenzamide and 4-phenyl-4-((4-carboethoxymethylpiperazin-1-yl) carboxamido)piperidine hydriodic acid salt to give the title compound.

EXAMPLE 11

N-Methyl-N-(4-(4-carboethxymethylpiperazin-1-yl)carboxamido)piperidin-1-yl)-2-(naphth-2-yl)butyl)benzamide

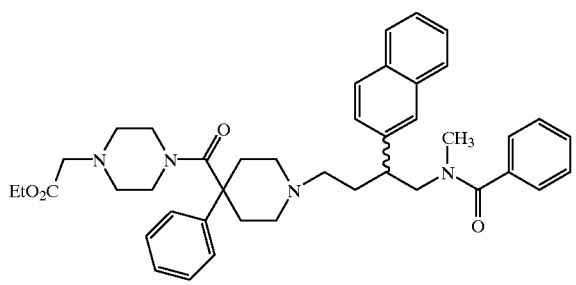

11.1 Synthesis of 2-(naphth-2-yl)-4-(t-butyldimethylsilyloxy)butyronitrile

Prepare by the method of Example 5.1.1 using naphth-2-ylacetonitrile and 1-(t-butyldimethylsilyloxy)-2-bromoethane to give of the title compound.

11.2 Synthesis of 2-(naphth-2-yl)-4-(t-butyldimethylsilyloxy)butylamine

Prepare by the method of Example 5.2 using 2-(naphth-2-yl)-4-(t-butyldimethylsilyloxy)butyronitrile to give the title compound.

11.3 Synthesis of N-(2-(naphth-2-yl)-4-(t-butyldimethylsilyloxy)butyl)benzamide

Prepare by the method of Example 5.3 using 2-(naphth-2-yl)-4-(t-butyldimethylsilyloxy)butylamine and benzoyl chloride to give the title compound.

11.4 Synthesis of N-methyl-N-(2-(naphth-2-yl)-4-(t-butyldimethylsilyloxy)butyl)benzamide Prepare by the method of Example 5.4 using N-(2-(naphth-2-yl)-4-(t-butyldimethylsilyloxy)butyl)benzamide to give the title compound.

11.5 Synthesis of N-methyl-N-(2-(naphth-2-yl)-4-hydroxybutyl)benzamide

Prepare by the method of Example 5.5 using N-methyl-N-(2-(naphth-2-yl)-4-(t-butyldimethylsilyloxy)butyl)benzamide to give the title compound.

11.6 Synthesis of N-methyl-N-(2-(naphth-2-yl)-4-methanesulfonylbutyl)benzamide

Prepare by the method of Example 5.6 using N-methyl-N-(2-(naphth-2-yl)-4-hydroxybutyl)benzamide and methanesulfonyl chloride to give the title compound.

11.7 Synthesis of N-methyl-N-(4-carboethoxymethylpiperazin-1-yl)carboxamido)piperidin-1-yl)-2-(naphth-2-yl)butyl)benzamide Prepare by the method of Example 5.7 using N-methyl-N-(2-(naphth-2-yl)-4-methanesulfonylbutyl)benzamide and 4-carboethxymethylpiperazin-1-yl)carboxamido)piperidine hydrochloric acid salt to give the title compound.

EXAMPLE 12

N-Methyl-N-(4-(4-phenyl-4-((4-carboethxymethylpiperazin-1-yl)carboxamido)piperidin-1-yl)-2-(thien-2-yl)butyl)-3,4,5-trimethoxybenzamide

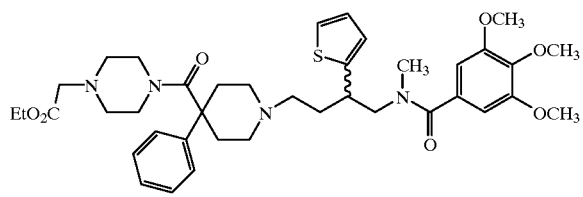

12.1 Synthesis of 2-(thien-2-yl)-4-(t-butyldimethylsilyloxy)butyronitrile

Prepare by the method of Example 5.1.1 using thien-2-ylacetonitrile and 1-(t-butyldimethylsilyloxy)-2-bromoethane to give of the title compound.

12.2 Synthesis of 2-(thien-2-yl)-4-(t-butyldimethylsilyloxy)butylamine

Combine 2-(thien-2-yl)-4-(t-butyldimethylsilyloxy)butyronitrile (3.24 mmol) and cobalt(II)chloride hexahydrate (1.54 g, 6.48 mmol) in methanol (50 mL). While maintaining the temperature at or below 20° C. with an ice-bath, add portionwise sodium borohydride (2.17 g, 57 mmol). After the addition is complete, allow the reaction mixture to stand at ambient temperature for 18 hours. Evaporate the reaction mixture in vacuo to obtain a residue. Partition the residue between dichloromethane and a saturated aqueous solution of ammonium chloride. Adjust the pH of the aqueous layer to about 8 using a 1M aqueous solution of hydrochloric acid. Separate the layers and extract the aqueous layer several times with dichloromethane, combine the organic layers, dry over $Na_2SO_4$, filter, and concentrate in vacuo to give the title compound.

12.3 Synthesis of N-(2-(thien-2-yl)-4-(t-butyldimethylsilyloxy)butyl)-3,4,5-trimethoxybenzamide Prepare by the method of Example 5.3 using 2-(thien-2-yl)-4-(t-butyldimethylsilyloxy)butylamine and 3,4,5-trimethoxybenzoyl chloride to give the title compound.

12.4 Synthesis of N-methyl-N-(2-(thien-2-yl)-4-(t-butyldimethylsilyloxy)butyl)-3,4,5-trimethoxybenzamide Prepare by the method of Example 1.4 using N-(2-(thien-2-yl)-4-(t-butyldimethylsilyloxy)butyl)-3,4,5-trimethoxybenzamide to give the title compound.

12.5 Synthesis of N-methyl-N-(2-(thien-2-yl)-4-hydroxybutyl)-3,4,5-trimethoxybenzamide Prepare by the method of Example 5.5 using N-methyl-N-(2-(thien-2-yl)-4-(t-butyldimethylsilyloxy)butyl)-3,4,5-trimethoxybenzamide to give the title compound.

12.6 Synthesis of N-methyl-N-(2-(thien-2-yl)-4-methanesulfonylbutyl)-3,4,5-trimethoxybenzamide Prepare by the method of Example 5.6 using N-methyl-N-(2-(thien-2-yl)-4-hydroxybutyl)-3,4,5-trimethoxybenzamide and methanesulfonyl chloride to give the title compound.

12.7 Synthesis of N-methyl-N-(4-(4-phenyl-4-((4-carboethxymethylpiperazin-1-yl)carboxamido)piperidin-1-yl)-2-(thien-2-yl)butyl)-3,4,5-trimethoxybenzamide Prepare by the method of Example 5.7 using N-methyl-N-(2-(thien-2-yl)-4-methanesulfonylbutyl)-3,4,5-trimethoxybenzamide and 4-phenyl-4-((4-carboethoxymethylpiperazin- 1-yl)carboxamido)piperidine hydrochloric acid salt to give the title compound.

EXAMPLE 13

N-Methyl-N-(4-(4-phenyl-4-((4-carboethxymethylpiperazin-1-yl)carboxamido)piperidin-1-yl)-2-(pyrid-3-yl)butyl)-3,4,5-trimethoxybenzamide

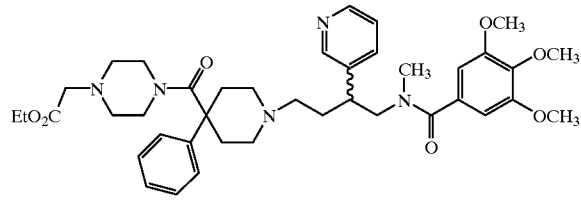

13.1 Synthesis of 2-(pyrid-3-yl)-4-(t-butyldimethylsilyloxy)butyronitrile

Prepare by the method of Example 5.1.2 wing pyrid-3-ylacetonitrile and 1-(t-butyldimethylsilyloxy)-2-bromoethane to give of the title compound.

13.2 Synthesis of 2-(pyrid-3-yl)-4-(t-butyldimethylsilyloxy)butylamine

Prepare by the method of Example 12.2 using 2-(pyrid-3-yl)-4-(t-butyldimethylsilyloxy)butyronitrile to give the title compound.

13.3 Synthesis of N-(2-(pyrid-3-yl)-4-(t-butyldimethylsilyloxy)butyl)-3,4,5-trimethoxybenzamide Prepare by the method of Example 5.3 using 2-(pyrid-3-yl)-4-(t-butyldimethylsilyloxy)butylamine and 3,4,5-trimethoxybenzoyl chloride to give the title compound.

13.4 Synthesis of N-methyl-N-(2-(pyrid-3-yl)-4-(t-butyldimethylsilyloxy)butyl)-3,4,5-trimethoxybenzamide Prepare by the method of Example 5.4 using N-(2-(pyrid-3-yl)-4-(t-butyldimethylsilyloxy)butyl)-3,4,5-trimethoxybenzamide to give the title compound.

13.5 Synthesis of N-methyl-N-(2-(pyrid-3-yl)-4-hydroxybutyl)-3,4,5-trimethoxybenzamide Prepare by the method of Example 5.5 using N-methyl-N-(2-(pyrid-3-yl)-4-(t-butyldimethylsilyloxy)butyl)-3,4,5-trimethoxybenzamide to give the title compound.

13.6 Synthesis of N-methyl-N-(2-(pyrid-3-yl)-4-methanesulfonylbutyl)-3,4,5-trimethoxybenzamide Prepare by the method of Example 5.6 using N-methyl-N-(2-(pyrid-3-yl)-4-hydroxybutyl)-3,4,5-trimethoxybenzamide and methanesulfonyl chloride. Isolate by extraction using a saturated solution of sodium bicarbonate to give the title compound.

13.7 Synthesis of N-methyl-N-(4-(4-phenyl-4-((4-carboethxymethylpiperazin-1-yl)carboxamido)piperidin-1-yl)-2-(pyrid-3-yl)butyl)-3,4,5-trimethoxybenzamide Prepare by the method of Example 5.7 using N-methyl-N-(2-(pyrid-3-yl)-4-methanesulfonylbutyl)-3,4,5-trimethoxybenzamide and 4-phenyl-4-((4-carboethoxymethylpiperazin-1-yl)carboxamido)piperidine hydrochloric acid salt to give the title compound.

EXAMPLE 14

N-Methyl-N-(4-(4-phenyl-4-((4-carboethxymethylpiperazin-1-yl)carboxamido)piperidin-1-yl)-2-(4-chlorophenyl)butyl)-3,4,5-trimethoxybenzamide

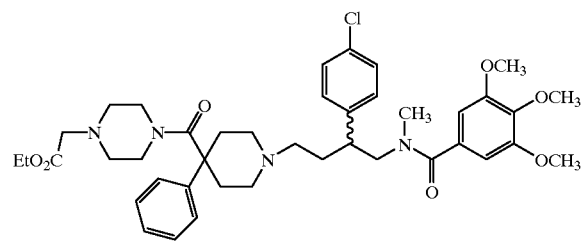

14.1 Synthesis of 2-(4-chlorophenyl)-4-(t-butyldimethylsilyloxy)butyronitrile

Prepare by the method of Example 5.1.1 using 4-chlorophenylacetonitrile and 1-(t-butyldimethylsilyloxy)-2-bromoethane to give the title compound.

14.2 Synthesis of 2-(4-chlorophenyl)-4-(t-butyldimethylsilyloxy)butylamine

Prepare by the method of Example 5.2 using 2-(4-chlorophenyl)-4-(t-butyldimethylsilyloxy)butyronitrile to give the title compound.

14.3 Synthesis of N-(2-(4-chlorophenyl)-4-(t-butyldimethylsilyloxy)butyl)-3,4,5-trimethoxybenzamide Prepare by the method of Example 5.3 using 2-(4-chlorophenyl)-4-(t-butyldimethylsilyloxy)butylamine and 3,4,5-trimethoxybenzoyl chloride to give the title compound.

14.4 Synthesis of N-methyl-N-(2-(4-chlorophenyl)-4-(t-butyldimethylsilyloxy)butyl)-3,4,5-trimethoxybenzamide Prepare by the method of Example 5.4 using N-(2-(4-chlorophenyl)-4-(t-butyldimethylsilyloxy)butyl)-3,4,5-trimethoxybenzamide to give the title compound.

14.5 Synthesis of N-methyl-N-(2-(4-chlorophenyl)-4-hydroxybutyl)-3,4,5-trimethoxybenzamide Prepare by the method of Example 5.5 using N-methyl-N-(2-(4-chlorophenyl)-4-(t-butyldimethylsilyloxy)butyl)-3,4,5-trimethoxybenzamide to give the title compound.

14.6 Synthesis of N-methyl-N-(2-(4-chlorophenyl)-4-methanesulfonylbutyl)-3,4,5-trimethoxybenzamide Prepare by the method of Example 5.6 using N-methyl-N-(2-(4-chlorophenyl)-4-hydroxybutyl)-3,4,5-trimethoxybenzamide to give the title compound.

14.7 Synthesis of N-methyl-N-(4-(4-phenyl-4-((4-carboethoxymethylpiperazin-1-)-2-(4-chlorophenyl)butyl)-3,4,5-trimethoxybenzamide Prepare by the method of Example 5.7 using N-methyl-N-(2-(4-chlorophenyl)-4-methanesulfonylbutyl)-3,4,5-trimethoxybenzamide and 4-phenyl-4-((4-carboethoxymethylpiperazin-1-yl)carboxamido)piperidine hydrochloric acid salt to give the title compound.

EXAMPLE 15

N-Methyl-N-(4-(4-phenyl-4-((4-carboethxymethylpiperazin-1-yl)carboxamido)piperidin-1-yl)-2-(3,4-dimethylphenyl)butyl)-3,4,5-trimethoxybenzamide

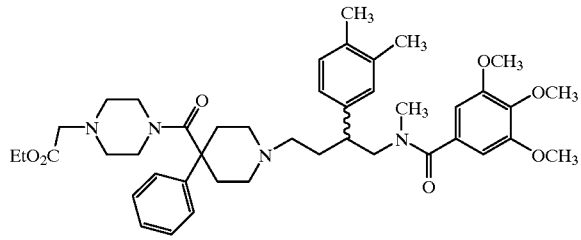

15.1 Synthesis of 2-(3,4-dimethylphenyl)-4-(t-butyldimethylsilyloxy)butyronitrile Prepare by the method of Example 5.1.1 using 3,4-dimethylphenylacetonitrile and 1-(t-butyldimethylsilyloxy)-2-bromoethane to give the title compound.

15.2 Synthesis of 2-(3,4-dimethylphenyl)-4-(t-butyldimethylsilyloxy)butylamine

Prepare by the method of Example 5.2 using 2-(3,4-dimethylphenyl)-4-(t-butyldimethylsilyloxy)butyronitrile to give the title compound.

15.3 Synthesis of N-(2-(3,4-dimethylphenyl)-4-(t-butyldimethylsilyloxy)butyl)-3,4,5-trimethoxybenzamide Prepare by the method of Example 5.3 using 2-(3,4-dimethylphenyl)-4-(t-butyldimethylsilyloxy)butylamine and 3,4,5-trimethoxybenzoyl chloride to give the title compound.

15.4 Synthesis of N-methyl-N-(2-(3,4-dimethylphenyl)-4-(t-butyldimethylsilyloxy)butyl)-3,4,5-trimethoxybenzamide Prepare by the method of Example 5.4 using N-(2-(3,4-dimethylphenyl)-4-(t-butyldimethylsilyloxy)butyl)-3,4,5-trimethoxybenzamide to give the title compound.

15.5 Synthesis of N-methyl-N-(2-(3,4-dimethylphenyl)-4-hydroxybutyl)-3,4,5-trimethoxybenzamide Prepare by the method of Example 5.5 using N-methyl-N-(2-(3,4-dimethylphenyl)-4-(t-butyldimethylsilyloxy)butyl)-3,4,5-trimethoxybenzamide to give the title compound.

15.6 Synthesis of N-methyl-N-(2-(3,4-dimethylphenyl)-4-methanesulfonylbutyl)-3,4,5-trimethoxybenzamide Prepare by the method of Example 5.6 using N-methyl-N-(2-(3,4-dimethylphenyl)-4-hydroxybutyl)-3,4,5-trimethoxybenzamide to give the title compound.

15.7 Synthesis of N-methyl-N-(4-(4-phenyl-4-((4-carboethoxymethylpiperazin-1-)-2-(3,4-dimethylphenyl)butyl)-3,4,5-trimethoxybenzamide Prepare by the method of Example 5.7 using N-methyl-N-(2-(3,4-dimethylphenyl)-4-methanesulfonylbutyl)-3,4,5-trimethoxybenzamide and 4-phenyl-4-((4-carboethoxymethylpiperazin-1-yl)carboxamido)piperidine hydrochloric acid salt to give the title compound.

PREPARATION 14

Synthesis of 2-methoxy-5-(4H-triazol-4-yl)benzoyl chloride

According to the method of *J. Chem. Soc.* (C), 1664 (1967), combine methyl 2-methoxy-5-aminobenzoate (2.0 g, 11 mmol), N,N-dimethylformamide azine (1.56 g, 11 mmol), p-toluenesulfonic acid (190 mg) in toluene (25 mL). Fit the reaction vessel with a gas inlet such that the head space of the vessel is swept with argon and scrub the effluent through dilute aqueous hydrochloric acid solution. Heat to reflux. After 20 hours, concentrate the reaction mixture in vacuo to give a residue. Partition the residue between dichloromethane and a saturated aqueous sodium bicarbonate solution. Extract the aqueous layer twice with dichloromethane. Combine the organic layers, dry over MgSO$_4$, filter, and evaporate in vacuo to give a residue. Chromatograph the residue on silica gel eluting sequentially with 70% ethyl acetate/dichloromethane and then 5% methanol/dichloromethane to give a residue. Recrystallize the residue form ethyl acetate/hexane to give methyl 2-methoxy-5-(4H-triazol-4-yl)benzoate: mp; 191–195.5° C. Alternately, according to the method of *J. Med. Chem.*, 21, 1100 (1978), combine methyl 2-methoxy-5-aminobenzoate (1.8 g, 10 mmol), diformyl hydrazine (0.97 g, 11 mmol), and phosphorous pentoxide (1.84 g, 13 mmol). Heat to 160° C. After 1.5 hours, cool the reaction mixture and add a saturated aqueous solution of sodium bicarbonate. Extract three times with dichloromethane. Dry the combined organic layers over MgSO$_4$, filter, and evaporate in vacuo to give a residue. Chromatograph the residue on silica gel eluting sequentially with 40% ethyl acetate/dichloromethane and then 5% methanol/dichloromethane to give methyl 2-methoxy-5-(4H-triazol-4-yl)benzoate: mp; 179–182° C.

Combine methyl 2-methoxy-5-(4H-triazol-4-yl)benzoate (56 mmol) and methanol (200 mL) and water (50 mL). Add 1 M aqueous solution of sodium hydroxide (62.5 mL, 62.5 mmol). Heat to reflux. After 8 hour, concentrate in vacuo to remove most of the solvent. Adjust the pH to about 1 to 2 using a 1 M aqueous hydrochloric acid solution, extract with dichloromethane. Dry the organic layer over MgSO$_4$, filter, and evaporate in vacuo to give 2-methoxy-5-(4H-triazol-4-yl)benzoic acid.

Combine 2-methoxy-5-(4H-triazol-4-yl)benzoic acid (5 mmol) and dichloromethane (40 mL). Add dropwise oxalyl chloride (0.72 mL, 8.25 mmol) followed by dimethylformamide (3 drops). After 4 hours, evaporate in vacuo and dry to give the title compound.

PREPARATION 15

Synthesis of (S)-N-methyl-N-(2-phenyl-4-oxobutyl)-2-methoxy-5-(4H-triazol-4-yl)benzamide Combine N-methyl-(2-phenylpent-4-enyl)amine (1.00 g, 5.7 mmol), acetone (50 mL), water (20 mL), and sodium bicarbonate (0.3 g, 2.85 mmol). Add portionwise, a solution of 2-methoxy-5-(4H-triazol-4-yl)benzoyl chloride (1.4 g, 6.3 mmol) in acetone (50 mL). After 10 hours, dilute the reaction mixture with a saturated aqueous sodium bicarbonate solution and evaporate in vacuo to remove most of the acetone. Extract five times with dichloromethane. Dry the combined organic layers over Na$_2$SO$_4$, filter, and evaporate in vacuo to give a residue. Chromatograph the residue on silica gel eluting with 5% methanol/dichloromethane to give (S)-N-methyl-N-(2-phenylpent-4-enyl)-2-methoxy-5-(4H-triazol-4-yl)benzamide: R$_f$=0.25 (silica gel, 5% methanol/dichloromethane).

Combine (S)-N-methyl-N-(2-phenylpent-4-enyl)-2-methoxy-5-(4H-triazol-4-yl)benzamide (1.03 g, 2.74 mmol), acetone (15 mL, t-butanol (7.5 mL), water (7.5 mL), and a solution of N-methylmorpholine N-oxide (0.74 mL, 50% in water, 3.56 mmol). Add a solution of osmium tetraoxide (1.0 mL, 4% in water). After 36 hours, evaporate in vacuo to remove most of the acetone and extract the evaporated reaction mixture with dichloromethane. Extract the organic layer with an aqueous 10% solution of sodium thiosulfate. Extract the aqueous layer five times with dichloromethane. Dry the combined organic layers over Na$_2$SO$_4$, filter, and evaporate in vacuo to give a residue. Combine the residue and tetrahydrofuran/water (20 mL, 4/1). Add sodium metaperiodate (0.7 g, 3.29 mmol). After 25 minutes, filter the reaction mixture, rinse the solids with tetrahydrofuran, and evaporate the filtrate to obtain a residue. Dilute the residue with dichloromethane (100 mL), extract with water, dry over MgSO$_4$, filter, and evaporate in vacuo to give a residue. Chromatograph the residue on silica gel eluting with 10% methanol/dichloromethane to give the title compound.

EXAMPLE 16

(S)-N-Methyl-N-(4-(4-phenyl-4-((4-carboethoxymethylpiperazin-1-yl)carboxamido) piperidin-1-yl)-2-phenylbutyl)-2-methoxy-5-(4H-triazol-4-yl)benzamide

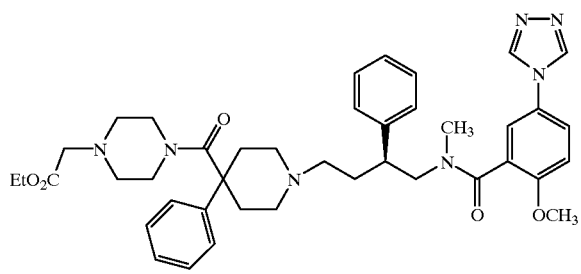

16.1 Synthesis of (S)-N-Methyl-N-(4-(4-phenyl-4-((4-carboethoxymethylpiperazin-1-yl)carboxamido)piperidin-1-yl)-2-phenylbutyl)-2-methoxy-5-(4H-triazol-4-yl) benzamide Prepare by the method of Example 1.1 using (S)-N-methyl-N-(2-phenyl-4-oxobutyl)-2-methoxy-5-(4H-triazol-4-yl)benzamide and 4-phenyl-4-((4-carboethoxymethylpiperazin-1-yl)carboxamido)piperidine hydriodic acid salt to give the title compound.

PREPAPATION 16

4-Phenyl-4-((4-carboethoxyethylpiperazin-1-yl) carboxamido)piperidine hydriodic acid salt Combine t-butyl 1-piperazinecarboxylate (10.47 g, 56.2 mmol), ethyl acrylate (8 mL) in ethanol (30 mL). Heat at reflux. After 5.5. hours, cool the reaction mixture and evaporate in vacuo to give a residue. Combine the residue and diethyl ether (200 mL) and extract with a 1 M aqueous solution of hydrochloric acid. Adjust the pH of the aqueous layer to basic using sodium bicarbonate and then extract with ethyl acetate. Dry the organic layer over MgSO$_4$, filter, and evaporate in vacuo to give t-butyl 4-carboethoxyethyl-1-piperazinecaboxylate.

Combine t-butyl 4-carboethoxyethyl-1-piperazinecaboxylate (14.3 g, 50 mmol) and dichloromethane (250 mL). Stir, cool to about 0° C. and purge with hydrochloric acid gas. After 4 hours, concentrate the reaction mixture in vacuo, twice add diethyl ether (200 mL) and evaporate in vacuo to give a solid. Triturate the solid with diethyl ether and collect by filtration to give 4-carboethoxyethyl-1-piperazine hydrochloric acid salt.

Combine 4-carboethoxyethyl-1-piperazine hydrochloric acid salt (6.8 g, 26.2 mmol), 1-t-butoxycarbonyl-4-phenyl-piperidine-4-carboxylic acid (8.0 g, 26.2 mmol), N,N-diisopropylethylamine (14 mL), and 1-hydroxybenzotriazole hydrate (3.9 g) in dichloromethane (250 mL). Add 1-(3-dimethylaminopropyl)-3-ethylcarbodiimide hydrochloride (5.53 9). After 17 hours, dilute the reaction mixture with dichloromethane (300 mL) and extract with a saturated aqueous solution of sodium bicarbonate, water, and then a 1 M aqueous solution of hydrochloric acid. Dry the organic layer over MgSO$_4$, filter, and evaporate in vacuo to give a residue. Chromatograph the residue on silica gel eluting sequentially with hexane, 20% ethyl acetate/hexane, 30% ethyl acetate/hexane, 50% ethyl acetate/hexane, 60% ethyl acetate/hexane, 50% ethyl acetate/hexane containing 2.0 mL of triethylamine, and then ethyl acetate to give 1-t-butoxycarbonyl-4-phenyl-4-((4-carboethoxyethylpiperazin-1-yl)carboxamido)piperidine.

Combine 1-t-butoxycarbonyl-4-phenyl-4-((4-carboethoxyethylpiperazin-1-yl)carboxamido)piperidine (7.3 g, 15.3 mmol) and dichloromethane (250 mL). Stir, cool to about 0° C. and purge with hydrochloric acid gas. After 2 hours, warm to ambient temperature and purge again with hydrochloric acid gas. After 3 hours, concentrate the reaction mixture in vacuo, three times add diethyl ether (50 mL) and evaporate in vacuo to give a solid. Combine the solid, dichloromethane (100 mL), and an aqueous solution of sodium bicarbonate. Separate the layers, saturate the aqueous layer with sodium chloride, and extract twice with dichloromethane. Combine the organic layers, dry over MgSO$_4$, filter, and evaporate in vacuo to give 4-phenyl-4-((4-carboethoxyethylpiperazin-1-yl)carboxamido) piperidine.

Combine 4-phenyl-4-((4-carboethoxyethylpiperazin-1-yl)carboxamido)piperidine (6.0 g) and ethanol (60 mL). Add an aqueous solution of hydriodic acid (7.9 g, 57%). After 30 minutes, add diethyl ether (200 mL) to give a solid. Filter, rinse the solid with diethyl ether, and dry to give the title compound.

EXAMPLE 17

N-Methyl-N-(4-(4-phenyl-4-((4-phenyl-4-carboethoxyethylpiperazin-1-yl)carboxamido) piperidin-1-yl)-2-(3,4-dichlorophenyl)butyl)-2-methoxy-5-(1H-tetrazol-1-yl)-benzamide

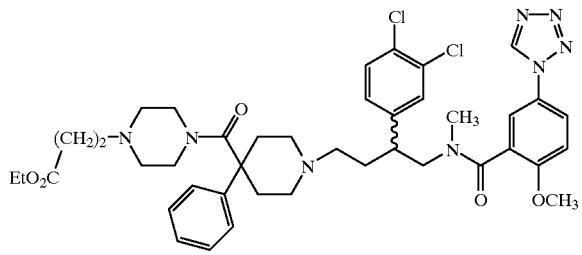

17.1 Synthesis of N-(2-(3,4-dichlorophenyl)-4-(tetrahydropyran-2-yloxy)butyl)-2-methoxy-5-(1H-tetrazol-1-yl)-benzamide Prepare by the method of Example 6.3 using 2-(3,4-dichlorophenyl)-4-(tetrahydropyran-2-yloxy) butylamine and 2-methoxy-5-(1H-tetrazol-1-yl)-benzoyl chloride to give the title compound.

17.2 Synthesis of N-methyl-N-(2-(3,4-dichlorophenyl)-4-(tetrahydropyran-2-yloxy )butyl)-2-methoxy-5-(1H-tetrazol-1-yl)-benzamide Prepare by the method of Example 6.4 using N-(2-(3,4-dichlorophenyl)-4-(tetrahydropyran-2-yloxy)butyl)2-methoxy-5-(1H-tetrazol-1-yl)-benzamide to give the title compound.

17.3 Synthesis of N-methyl-N-(2-(3,4-dichlorophenyl)-4-hydroxybutyl)2-methoxy-5-(1H-tetrazol-1-yl)-benzamide Prepare by the method of Example 6.5 using N-methyl-N-(2-(3,4-dichlorophenyl)-4-(tetrahydropyran-2-yloxy)butyl)2-methoxy-5-(1H-tetrazol-1-yl)-benzamide to give the title compound.

17.4 Synthesis of N-methyl-N-(2-(3,4-dichlorophenyl)-4-methanesulfonylbutyl)2-methoxy-5-(1H-tetrazol-1-yl)-benzamide Prepare by the method of Example 6.6 using N-methyl-N-(2-(3,4-dichlorophenyl)-4-hydroxybutyl)2-methoxy-5-(1H-tetrazol-1-yl)-benzamide to obtain the title compound.

17.5 Synthesis of N-methyl-N-(4-(4-phenyl-4-carboethoxyethylpiperazin-1-yl)carboxamido)piperidin-1-yl)-2-(3,4-dichlorophenyl)butyl)-2-methoxy-5-(1H-tetrazol-1-yl)-benzamide Combine N-methyl-N-(2-(3,4-dichlorophenyl)-4-methanesulfonylbutyl)2-methoxy-5-(1H-tetrazol-1-yl)-benzamide (1.8 g, 6.6 mmol), 4-phenyl-4-carboethoxyethylpiperazin-1-yl)carboxamido)piperidine hydriodic acid (4.0 g, 6.36 mmol) and triethylamine (2.7 mL) in acetonitrile (40 mL). Heat to reflux. After 12 hours cool the reaction mixture, concentrate in vacuo, and dilute the evaporated reaction mixture with dichloromethane (200 mL). Extract with saturated aqueous sodium bicarbonate and then water. Dry the organic layer over MgSO$_4$, filter, and evaporate in vacuo to give the title compound.

PREPARATION 17

4-(Pyrid-3-yl)-4-((4-carboethoxymethylpiperazin-1-yl)carboxamido)piperidine

Combine N-benzyl-N-bis-(2-chloroethyl)amine hydrochloride (72.0 g, 269 mmol) and pyrid-3-ylacetonitrile (31.8 g, 269 mmol) and hexadecyltributylphosphonium bromide (6 g) in aqueous solution of sodium hydroxide (50% by weight, 400 mL). Heat on a steam bath and stir vigorously. After 1.5 hours, cool the reaction mixture to ambient temperature. Extract the reaction mixture three times with dichloromethane. Combine the organic layers and extract twice with an aqueous 10% hydrochloric acid solution. Combine the aqueous layers and make basic with an aqueous solution of sodium hydroxide (50% by weight). Extract the basified aqueous layer three times with diethyl ether. Dry the combined ether layers over MgSO$_4$ and filter to give a filtrate. Purge the filtrate with hydrogen chloride (gas) to give a solid. Collect the solid by filtration and dry in vacuo at 65° C. to give 1-benzyl-4-(pyrid-3-yl)-4-cyanopiperidine hydrochloric acid salt.

Combine 1-benzyl-4-(pyrid-3-yl)-4-cyanopiperidine hydrochloric acid salt (10.0 g, 28 mmol), sodium hydroxide (7.6 g, 190 mmol), and water (2 mL) in ethylene glycol (120 mL). Heat to reflux. After 15 hours, evaporate in vacuo to give a residue.

Combine the residue with methanol (20 mL) and ethanol (20 mL) and stir to give a solid. Filter to remove the solid. Add ethanol (50 mL) to the filtrate and stir for 1 hour to give a second solid. Remove the second solid by filtration and acidify the filtrate with aqueous 12 M hydrochloric acid solution. Evaporate the acidified filtrate in vacuo to give a residue. Combine the residue and dichloromethane. Extract with water. Adjust the pH of the aqueous layer to 7 using sodium bicarbonate. Evaporate the aqueous layer in vacuo to give a residue, combine the residue and ethanol and again evaporate in vacuo to give a residue. Combine the residue with methanol and heat to about 50° C. to give a slurry. Filter the slurry, add acetone (30 mL) to the filtrate to give a solid.

Collect the solid by filtration, rinse with acetone, and dry to give 1-benzyl-4-(pyrid-3-yl)-piperidine-4-carboxylic acid. Combine 1-benzyl-4-(pyrid-3-yl)-piperidine-4-carboxylic acid (5.1 g), 4-carboethoxymethylpiperazine (5.8 g), 1-(3-dimethylaminopropyl)-3-ethylcarbodiimide hydrochloride (5.0 g), and 1-hydroxybenzotriazole hydrate (3.6 g) in dimethylformamide (130 mL). After 60 hours, dilute the reaction mixture with ethyl acetate (1 L). Extract the diluted reaction mixture with a saturated aqueous solution of sodium bicarbonate. Dry the organic layer over MgSO$_4$, filter, and evaporate in vacuo to give a residue. Triturate the residue with diethyl ether, filter, and dry to give 1-benzyl-4-(pyrid-3-yl)-4-((4-carboethoxymethylpiperazin-1-yl)carboxamido)piperidine. R$_f$=0.52 (silica gel, dichloromethane/methanol/concentrated aqueous ammonia, 90/10/1).

Combine 1-benzyl-4-(pyrid-3-yl)-4-((4-carboethoxymethylpiperazin-1-yl)carboxamido)piperidine (1.9 g) and ethanol 9200 mL). Add 5% palladium-on-carbon (1.2 g). Hydrogenate on a pressure apparatus at 65 psi. After 17 hours, filter through celite to remove the catalyst and evaporate the filtrate in vacuo to give a residue. Chromatograph the residue on silica gel eluting sequentially with 98/2 dichloromethane/methanol, 96/4 dichloromethane/methanol, 94/6/0.6 dichloromethane/methanol/concentrated aqueous ammonia, and then 94/8/0.6 dichloromethane/methanol/ concentrated aqueous ammonia to give the title compound.

EXAMPLE 18

N-Methyl-N-(4-(4-phenyl-4-((4-(pyrid-3-yl)-4-carboethoxyethylpiperazin-1-yl)carboxamido)piperidin-1-yl)-2-(3,4-dichlorophenyl)butyl)-2-methoxy-5-(1H-tetrazol-1-yl)-benzamide

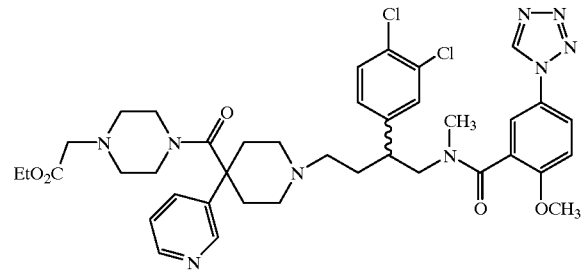

18.1 Synthesis of N-methyl-N-(4-(4-(pyrid-3-yl)-4-carboethoxyethylpiperazin-1-yl)carboxamido)piperidin-1-yl)-2-(3,4-dichlorophenyl)butyl)-2-methoxy-5-(1H-tetrazol-1-yl)-benzamide Combine N-methyl-N-(2-(3,4-dichlorophenyl)-4 methanesulfonylbutyl)2-methoxy-5-(1H-tetrazol-1-yl)-benzamide, (1.1 g), 4-(pyrid-3-yl)-4-((4-carboethoxymethylpiperazin-1yl-)carboxamido)piperidine (5.9 g), and N,N-diisopropylethylamine (1.53 g) in acetonitrile (40 mL). Heat to reflux. After 12 hours, evaporate in vacuo to give a residue. Chromatograph the residue on silica gel to give the title compound.

PREPARATION 18

Synthesis of 2-methoxy-5-(5-trifluoromethyl-1H-tetrazol-1-yl)benzoic acid

Combine methyl 2-methoxy-5-aminobenzoate (1.8 g, 10 mmol) and pyridine (0.88 mL, 11 mmol) in tetrahydrofuran (10 mL). Cool in an ice bath. Add trifluoroacetic anhydride (1.56 mL, 11 mmol). Warm to ambient temperature. After 2 hours, add water and dilute the reaction mixture with ethyl acetate. Separate the organic layer, extract with brine, dry over MgSO$_4$, filter; and evaporate in vacuo to give methyl 2-methoxy-5-trifluoroacetylamidobenzoate. Combine methyl 2-methoxy-5-trifluoroacetylamidobenzoate (3.1 g, 15 mmol), triphenylphosphine (5.2 g, 20 mmol) and carbon tetrachloride (30 mL) in tetrahydrofuran (30 mL). Heat to reflux. After 18 hours, add carbon tetrachloride (100 mL) and continue to heat at reflux. After 18 hours, evaporate in vacuo to give a residue. Chromatograph the residue on a short column of silica gel eluting with 30% ethyl acetate/hexane to give methyl 2-methoxy-5-(2-trifluoromethyl-2-chloroiminobenzoate.

Combine methyl 2-methoxy-5-(2-trifluoromethyl-2-chloroiminobenzoate (3.4 g, 12 mmol) and sodium azide (3.12 g, 48 mmol) in glacial acetic acid (60 mL). Heat to 70° C. After 3 hours, cool the reaction mixture in an ice bath, add water (800 mL), and stir to give a solid. After 1 hour, collect the solid by filtration and dry to give methyl 2-methoxy-5-(5-trifluoromethyl-1H-tetrazol-1-yl)benzoate: $R_f$=0.58 (silica gel, 30% ethyl acetate/toluene).

Combine methyl 2-methoxy-5-(5-trifluoromethyl-1H-tetrazol-1-yl)benzoate (1.46 g, 5.27 mmol) and an aqueous solution of sodium hydroxide (20 mL, 2 M, 40 mmol) in methanol/tetrahydrofuran (20 mL/10 mL). After 2 hours, adjust the pH of the reaction mixture to about 2 using a 1M aqueous hydrochloric acid solution. Extract the reaction mixture with ethyl acetate and then dichloromethane. Dry the combined organic layers over MgSO$_4$, filter, and evaporate in vacuo to give a the title compound: $R_f$=0.55 (silica gel, 85% chloroform/10% methanol/5% acetic acid).

PREPARATION 19

(S)-N-methyl-N-(2-(4-fluorophenyl)-4-oxobutyl)-2-methoxy-5-(5-trifluoromethyl-1H-tetrazol-1-yl)benzamide Combine N-methyl-2-(4-fluorophenyl)pent-4-enyl)amine (0.2 g, 1.0 mmol) and dichloromethane (10 mL). Add (5-trifluoromethyl-1H-tetrazol-1-yl)benzoic acid (1.0 mmol), 1-hydroxybenzotriazole hydrate (0.16 g, 1.2 mmol), N,N-diisopropylethylamine (0.17 mL, 1.0 mmol), and 1-ethyl-3-(3-dimethylaminopropyl)carbodiimide hydrochloride (0.23 g, 1.2 mmol). After 18 hours, dilute the reaction mixture with ethyl acetate and extract with brine. Dry the organic layer over Na$_2$SO$_4$, filter, and evaporate in vacuo to give a residue. Chromatograph the residue on silica gel to give (S)-N-methyl-N-(2-(4-fluorophenyl)pent-4-enyl)-2-methoxy-5-(5-trifluoromethyl-1H-tetrazol-1-yl)benzamide.

Combine (S)-N-methyl-N-(2-(4-fluorophenyl)pent-4-enyl)-2-methoxy-5-(5-trifluoromethyl-1H-tetrazol-1-yl)benzamide (10 mmol), acetone/t-butanol/water (2/1/1, 56 mL), and a solution of N-methylmorpholine N-oxide (2.6 mL, 50% in water, 12.7 mmol). Add a solution of osmium tetraoxide (2.6 mL, 4% in water, 0.44 mmol). After 3 hours, evaporate in vacuo to remove most of the acetone and partition the evaporated reaction mixture between dichloromethane and an aqueous 10% solution of sodium thiosulfate. Separate the layer, dry the organic layer over MgSO$_4$, filter, and evaporate in vacuo to give a residue. Combine the residue, tetrahydrofuran (70 mL), and water (17.5 mL). Add sodium meta-periodate (3.2 g). After 1.5 hours, filter the reaction mixture, rinse the solids with dichloromethane, and evaporate the filtrate give the title compound.

EXAMPLE 19

(S)-N-Methyl-N-(4-(4-phenyl-4-((4-carboethoxymethylpiperazin-1-yl)carboxamido)piperidin-1-yl)-2-(4-fluorophenyl)butyl)-2-methoxy-5-(5-trifluoromethyl-1H-tetrazol-1-yl)benzamide

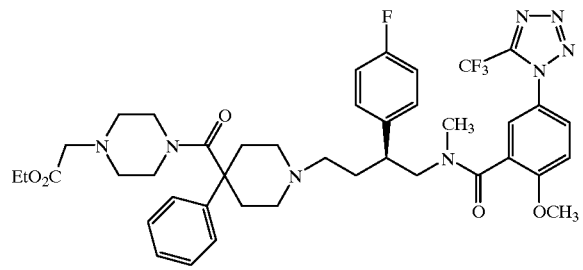

19.1 Synthesis of ((S)-N-methyl-N-(4-(4-phenyl-4-((4-carboethoxymethylpiperazin-1-yl)carboxamido)piperidin-1-yl)-2-(4-fluorophenyl)butyl)-2-methoxy-5-(5-trifluoromethyl-1H-tetrazol-1-yl)benzamide Prepare by the method of Example 1.1 using (S)-N-methyl-N-(2-(4-fluorophenyl)-4-oxobutyl)-2-methoxy-5-(5-trifluoromethyl-1H-tetrazol-1-yl)benzamide and 4-phenyl-4-((4-carboethoxymethylpiperazin-1-yl)carboxamido)piperidine hydriodic acid salt to give the title compound.

PREPARATION 20

4-Phenyl-4-((4-carboethoxypropylpiperazin-1-yl)carboxamido)piperidine hydriodic acid salt Combine t-butyl 1-piperazinecarboxylate (10.7 g, 57.5 mmol), ethyl 4-chlorobutyrate (10.4 mL), and potassium carbonate (8 g) in dimethylformamide (60 mL). Heat at reflux. After 4.5, hours, cool the reaction, dilute with an aqueous solution of sodium bicarbonate, and extract twice with diethyl ether (200 mL). Combine the organic layers and extract with a 1 M aqueous solution of hydrochloric acid. Adjust the pH of the aqueous layer to basic using sodium bicarbonate and then extract twice with diethyl ether. Dry the combined organic layers over MgSO$_4$, filter, and evaporate in vacuo to give a residue. Chromatograph the residue on silica gel eluting sequentially with 10% ethyl acetate/hexane, 20% ethyl acetate/hexane, 25% ethyl acetate/hexane to give t-butyl 4-carboethoxypropyl-1-piperazinecaboxylate. $R_f$=0.5 (silica gel, ethyl acetate).

Combine t-butyl 4-carboethoxypropyl-1-piperazinecaboxylate (7.0 g, 23.3 mmol) and dichloromethane (100 mL). Stir, cool to about 0° C. and purge with hydrochloric acid gas. After 2 hours, concentrate the reaction mixture in vacuo, twice add diethyl ether (50 mL) and evaporate in vacuo to give a solid. Triturate the solid with diethyl ether and collect by filtration to give 4-carboethoxypropyl-1-piperazine hydrochloric acid salt.

Combine 4-carboethoxypropyl-1-piperazine hydrochloric acid salt (5.6 g, 20.5 mmol), 1-t-butoxycarbonyl-4-phenylpiperidine-4-carboxylic acid (8.13 g, 26.6 mmol), N,N-diisopropylethylamine (7.9 g), and 1-hydroxybenzotriazole hydrate (3.3 g, 24.6 mmol) in dichloromethane (250 mL). Add 1-(3-dimethylaminopropyl)-3-ethylcarbodiimide hydrochloride (4.72 g, 24.6 mmol). After 24 hours, dilute the reaction mixture with dichloromethane (100 mL) and extract with a saturated aqueous solution of sodium bicarbonate and then a 1 M aqueous solution of hydrochloric acid. Dry the organic layer over MgSO$_4$, filter, and evaporate in vacuo to give residue. Chromatograph the residue on silica gel eluting sequentially with hexane, 20% ethyl acetate/hexane, 40% ethyl acetate/hexane, 60% ethyl acetate/hexane, 80% ethyl acetate/hexane, ethyl acetate, and then 6% methanol/ethyl acetate to give 1-t-butoxycarbonyl-4-phenyl-4-((4-carboethoxypropylpiperazin-1-yl)carboxamido)piperidine.

Combine 1-t-butoxycarbonyl-4-phenyl-4-((4-carboethoxypropylpiperazin-1-yl)carboxamido)piperidine (6.7 g, 12.5 mmol) and ethanol (90 mL). Add an aqueous solution of hydriodic acid (6.2 g, 57%). Heat at reflux. After 15 hours, cool to ambient temperature and add diethyl ether (300 mL) to give a solid. Filter, rinse the solid with diethyl ether, and dry to give the title compound.

EXAMPLE 20

N-Methyl-N-(4-(4-phenyl-4-((4-phenyl-4-carboethoxypropylpiperazin-1-yl) carboxamido) piperidin-1-yl)-2-(3,4-dichlorophenyl)butyl)-2-methoxy-5-(1H-tetrazol-1-yl)-benzamide

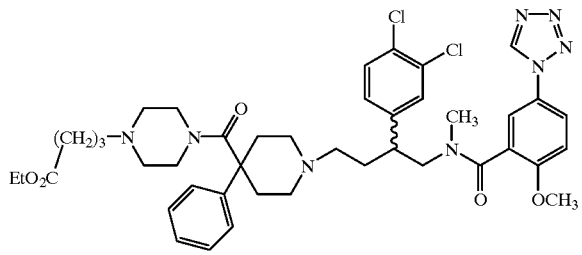

20.1 Synthesis of N-methyl-N-(4-(4-phenyl-4-carboethoxypropylpiperazin-1-yl)carboxamido)piperidin-1-yl)-2-(3,4-dichlorophenyl)butyl)-2-methoxy-5-(1H-tetrazol-1-yl)-benzamide Prepare by the method of Example 17.5 using N-methyl-N-(2-(3,4-dichlorophenyl)-4-methanesulfonylbutyl)2-methoxy-5-(1H-tetrazol-1-yl)-benzamide and 4-phenyl-4-carboethoxypropylpiperazin-1-yl)carboxamido)piperidine hydriodic acid to give the title compound.

The tachykinins are a class of neuropeptides which share a common C-terminus sequence, Phe-Xaa-Gly-Leu-Met-NH2. The tachykinins are widely distributed in the peripheral and central nervous systems where they bind to at least three receptors types. The NK$_1$, NK$_{21}$ and NK$_3$ receptors are defined by the preferred binding affinity of substance P, neurokinin A (NKA), and neurokinin B (NKB), respectively.

The use of tachykinin antagonists is indicated as therapy for a variety of tachykinin-mediated diseases and conditions including: cystitis; bronchoconstriction; hypersensitivity reactions; the treatment of pain; peripheral neuropathy; post-herpetic neuralgia; adverse immunological reactions; respiratory diseases, such as asthma, bronchitis, cough, rhinitis, and allergies and the like; opthalmic diseases, such as conjuctivitis and vernal conjuctivitis; cutaneous diseases, such as contact dermatitis, atopic dermatitis, and urticaria; inflammatory diseases, such as rheumatoid arthritis and osteoarthritis, and the like; gastrointestinal conditions, such as Crohn's disease, emesis, and ulcerative colitis; conditions due to vasodilation, such as angina and migraine; and central nervous system diseases and conditions, such as anxiety, depression, psychosis, schizophrenia, dementia.

It is understood that tachykinin-mediated diseases and conditions are those diseases and conditions in which the tachykinins are involved, either in whole or in part, in their clinical manifestation(s). Moreover, the tachykinins involvement is not necessarily causative of a particular tachykinin-mediated disease and condition. Tachykinin antagonists are useful in controlling or providing therapeutic relief of those tachykinin-mediated diseases and conditions.

The present invention provides new and useful tachykinin antagonists of formula (1), and stereoisomers and pharmaceutically acceptable salts thereof. Particularly, the present invention provides compounds of formula (1) which are NK$_1$ and NK$_2$ receptor antagonists.

In a further embodiment, the present invention provides a method of treating tachykinin-mediated diseases and conditions in a patient in need thereof comprising administering to said patient a therapeutically effective amount of a compound of formula (1). Various diseases and conditions described to be treated herein, are well known and appreciated by those skilled in the art. It is also recognized that one skilled in the art may affect the associated diseases and conditions by treating a patient presently afflicted with the diseases or conditions or by prophylactically treating a patient afflicted with the diseases or conditions with a therapeutically effective amount of the compounds of formula (1).

As used herein, the term "patient" refers to a warm blooded animal such as a mammal which is afflicted with a particular tachykinin-mediated disease or condition. It is understood that guinea pigs, dogs, cats, rats, mice, horses, cattle, sheep, and humans are examples of animals within the scope of the meaning of the term. A patient is in need of treatment for tachykinin-mediated diseases and conditions when the patient is inflicted within one or more of the diseases or conditions described herein.

The identification of those patients who are in need of treatment of a tachykinin-mediated disease or condition is well within the ability and knowledge of one skilled in the art. A clinician skilled in the art can readily identify, by the use of clinical tests, physical examination and medical/family history, those patients who are in need of such treatment.

As used herein, the term "therapeutically effective amount" of a compound of formula (1) refers to an amount which is effective in controlling tachykinin-mediated diseases and conditions. The term "controlling" is intended to refer to all processes wherein there may be a slowing, interrupting, arresting, or stopping of the progression of the diseases and conditions described herein, but does not necessarily indicate a total elimination of all disease and condition symptoms, and is intended to include prophylactic treatment of the tachykinin-mediated diseases and conditions.

A therapeutically effective amount can be readily determined by the attending diagnostician, as one skilled in the art, by the use of conventional techniques and by observing results obtained under analogous circumstances. In determining the therapeutically effective amount, the dose, a number of factors are considered by the attending diagnostician, including, but not limited to: the species of mammal; its size, age, and general health; the specific disease involved; the degree of involvement or the severity of the disease; the response of the individual patient; the particular compound administered; the mode of administration; the bioavailability characteristic of the preparation administered; the dose regimen selected; the use of concomitant medication; and other relevant circumstances.

A therapeutically effective amount of a compound of formula (1) is expected to vary from about 0.1 milligram per kilogram of body weight per day (mg/kg/day) to about 100 mg/kg/day. Preferred amounts are able to be determined by one skilled in the art.

In effecting treatment of a patient afflicted with tachykinin-mediated diseases and conditions described above, a compound of formula (1) can be administered in any form or mode which makes the compound bioavailable in an effective amount, including oral, inhalation, parenteral, and topical routes. For example, compounds of formula (1) can be administered orally, by inhalation of an aerosol or dry powder, subcutaneously, intramuscularly, intravenously, intranasally, rectally, transdermally, topically, and the like. Oral or inhalation administration is generally preferred for treatment of respiratory diseases and conditions, e.g. asthma, bronchitis, and cough. One skilled in the art of preparing formulations can readily select the proper form and mode of administration depending upon the particular characteristics of the compound selected, the disease or condition to be treated, the stage of the disease or condition, and other relevant circumstances. (Remington's Pharmaceutical Sciences, 18th Edition, Mack Publishing Co. (1990)).

The compounds of the present invention can be administered alone or in the form of a pharmaceutical composition in combination with pharmaceutically acceptable carriers or excipients, the proportion and nature of which are determined by the solubility and chemical properties of the compound selected, the chosen route of administration, and standard pharmaceutical practice. The compounds of the present invention, while effective themselves, may be formulated and administered in the form of their pharmaceutically acceptable salts, such as acid addition salts or base addition salts, for purposes of stability, convenience of crystallization, increased solubility and the like.

In another embodiment, the present invention provides pharmaceutical compositions comprising a therapeutically effective amount of a compound of formula (1) in admixture or otherwise in association with one or more pharmaceutically acceptable carriers or excipients.

The pharmaceutical compositions are prepared in a manner well known in the pharmaceutical art. The carrier or excipient may be a solid, semi-solid, or liquid material which can serve as a vehicle or medium for the active ingredient. Suitable carriers or excipients are well known in the art. The pharmaceutical composition may be adapted for oral, inhalation, parenteral, or topical use and may be administered to the patient in the form of tablets, capsules, aerosols, inhalants, suppositories, solution, suspensions, or the like.

The compounds of the present invention may be administered orally, for example, with an inert diluent or with an edible carrier. They may be enclosed in gelatin capsules or compressed into tablets. For the purpose of oral therapeutic administration, the compounds of formula (I) may be incorporated with excipients and used in the form of tablets, troches, capsules, elixirs, suspensions, syrups, wafers, chewing gums and the like. These preparations should contain at least 4% of the compound of Formula (I), the active ingredient, but may be varied depending upon the particular form and may conveniently be between 4% to about 70% of the weight of the unit. The amount of the active ingredient present in compositions is such that a unit dosage form suitable for administration will be obtained.

The tablets, pills, capsules, troches and the like may also contain one or more of the following adjuvants: binders such as microcrystalline cellulose, gum tragacanth or gelatin; excipients such as starch or lactose, disintegrating agents such as alginic acid, Primogel, corn starch and the like; lubricants such as magnesium stearate or Sterotex; glidants such as colloidal silicon dioxide; and sweetening agents such as sucrose or saccharin may be added or a flavoring agent such as peppermint, methyl salicylate or orange flavoring. When the dosage unit form is a capsule, it may contain, in addition to materials of the above type, a liquid carrier such as polyethylene glycol or a fatty oil. Other dosage unit forms may contain other various materials which modify the physical form of the dosage unit, for example, as coatings. Thus, tablets or pills may be coated with sugar, shellac, or other enteric coating agents. A syrup may contain, in addition to the present compounds, sucrose as a sweetening agent and certain preservatives, dyes and colorings and flavors. Materials used in preparing these various compositions should be pharmaceutically pure and non-toxic in the amounts used.

For the purpose of parenteral therapeutic administration, the compounds of the present invention may be incorporated into a solution or suspension. These preparations should contain at least 0.1% of a compound of the invention, but may be varied to be between 0.1% and about 50% of the weight thereof. The amount of the active ingredient present in such compositions is such that a suitable dosage will be obtained. Preferred compositions and preparations are able to be determined by one skilled in the art.

The solutions or suspensions may also include one or more of the following adjuvants: sterile diluents such as water for injection, saline solution, fixed oils, polyethylene glycols, glycerine, propylene glycol or other synthetic solvents; antibacterial agents such as benzyl alcohol or methyl paraben; antioxidants such as ascorbic acid or sodium bisulfite; chelating agents such as ethylene diaminetetraacetic acid; buffers such as acetates, citrates or phosphates and agents for the adjustment of toxicity such as sodium chloride or dextrose. The parenteral preparation can be enclosed in ampules, disposable syringes or multiple dose vials made of glass or plastic.

The compounds of the present invention may also be administered by inhalation, such as by aerosol or dry powder. Delivery may be by a liquefied or compressed gas or by a suitable pump system which dispenses the compounds of the present invention or a formulation thereof. Formulations for administration by inhalation of compounds of formula (1) may be delivered in single phase, bi-phasic, or tri-phasic systems. A variety of systems are available for the administration by aerosol of the compounds of formula (1). Dry powder formulations are prepared by either pelletizing or milling the compound of formula (1) to a suitable particle size or by admixing the pelletized or milled compound of formula (1) with a suitable carrier material, such as lactose and the like. Delivery by inhalation includes the necessary container, activators, valves, subcontainers, and the like. Preferred aerosol and dry powder formulations for administration by inhalation can be determined by one skilled in the art.

The compounds of the present invention may also be administered topically, and when done so the carrier may suitably comprise a solution, ointment or gel base. The base, for example, may comprise one or more of the following: petrolatum, lanolin, polyethylene glycols, bee wax, mineral oil, diluents such as water and alcohol, and emulsifiers and stabilizers. Topical formulations may contain a concentration of the formula (1) or its pharmaceutical salt from about 0.1 to about 10% w/v (weight per unit volume).

The tachykinin receptor antagonists of the present invention can be evalutated by the procedures that follow.

EXAMPLE A

Antagonism of Iodinated Tachykinin Binding to $NK_1$ and $NK_2$ Receptors by Putative Antagonists One skilled in the art can determine the $NK_1$ receptor and $NK_2$ receptor affinity in vitro as follows. The $NK_1$ receptor affinity of tachykinin antagonists is evaluated in guinea pig lungs (Keystone Biologicals, Cleveland, Ohio) and affinity for the $NK_2$ receptor is evaluated in HSKR-1 cells (which are mouse 3T3 fibroblasts expressing the human jejunal $NK_2$ receptor). Tissues or cells are homogenized with a Polytron in 15 volumes of 50 mM Tris-HCl buffer (pH 7.4, 40° C.) and centrifuged. The pellet is resuspended in Tris-HCl buffer and is centrifuged; the pellet is washed twice by resuspension. The final pellet is resuspended at a concentration of 40 mg/ml for tissues and 20 mg/ml for cells in incubation buffer and remains at room temperature for at least 15 min prior to use. Receptor binding is initiated by addition of 250 ul membrane preparation in duplicate to 0.1 nM of the following radioligands: 125 I-Bolton Hunter Lys-3 labeled substance P and 125 iodohistidyl-1-neurokinin A; in a final volume of 500 ul of buffer containing 50 mM Tris-HCl (pH 7.4 at room temperature), 0.1% bovine serum albumin, 2 mM mangenese chloride, 40 ug/ml bacitracin, 4 $\mu$g/ml leupeptin and chymostatin, 10 $\mu$M thiorphan and various doses of the putative tachykinin antagonists. Incubations are performed at room temperature for 90 min ($NK_1$ receptor assays) or 2 hr ($NK_2$ receptor assay); binding is terminated by addition of 50 mM Tris-HCl buffer (pH 7.4, 40° C.) and filtration under vacuum through GF/B filters presoaked with 0.1% polyethyleneimine ($NK_1$ receptor assays) or 0.5% bovine serum albumin ($NK_2$ receptor assay). Filter bound radioactivity is quantitated in a gamma counter. Nonspecific binding is defined as binding in the presence of 1 $\mu$M substance P or neurokinin A. Specific binding is calculated by subtracting nonspecific binding from total binding. Competition of iodinated SP or NKA binding by test compounds or standards is expressed as a percentage of this maximum binding. $IC_{50}$ values (concentration required to inhibit 50% of receptor binding) are generated for each of the test compounds by nonlinear regression using an iterative curve fitting program (GraphPAD Inplot, San Diego, Calif.).

EXAMPLE B

Antagonism of Tachykinin-induced Phosphatidylinositol (PI) Turnover in Vitro by Putative Antagonists One skilled in the art can also determine the potency of $NK_1$ receptor and $NK_2$ receptor antagonism in vitro as follows. Tachykinin-mediated phosphatidylinositol (PI, inositol phosphate) accumulation is measured in UC11 or SKLKB82#3 cells in the presence and absence of $NK_1$ or $NK_2$ receptor antagonists, respectively. Tissues are incubated in Krebs-Henseleit buffer at 37° C. with 95% oxygen –5% carbon dioxide gassing. Tissues are then incubated with fresh buffer containing 100 $\mu$Ci of myo-[2–3 H(N)] inositol at 37° C. for 60 min with gentle gassing. After washing twice in 5 ml room temperature buffer containing 10 mM lithium chloride, tissues are incubated for 30 min at room temperature with a buffer change at 15 min. Buffer is removed and Krebs-Henseleit buffer (containing 40 $\mu$g/ml bacitracin, 4 $\mu$g/ml each of leupeptin and chymostatin, 0.1% bovine serum albumin and 10 $\mu$M of thiorphan and 10 mM of lithium chloride) including the test compound is added. After 15 min, SP is added to UC11 cells or NKA to SKLKB82#3 cells at various concentrations to start the reaction. After incubation for 60 min at room temperature the reaction is terminated by addition of 930 $\mu$l chloroform:methanol (1:2 by volume) to each tube, followed by 310 $\mu$l chloroform and 310 $\mu$l doubly distilled water. Samples are vortexed, centrifuged, and 0.9 ml of the aqueous (top) phase removed and added to 2 ml doubly distilled water. The mixture is vortexed and loaded onto a 50% Bio-Rad AG 1-X8 (formate form, 100–200 mesh) exchange column (Bio-Rad Laboratories, Hercules, Calif.). The columns are washed, in order, with: 1) 10 ml doubly distilled water, 2) 5 ml of 5 mM disodium tetraborate/60 mM sodium formate, and 3) 5 ml of 1 M ammonium formate/0.1 M formic acid. The third elution is collected and 1 ml counted in 7 ml scintillation fluid. A 50 $\mu$l aliquot of the organic (bottom) phase is removed, dried in a scintillation vial and counted in 7 ml scintillation fluid.

The ratio of DPM in the aqueous phase aliquot (total inositol phosphates) to the DPM in the 50 $\mu$l organic phase aliquot (total [ 3 H] inositol incorporated) is calculated for each sample. Data are expressed as a percent of agonist-induced accumulation of [ 3 H]-inositol phosphates over basal levels. The ratios in the presence of test compound and/or standards are compared to the ratios for control samples (i.e. no stimulating agonist).

Dose-response graphs are constructed and the ability of the test compounds to inhibit tachykinin-induced phosphatidyinositol turnover determined with the aid of a computer program. Data is expressed as percent stimulation of total inositol phosphate accumulation over basal levels and normalized to the maximum response produced by the tachykinin. Schild analysis is performed using dose response curves to obtain a value indicative of the strength of a competitive antagonist and is expressed as the pA2, which is the negative logarithm of the molar concentration of antagonist which reduces the effect of a dose of agonist to one-half of that expected at the dose of agonist. When the slope of the lines obtained by a Schild analysis are not significantly different from one (1) the compound is acting as a competitive antagonist.

EXAMPLE C

Evaluation of $NK_1$ Antagonism in Vivo

One skilled in the art can also determine that the compounds of the present invention are $NK_1$ receptor antagonists in vivo by evaluating the compound's ability to inhibit substance P-induced plasma protein extravasation in guinea pig trachea. Substance P-induced protein leakage through postcapillary venules is assessed by measuring Evans Blue dye accumulation in guinea pig trachea. Animals are anesthetized with pentobarbital then injected with Evans Blue dye (20 mg/kg, i.v., prepared in 0.9% sodium chloride solution). One minute after dye administration, the antagonist is administered (i.v.) followed by substance P (1.0 nmole/kg, i.v.) and, after 5 min, excess dye removed from the circulation by transcardiac perfusion with 50 ml 0.9% sodium chloride solution. The trachea and primary bronchi are removed, blotted dry and weighed.

Dye quantitation is performed spectrophotometrically (620 nm) after extracting tissues in formamide for 24 hr at 50° C. Values are subtracted from background (dye only, no agonist). ED50 (dose of compound which inhibits substance P-induced plasma protein extravasation by 50%) is calculated from linear regression analysis.

EXAMPLE D

Evaluation of $NK_2$ Antagonism in Vivo

One skilled in the art can determine that the compounds of the present invention are $NK_2$ receptor antagonists in vivo by evaluating the compound's ability to inhibit bronchoconstriction produced by a selective $NK_2$ receptor agonist,

[β-Ala$^8$] NKA 4–10 in guinea pigs. Animals are anesthetized with urethane and then cannulated via the jugular vein, carotid artery, and trachea. The carotid cannula is connected to t Statham pressure transducer to measure blood pressure and the catheter placed into the jugular vein is used to administer the test compounds. The trachea cannula is inserted into a T-connector and one arm of the T-connector is connected to a respiratory pump while the other arm is connected to another pressure transducer. The respiratory pump is adjusted to deliver 64 strokes per minute and the volume of air delivered is such that the insufflation pressure is 10 cm of water. Animals are permitted to acclimate for about 15 minutes until stable breathing and blood pressure are obtained. Putative tachykinin antagonists or vehicle are administered i.v. and the line flushed with water. Dose response curves are then generated for the $NK_2$ receptor selective antagonist, [β-Ala$^8$] NKA 4–10, at doses ranging form 1–30 nmole/kg, i.v. Bronchoconstriction is inferred from the dose-dependent increase in pulmonary insufflation pressure which occurs in response to the agonists. Antagonism of test compounds is inferred from a shift in the agonist dose-response curve to the right and suppression of the maximum insufflation pressure produced in response to [β-Ala$^8$] NKA 4–10.

EXAMPLE E

Evaluation of $NK_1$ and $NK_2$ Antagonism in Vivo

One skilled in the art can determine that the compounds of the present invention are $NK_2$ receptor antagonists in vivo by evaluating the compounds ability to inhibit capsaicin-induced respiratory effects, which is known to release both SP and NKA from airway sensory nerves. Antagonism of capsaicin induced respiratory effects in conscious guinea pigs is carried out as follows. In vivo experiments are performed using male Dunkin Hartley guinea pigs (250–350 g). Changes in conscious breathing patterns are monitored in four animals simultaneously using modified whole body plethysmography consisting of four small plexiglass boxes each connected to a reference box via Validyne DP 45-16 differential pressure transducers. The 4 boxes are equipped with an air supply line (also used for aerosol delivery) and an exhaust air line. Supply and exhaust lines are of the same length and narrow bore and arise from a common supply chamber and are vented to a common exhaust chamber. This system is used to ensure that fluctuations in supply air and atmospheric pressure remain in phase and are eliminated from the net signal by the differential pressure transducers. The analog pressure signals are digitalized via a Data Translation DT2821 A to D board. Data are collected at a rate of 100 samples/second/animal. Each cycle of pressure change is analyzed using the following parameters: rising and falling slope determined between minimum and maximum pressures, the ratio of rising over falling slope, and the magnitude of the change between initial trough pressure and peak cycle pressure. Using these values (and observing the animals) the pressure cycles are characterized into normal breaths, forced exhalations (apparent by abdominal heaving), significant respiratory events (SREs; usually coughs, less often sneezes or gasps which are characterized by transient, extremely large pressure increases which are distinguishable from noise) and movement/noise with a PCAT 286 running a System V UNIX operating system. Dyspnea is defined as a significant, sustained increase in plethysmograph pressure which is associated with an observable shift to labored breathing in the animal.

During the course of a typical experiment in which airway responsiveness to various bronchoconstricting agents is examined, aerosols are delivered for 19 min (0.33 ml/min) using a DeVilbiss Ultraneb 99 ultrasonic nebulizer and animals monitored during this time. Prior to nebulization, 1 min of resting breathing is collected to establish a baseline pressure. In preliminary experiments, various concentrations of capsaicin were evaluated and the concentration of 0.001% chosen which maximized the number of animals exhibiting dyspnea but minimized the severity of the response. Putative tachykinin antagonists are administered (i.v.) 20 minutes prior to onset of aerosol exposure or orally 1 hour prior to onset of aerosol exposure.

Tackykinin receptor binding ($IC_{50}$ value) for a representative compound of the present invention is found in Table 1. The value in Table 1 were determined by the method of present Example A and represents the mean of several experiments. This compound exhibits high affinity for both $NK_1$ and $NK_2$ receptors.

TABLE 1

| EXAMPLE NUMBER | Tachykinin Receptor Binding | |
|---|---|---|
| | $NK_1$ $IC_{50}$ (nM) | $NK_2$ $IC_{50}$ (nM) |
| 1.2 | 23 | 178 |

What is claimed is:
1. A compound of the formula

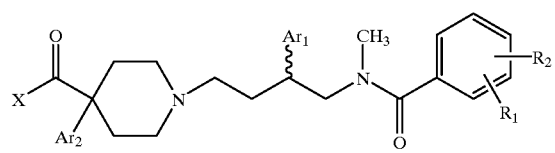

wherein
$R_1$ is from 1 to 3 substituents each independently chosen from the group consisting of hydrogen, halogen, $C_1$–$C_6$ alkyl, and $C_1$–$C_6$ alkoxy;
$R_2$ is hydrogen or a radical chosen from the group consisting of

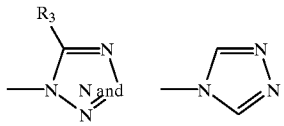

wherein
$R_3$ is selected from the group consisting of hydrogen, $C_1$–$C_4$ alkyl, and —$CF_3$;
$Ar_1$ is a radical chosen from the group consisting of

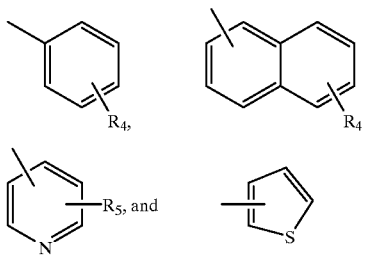

wherein
R₄ is from 1 to 3 substituents each independently chosen from the group consisting of hydrogen, halogen, hydroxy, —CF₃, C₁–C₆ alkyl, and C₁–C₆ alkoxy;
R₅ is from 1 to 2 substituents each independently chosen from the group consisting of hydrogen, halogen, C₁–C₆ alkyl, and C₁–C₆ alkoxy;
Ar₂ is a radical chosen from the group consisting of

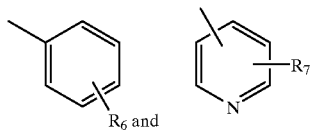

wherein
R₆ is from 1 to 3 substituents each independently chosen from the group consisting of hydrogen, halogen, —CF₃, C₁–C₆ alkyl, and C₁–C₆ alkoxy;
R₇ is from 1 to 2 substituents each independently chosen from the group consisting of hydrogen, halogen, C₁–C₆ alkyl, and C₁–C₆ alkoxy;
X is a radical selected from the group consisting of

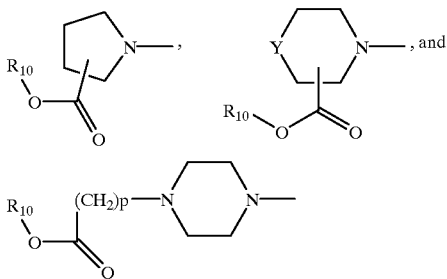

wherein
Y is —O— or —CH₂—;
p is an integer from 1 to 4;
R₁₀ is selected from the group consisting of hydrogen and C₁–C₆ alkyl;
and stereoisomers, and pharmaceutically acceptable salts thereof.

2. A compound of claim 1 wherein R₁ is 3,4,5-trimethoxy.

3. A compound of claim 1 wherein R₂ is the radical

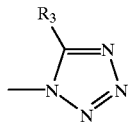

wherein R₃ is hydrogen.

4. A compound of claim 1 wherein R₁ is 2-methoxy and R₂ is in the 5-position and is the radical

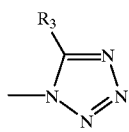

wherein R₃ is hydrogen.

5. A compound of claim 1 wherein Ar₁ is the radical

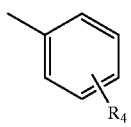

wherein R₄ is as defined in claim 1.

6. A compound of claim 1 wherein Ar₁ is selected from the group consisting of phenyl, 3,4-dichlorophenyl, and 4-fluorophenyl.

7. A compound of claim 1 wherein Ar₂ is phenyl.

8. A compound of claim 1 wherein X is the radical

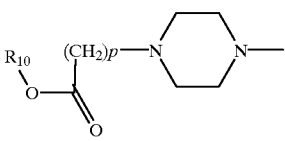

wherein p and R₁₀ are as defined in claim 1.

9. A compound of claim 8 wherein p is 1.

10. A compound of claim 8 wherein p is 2.

11. A compound as in either claim 9 or 10 wherein R₁₀ is hydrogen.

12. A compound as in either claim 9 or 10 wherein R₁₀ is ethyl.

13. A compound as in any one of claims 2, 3, 4, 5, 6, or 7 wherein X is the radical

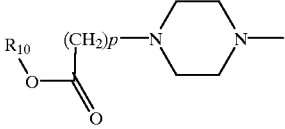

wherein p is 1 or 2 and R₁₀ is selected from the group consisting of hydrogen and ethyl.

14. A compound of claim 1 wherein R₁ is 3,4,5-trimethoxy, Ar₁ is the radical

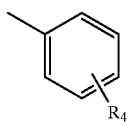

wherein R₄ is as defined in claim 1, Ar₂ is phenyl, and X is the radical

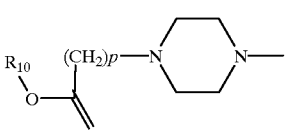

wherein p is 1 or 2 and R₁₀ is selected from the group consisting of hydrogen and ethyl.

15. A compound of claim 1 wherein $R_2$ is the radical

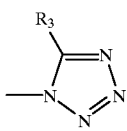

wherein $R_3$ is hydrogen, $Ar_1$ is the radical

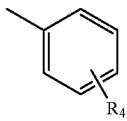

wherein $R_4$ is as defined in claim 1, $Ar_2$ is phenyl, and X is the radical

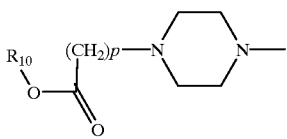

wherein p is 1 or 2 and $R_{10}$ is selected from the group consisting of hydrogen and ethyl.

16. A compound of claim 1 wherein $R_1$ is 2-methoxy and $R_2$ is in the 5-position and is the radical

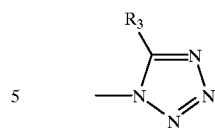

wherein $R_3$ is hydrogen, $Ar_1$ is selected from the group consisting of phenyl, 3,4-dichlorophenyl, and 4-fluorophenyl, $Ar_2$ is phenyl, and X is the radical

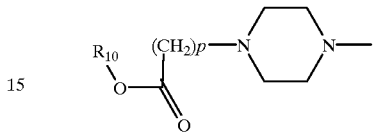

wherein p and $R_{10}$ are as defined in claim 1.

17. A compound of claim 16 wherein p is 1 or 2 and $R_{10}$ is hydrogen.

18. A compound of claim 16 wherein p is 1 or 2 and $R_{10}$ is ethyl.

19. A compound of claim 1 wherein the compound is (R)- or (S)-N-methyl-N-(4-(4-phenyl-4-((4-carboethoxymethylpiperazin-1-yl)carboxamido)piperidin-1-yl)-2-(3,4-dichlorophenyl)butyl)-2-methoxy-5-(1H-tetrazol-1-yl)benzamide or a mixture thereof.

20. A pharmaceutical composition comprising a compound of claim 1 and a pharmaceutically acceptable carrier.

21. A method for treating asthma in a patient in need thereof comprising administering to said patient a therapeutically effective amount of a compound of claim 1.

* * * * *